US010253325B2

(12) United States Patent
Puri et al.

(10) Patent No.: US 10,253,325 B2
(45) Date of Patent: Apr. 9, 2019

(54) METHODS FOR ELEVATING FAT/OIL CONTENT IN PLANTS

(71) Applicants: BOSTON MEDICAL CENTER CORPORATION, Boston, MA (US); UNIVERSITY OF NORTH TEXAS, Denton, TX (US)

(72) Inventors: Vishwajeet Puri, Hopkinton, MA (US); Kent Chapman, Denton, TX (US); Christopher James, Argyle, TX (US)

(73) Assignee: BOSTON MEDICAL CENTER CORPORATION, Boston, MA (US)

(*) Notice: Subject to any disclaimer, the term of this patent is extended or adjusted under 35 U.S.C. 154(b) by 154 days.

(21) Appl. No.: 13/830,012

(22) Filed: Mar. 14, 2013

(65) Prior Publication Data

US 2014/0173777 A1 Jun. 19, 2014

Related U.S. Application Data

(60) Provisional application No. 61/739,499, filed on Dec. 19, 2012.

(51) Int. Cl.
*C12N 15/82* (2006.01)
*C07K 14/415* (2006.01)
*C12P 7/64* (2006.01)

(52) U.S. Cl.
CPC ........ *C12N 15/8247* (2013.01); *C07K 14/415* (2013.01); *C12P 7/6463* (2013.01)

(58) Field of Classification Search
None
See application file for complete search history.

(56) References Cited

U.S. PATENT DOCUMENTS

| | | | |
|---|---|---|---|
| 4,761,373 A | 8/1988 | Anderson et al. | |
| 5,106,739 A | 4/1992 | Comai et al. | |
| 5,380,831 A | 1/1995 | Adang et al. | |
| 5,416,011 A | 5/1995 | Hinchee et al. | |
| 5,436,391 A | 7/1995 | Fujimoto | |
| 5,463,174 A | 10/1995 | Moloney et al. | |
| 5,591,616 A | 1/1997 | Hiei et al. | |
| 5,731,179 A | 3/1998 | Komari et al. | |
| 5,959,179 A | 9/1999 | Hinchee et al. | |
| 6,033,861 A | 3/2000 | Schafer et al. | |
| 6,037,527 A | 3/2000 | Barton et al. | |
| 6,153,812 A | 11/2000 | Fry et al. | |
| 6,160,208 A | 12/2000 | Lundquist et al. | |
| 6,171,820 B1 | 1/2001 | Short | |
| 6,773,900 B2 | 8/2004 | Short et al. | |
| 7,285,656 B2 | 10/2007 | Ekramoddoullah et al. | |
| 8,507,754 B2 * | 8/2013 | Chapman et al. | 800/281 |
| 8,735,111 B2 * | 5/2014 | Vanhercke et al. | 435/134 |
| 8,993,840 B2 | 3/2015 | Allen et al. | |
| 2005/0106697 A1 * | 5/2005 | Cases et al. | 435/193 |
| 2010/0021912 A1 | 1/2010 | Farese, Jr. et al. | |
| 2010/0095391 A1 * | 4/2010 | Silver | A01K 67/0275 800/13 |
| 2010/0221400 A1 | 9/2010 | Chapman et al. | |
| 2011/0126318 A1 | 5/2011 | Allen et al. | |
| 2011/0239318 A1 * | 9/2011 | Stephen | A01K 67/027 800/20 |
| 2011/0314725 A1 * | 12/2011 | Petrie | A23K 50/80 44/388 |
| 2012/0240289 A1 | 9/2012 | Feussner et al. | |
| 2015/0329870 A1 | 11/2015 | Puri et al. | |

FOREIGN PATENT DOCUMENTS

| | | |
|---|---|---|
| WO | WO-84/02913 A1 | 8/1984 |
| WO | WO-87/04181 A1 | 7/1987 |
| WO | WO-9958692 A2 | 11/1999 |
| WO | WO 2000/026374 A2 | 5/2000 |
| WO | WO200026374 * | 5/2000 |
| WO | WO-2010037130 A2 | 4/2010 |
| WO | WO-2011127118 A1 | 10/2011 |
| WO | WO-2012-075543 A1 | 6/2012 |
| WO | WO 2012/075543 A9 | 6/2012 |

OTHER PUBLICATIONS

Danesch et al. J. Biol. Chem. 267, 7185-7193, 1992.*
Puri et al. Lipid droplets: FSP27 knockout enhances their sizzle. J Clin Invest. 118(8):2693-2696. Aug. 2008.*
Zhang et al. DGAT1 and PDAT1 Acyltransferases Have Overlapping Functions in *Arabidopsis* Triacylglycerol Biosynthesis and Are Essential for Normal Pollen and Seed Development. The Plant Cell, vol. 21: 3885-3901, Dec. 2009.*
Puri et al (RNAi screens reveal novel metabolic regulators: RIP140, MAP4k4 and the lipid droplet associated fat specific protein (FSP) 27. Acta Physiol (Oxf). 192(1): 103-115, 2008).*
Keller et al (Fat-specific protein 27 regulates storage of triacylglycerol. J. Biol. Chem. 283:14355-14365(2008).*
Nishino et al (FSP27 contributes to efficient energy storage in murine white adipocytes by promoting the formation of unilocular lipid droplets. J Clin Invest. 118(8): 2808-2821, Aug. 2008).*

(Continued)

*Primary Examiner* — Medina A Ibrahim
*Assistant Examiner* — Wayne Zhong
(74) *Attorney, Agent, or Firm* — Saliwanchik, Lloyd & Eisenschenk

(57) ABSTRACT

In some embodiments, the present invention provides a method of elevating lipid content in vegetative (non-seed) plant or algae cells, plant tissues, or whole plants by genetically modifying the plant or algae to express a lipid droplet-associated protein or polypeptide (such as fat-specific protein 27) of mammalian origin. Also provided are genetically-modified plant or algae cells, plant tissues, or whole plants with elevated cellular lipid content, expressing a lipid droplet-associated protein or polypeptide (such as fat-specific protein 27) of mammalian (e.g. human) origin.

20 Claims, 10 Drawing Sheets

Specification includes a Sequence Listing.

(56) References Cited

OTHER PUBLICATIONS

Boutet et al (Seipin deficiency alters fatty acid Delta9 desaturation and lipid droplet formation in Berardinelli-Seip congenital lipodystrophy. Biochimie 91:796-803, 2009).*
Chapman et al (Biogenesis and Functions of Lipid Droplets in Plants, J. Lipid research, 2001).*
Puri et al. 'Fat-specific Protein 27, a Novel Lipid Droplet Protein That Enhances Triglyceride Storage,' Journal of Biological Chemistry. 282(47). pp. 34213-34218. Sep. 19, 2007.
Meinke et al. 'Leafy Cotyledon Mutants of *Arabidopsis*.' The Plant Cell. vol. 6, No. 8. pp. 1049-1064. Aug. 1994.
International Search Report dated Feb. 28, 2014 in International Application No. PCT/US2013/076672.
European Search Report dated Apr. 22, 2016 in European Application No. 13865188.0.
Desai, P., et al., "Production of heterologous proteins in plants: Strategies for optimal expression." *Biotechnology Advances* 28.4 (2010): 427-435.
Altschul, S.F. et al., "Basic Local Alignment Search Tool", *J. Mol. Biol.*, 1990, 215:403-410, 1990 Academic Press Limited.
Ballas, N. et al.,"Efficient functioning of plant promoters and poly(A) sites in *Xenopus* oocytes", *Nucleic Acids Research*, 1989, 17(19):7891-7903, IRL Press.
Benfey, P.N. et al., "The CaMV 35S enhancer contains at least two domains which can confer different developmental and tissue-specific expression patters", *The EMBO Journal*, 1989, 8(8):2195-2202, IRL Press.
Clough, S.J. et al., "Floral dip: a simplified method for *Agrobacterium*-mediated transformation of *Arabidopsis thaliana*", Technical Advance, *The Plant Journal*, 1998, 16(6):735-743, 1999 Blackwell Science Ltd.
Cagliari, A. et al., "Biosynthesis of Triacylglycerols (TAGs) in plants and algae", *International Journal of Plant Biology*, Oct. 2011, 2:e10:1-14.
Chapman, K.D. et al., "N-Acylphosphatidylethanolamine Synthesis in Plants: Occurrence, Molecular Composition, and Phospholipid Origin", *Archives of Biochemistry and Biophysics*, Feb. 15, 1993, 301(1): 21-33, 1993 Academic Press, Inc.
Chapman, K.D. et al., "Biogenesis and functions of lipid droplets in plants", *Thematic Review Series: Lipid Droplet Synthesis and Metabolism: from Yeast to Man, Journal of Lipid Research*, 2012, 53:215-226, 2012 the American Society for Biochemistry and Molecular Biology, Inc.
Chiang, L.W. et al., "Mutagenic Oligonucleotide-directed PCR Amplification (Mod-PCR): An Efficient Method for Generating Random Base Substitution Mutations in a DNA Sequence Element", Research, PCR Methods and Applications, 1993, 2:1-8, 1993 Cold Spring Harbor Laboratory.
Comai, L. et al., "Expression in plants of a mutant aroA gene from *Salmonella typhimurium* confers tolerance to glyphosate", *Nature*, Oct. 24, 1985, 317:741-744, 1985 Nature Publishing Group.
Coruzzi, G. et al., "Tissue-specific and light-regulated expression of a pea nuclear gene encoding the small subunit of ribulose-1, 5-bisphosphate carboxylase", *The EMBO Journal*, 1984, 3(8):1671-1679, IRL Press Limited, Oxford, England.
Curtis, M.D. et al., "A Gateway Cloning Vector Set for High-Throughput Functional Analysis of Genes in Planta[tw]", Breakthrough Technologies, *Plant Physiol.*, 2003, 133:462-469, 2003 American Society of Plant Biologists.
De Block, M. et al., "Engineering herbicide resistance in plants by expression of a detoxifying enzyme", *The EMBO Journal*, 1987, 6(9):2513-2518, IRL Press Limited, Oxford, England.
De Block, M. et al., "Transformation of *Brassica napus* and *Brassica oleracea* Using *Agrobacterium tumefaciens* and the Expression of the bar and neo Genes in the Transgenic Plants", *Plant Physiol.*, 1989, 91:694-701, 1989 American Society of Plant Biologists.
Della-Cioppa, G. et al., "Protein Trafficking in Plant Cells", *Plant Physiol.*, 1987, 84:965-968, 1987 American Society of Plant Biologists.
Dyer, J. et al., "Oil in Biomass: a step-change for bioenergy production?", *Biotechnology-renewable energy, inform*, Apr. 2012, pp. 206-210.
Elroy-Stein, O. et al., "Cap-independent translation of mRNA conferred by encephalomyocarditis virus 5' sequence improves the performance of the vaccinia virus/bacteriophage T7 hybrid expression system", Biochemistry, *Proc. Natl. Acad. Sci. USA*, Aug. 1989, 86:6126-6130.
Greener, A. et al., "An Efficient Random Mutagenesis Technique Using an *E. coli* Mutator Strain", In Vitro Mutagenesis Protocols, *Methods in Molecular Biology*™, 57:1-15.
Gross, D.A. et al., "Direct binding of triglyceride to fat storage-inducing transmembrane proteins 1 and 2 is important for lipid droplet formation", *PNAS*, Dec. 6, 2011, 108(49):19581-19586.
Guda, C. et al., "Stable expression of a biodegradable protein-based polymer in tobacco chloroplasts", *Plant Cell Reports*, 2000, 19:257-262, Springer-Verlag 2000.
Herrera-Esrella, L. et al., "Chimeric genes as dominant selectable markers in plant cells", *The EMBO Journal*, 1983, 2(6):987-995, IRL Press Limited, Oxford, England.
Herrera-Esrella, L. et al., "Expression of chimaeric genes transferred into plant cells using a Ti-plasmid-derived vector", *Nature*, May 19, 1983, 303:209-213, 1983 Macmillan Journals Ltd, 1983 Nature Publishing Group.
Hille, J. et al., "Bleomycin resistance: a new dominant selectable marker for plant cell transformation", *Plant Molecular Biology*, 1986, 7:171-176, Martinus Nijhoff Publishers, Dordrecht, Netherlands.
Hirschberg, J. et al., "Molecular Basis of Herbicide Resistance in *Amaranthus hybridus*",*Science*, 1983, 222(4630):1-5, the American Association for the Advancement of Science, The Authors.
Horsch, R.B. et al., "A Simple and General Method for Transferring Genes into Plants", *SCIENCE*, 1984, 227(4691):1-4, the American Association for the Advancement of Science, The Authors.
Jambunathan, S. et al., "FSP27 Promotes Lipid Droplet Clustering and Then Fusion to Regulate Triglyceride Accumulation", *PLoS ONE*, Dec. 14, 2011, 6(12):1-12, 2011 Jambunathan et al.
James, C.N. et al., "Disruption of the Arabidopsis CGI-58 homologue produces Chanarin-Dorfman-like lipid droplet accumulation in plants", *PNAS*, Oct. 12, 2010, 107(41):17833-17838.
Jobling, S.A. et al., "Enhancing translation of chimaeric messenger RNAs containing a plant viral untranslated leader sequence", *Nature*, Feb. 12, 1987, 325:622-625.
Joshi, C.P., "Putative polyadenylation signals in nuclear genes of higher plants: a compilation and analysis", *Nucleic Acids Research*, 1987, 15(23):9627-9640, IRL Press Limited, Oxford, England.
Kwok, W.W. et al., "Retroviral transfer of genes into canine hemopoietic progenitor cells in culture: A model for human gene therapy", Medical Sciences, *Proc. Natl. Acad. Sci. USA*, Jun. 1986, 83:4552-4555.
Macejak, D.G. et al., "Internal initiation of translation mediated by the 5' leader of a cellular mRNA", *Nature*, Sep. 5, 1991, 353:90-94, 1991 Nature Publishing Group.
Maier-Greiner, U.H. et al., "Isolation and properties of a nitrile hydratase from the soil fungus *Myrothecium verrucaria* that is highly specific for the fertilizer cyanamide and cloning of its gene", Biochemistry, *Proc. Natl. Acad. Sci. USA*, May 1991, 88:4260-4264.
Mogen, B.D. et al., "Upstream Sequences Other than AAUAAA Are Required for Efficient Messenger RNA 3' —End Formation in Plants", *The Plant Cell*, Dec. 1990, 2:1261-1272, 1990 American Society of Plant Physiologists.
Munroe, D. et al., "Tales of poly(A): a review (Protein synthesis; poly(A)-binding protein; 3'translational enhancer)", *Gene*, 1990, 91:151-158, 1990 Elsevier Science Publishers B.V.
Murray, E.E. et al., "Codon usage in plant genes", *Nucleic Acids Research*, 1989, 17(2):477-498.
Needleman, S.B. et al., "A General Method Applicable to the Search for Similarities in the Amino Acid Sequence of Two Proteins", *J. Mol. Biol.*, 1970, 48:443-453.
Parker, W.B. et al., "Selection and Characterization of Sethoxydim-Tolerant Maize Tissue Cultures", *Plant Physiol.*, 1990, 92:1220-1225, 1990 American Society of Plant Biologists.

(56) References Cited

OTHER PUBLICATIONS

Proudfoot, N., "Poly(A) Signals", *Cell*, Feb. 22, 1991, 64:671-674, 1991 Cell Press.

Puri, V. et al., "Cidea is associated with lipid droplets and insulin sensitivity in humans", *PNAS*, Jun. 3, 2008, 105(22):7833-7838, 2008 The National Academy of Sciences of the USA.

Rubio-Cabezas, O. et al., "Partial lipodystrophy and insulin resistant diabetes in a patient with a homozygous nonsense mutation in CIDEC", *EMBO Molecular Medicine*, 2009, 1:280-287, 2009 EMBO Molecular Medicine.

Sanfaçon, H. et al., "A dissection of the cauliflower mosaic virus polyadenylation signal", *GENES & Development*, 1990, 5:141-149, 1991 Cold Springs Harbor Laboratory Press.

Shah, D.M. et al., "Engineering Herbicide Tolerance in Transgenic Plants", *SCIENCE*, Jul. 25, 1986, 233:1-5.

Shimizu, Y. et al., "Transfer of Cloned Human Class I Major Histocompatibility Complex Genes into HLA Mutant Human Lymphoblastoid Cells", *Molecular and Cellular Biology*, Apr. 1986, 6(4):1074-1087, 1986 American Society for Microbiology.

Sivanandan, C. et al., "T-DNA tagging and characterization of a cryptic root-specific promoter in *Arabidopsis*", *Biochimica et biophysica Acta*, 2005, 1731:202-208, 2005 Elsevier B.V.

Stalker, D.M. et al., "Herbicide Resistance in Transgenic Plants Expressing a Bacterial Detoxification Gene", *Science*, Oct. 21, 1988, 242:1-6, the American Association for the Advancement of Science, The Authors.

Staub, J.M. et al., "Translation of psbA mRNA is regulated by light via the 5'-untranslated region in tobacco plastids", *The Plant Journal*, 1994, 6(4):547-553.

Stemmer, W.P.C., "DNA shuffling by random fragmentation and reassembly: In vitro recombination for molecular evolution", *Genetics, Proc. Natl. Acad. Sci. USA*, Oct. 1994, 91:10747-10751.

Sticklen, M., "Plant genetic engineering to improve biomass characteristics for biofuels", *Current Opinion in Biotechnology*, 2006, 17:315-319, 2006 Elsevier Ltd.

Szymanski, K.M. et al., "The lipodystrophy protein seipin is found at endoplasmic reticulum lipid droplet junctions and is important for droplet morphology", *PNAS*, Dec. 26, 2007, 14(52):20890-20895, 2007 The National Academy of Sciences of the USA.

Taylor, D.C. et al., "Molecular modification of triacylglycerol accumulation by over-expression of *DGAT1* to produce canola with increased seed oil content under field conditions", *Botany*, 2009, 87:533-543, NRC Research Press.

Toki, S. et al., "Expression of a Maize Ubiquitin Gene Promoter-bar Chimeric Gene in Transgenic Rice Plants", *Plant Physiol.*, 1992, 100:1503-1507, 1992 American Society of Plant Biologists.

Zhang, Y. et al., "Soybean GmDREBL Increases Lipid Content in Seeds of Transgenic Arabidopsis", *Scientific Reports*, Oct. 3, 2016, 6(34307):1-13, The Author(s) 2016.

Li, Z. et al., "Agronomic trait evaluation of field-grown transgenic rice plants containing the hygromycin resistance gene and the maize Activator element", *Plant Science*, 1995, 108:219-227, 1995 Elsevier Science Ireland Ltd.

Ohlrogge, J. et al., "The seeds of green energy", Expanding the contribution of plant oils as biofuels, *Features Bioenergy*, Apr. 2011, pp. 34-38, 2011 The Biochemical Society.

\* cited by examiner pMDC32
w/FSP27

35S=CaMV 35S promoter
HR=hygromycin resistance
RB=right border
LB=left border
NT=nos terminator pMDC43
w/FSP27

35S=CaMV 35S promoter
HR=hygromycin resistance
RB=right border
LB=left border
NT=nos terminator

SEQUENCE LISTING

```
<160> NUMBER OF SEQ ID NOS: 32

<210> SEQ ID NO 1
<211> LENGTH: 238
<212> TYPE: PRT
<213> ORGANISM: Homo sapiens

<400> SEQUENCE: 1

Met Glu Tyr Ala Met Lys Ser Leu Ser Leu Leu Tyr Pro Lys Ser Leu
1               5                   10                  15

Ser Arg His Val Ser Val Arg Thr Ser Val Val Thr Gln Gln Leu Leu
                20                  25                  30

Ser Glu Pro Ser Pro Lys Ala Pro Arg Ala Arg Pro Cys Arg Val Ser
            35                  40                  45

Thr Ala Asp Arg Ser Val Arg Lys Gly Ile Met Ala Tyr Ser Leu Glu
    50                  55                  60

Asp Leu Leu Lys Val Arg Asp Thr Leu Met Leu Ala Asp Lys Pro
65                  70                  75                  80

Phe Phe Leu Val Leu Glu Glu Asp Gly Thr Thr Val Glu Thr Glu Glu
                85                  90                  95

Tyr Phe Gln Ala Leu Ala Gly Asp Thr Val Phe Met Val Leu Gln Lys
            100                 105                 110

Gly Gln Lys Trp Gln Pro Pro Ser Glu Gln Gly Thr Arg His Pro Leu
        115                 120                 125

Ser Leu Ser His Lys Pro Ala Lys Lys Ile Asp Val Ala Arg Val Thr
    130                 135                 140

Phe Asp Leu Tyr Lys Leu Asn Pro Gln Asp Phe Ile Gly Cys Leu Asn
145                 150                 155                 160

Val Lys Ala Thr Phe Tyr Asp Thr Tyr Ser Leu Ser Tyr Asp Leu His
                165                 170                 175

Cys Cys Gly Ala Lys Arg Ile Met Lys Glu Ala Phe Arg Trp Ala Leu
            180                 185                 190

Phe Ser Met Gln Ala Thr Gly His Val Leu Leu Gly Thr Ser Cys Tyr
        195                 200                 205

Leu Gln Gln Leu Leu Asp Ala Thr Glu Glu Gly Gln Pro Pro Lys Gly
    210                 215                 220

Lys Ala Ser Ser Leu Ile Pro Thr Cys Leu Lys Ile Leu Gln
225                 230                 235

<210> SEQ ID NO 2
<211> LENGTH: 239
<212> TYPE: PRT
<213> ORGANISM: Mus musculus
```

<400> SEQUENCE: 2

```
Met Asp Tyr Ala Met Lys Ser Leu Ser Leu Leu Tyr Pro Arg Ser Leu
1               5                   10                  15

Ser Arg His Val Ala Val Ser Thr Ala Val Val Thr Gln Gln Leu Val
            20                  25                  30

Ser Lys Pro Ser Arg Glu Thr Pro Arg Ala Arg Pro Cys Arg Val Ser
        35                  40                  45

Thr Ala Asp Arg Lys Val Arg Lys Gly Ile Met Ala His Ser Leu Glu
    50                  55                  60

Asp Leu Leu Asn Lys Val Gln Asp Ile Leu Lys Leu Lys Asp Lys Pro
65                  70                  75                  80

Phe Ser Leu Val Leu Glu Glu Asp Gly Thr Ile Val Glu Thr Glu Glu
                85                  90                  95

Tyr Phe Gln Ala Leu Ala Lys Asp Thr Met Phe Met Val Leu Leu Lys
            100                 105                 110

Gly Gln Lys Trp Lys Pro Pro Ser Glu Gln Arg Lys Lys Arg Ala Gln
        115                 120                 125

Leu Ala Leu Ser Gln Lys Pro Thr Lys Lys Ile Asp Val Ala Arg Val
    130                 135                 140

Thr Phe Asp Leu Tyr Lys Leu Asn Pro Gln Asp Phe Ile Gly Cys Leu
145                 150                 155                 160

Asn Val Lys Ala Thr Leu Tyr Asp Thr Tyr Ser Leu Ser Tyr Asp Leu
                165                 170                 175

His Cys Tyr Lys Ala Lys Arg Ile Val Lys Glu Met Leu Arg Trp Thr
            180                 185                 190

Leu Phe Ser Met Gln Ala Thr Gly His Met Leu Leu Gly Thr Ser Ser
        195                 200                 205

Tyr Met Gln Gln Phe Leu Asp Ala Thr Glu Glu Gln Pro Ala Lys
    210                 215                 220

Ala Lys Pro Ser Ser Leu Leu Pro Ala Cys Leu Lys Met Leu Gln
225                 230                 235
```

<210> SEQ ID NO 3
<211> LENGTH: 522
<212> TYPE: PRT
<213> ORGANISM: Homo sapiens

<400> SEQUENCE: 3

```
Met Ala Val Asn Lys Gly Leu Thr Leu Leu Asp Gly Asp Leu Pro Glu
1               5                   10                  15

Gln Glu Asn Val Leu Gln Arg Val Leu Gln Leu Pro Val Val Ser Gly
            20                  25                  30

Thr Cys Glu Cys Phe Gln Lys Thr Tyr Ser Thr Lys Glu Ala His
        35                  40                  45

Pro Leu Val Ala Ser Val Cys Asn Ala Tyr Glu Lys Gly Val Gln Ser
    50                  55                  60

Ala Ser Ser Leu Ala Ala Trp Ser Met Glu Pro Val Val Arg Arg Leu
65                  70                  75                  80

Ser Thr Gln Phe Thr Ala Ala Asn Glu Leu Ala Cys Arg Gly Leu Asp
                85                  90                  95

His Leu Glu Glu Lys Ile Pro Ala Leu Gln Tyr Pro Pro Glu Lys Ile
            100                 105                 110

Ala Ser Glu Leu Lys Asp Thr Ile Ser Thr Arg Leu Arg Ser Ala Arg
        115                 120                 125
```

```
Asn Ser Ile Ser Val Pro Ile Ala Ser Thr Ser Asp Lys Val Leu Gly
130                 135                 140

Ala Ala Leu Ala Gly Cys Glu Leu Ala Trp Gly Val Ala Arg Asp Thr
145                 150                 155                 160

Ala Glu Phe Ala Ala Asn Thr Arg Ala Gly Arg Leu Ala Ser Gly Gly
                165                 170                 175

Ala Asp Leu Ala Leu Gly Ser Ile Glu Lys Val Val Glu Tyr Leu Leu
                180                 185                 190

Pro Pro Asp Lys Glu Glu Ser Ala Pro Ala Pro Gly His Gln Gln Ala
            195                 200                 205

Gln Lys Ser Pro Lys Ala Lys Pro Ser Leu Leu Ser Arg Val Gly Ala
210                 215                 220

Leu Thr Asn Thr Leu Ser Arg Tyr Thr Val Gln Thr Met Ala Arg Ala
225                 230                 235                 240

Leu Glu Gln Gly His Thr Val Ala Met Trp Ile Pro Gly Val Val Pro
                245                 250                 255

Leu Ser Ser Leu Ala Gln Trp Gly Ala Ser Val Ala Met Gln Ala Val
                260                 265                 270

Ser Arg Arg Ser Glu Val Arg Val Pro Trp Leu His Ser Leu Ala
275                 280                 285

Ala Ala Gln Glu Glu Asp His Glu Asp Gln Thr Asp Thr Glu Gly Glu
290                 295                 300

Asp Thr Glu Glu Glu Glu Leu Glu Thr Glu Glu Asn Lys Phe Ser
305                 310                 315                 320

Glu Val Ala Ala Leu Pro Gly Pro Arg Gly Leu Leu Gly Val Ala
                325                 330                 335

His Thr Leu Gln Lys Thr Leu Gln Thr Thr Ile Ser Ala Val Thr Trp
            340                 345                 350

Ala Pro Ala Ala Val Leu Gly Met Ala Gly Arg Val Leu His Leu Thr
            355                 360                 365

Pro Ala Pro Ala Val Ser Ser Thr Lys Gly Arg Ala Met Ser Leu Ser
370                 375                 380

Asp Ala Leu Lys Gly Val Thr Asp Asn Val Val Asp Thr Val Val His
385                 390                 395                 400

Tyr Val Pro Leu Pro Arg Leu Ser Leu Met Glu Pro Glu Ser Glu Phe
                405                 410                 415

Arg Asp Ile Asp Asn Pro Pro Ala Glu Val Glu Arg Glu Ala Glu
                420                 425                 430

Arg Arg Ala Ser Gly Ala Pro Ser Ala Gly Pro Glu Pro Ala Pro Arg
            435                 440                 445

Leu Ala Gln Pro Arg Arg Ser Leu Arg Ser Ala Gln Ser Pro Gly Ala
450                 455                 460

Pro Pro Gly Pro Gly Leu Glu Asp Glu Val Ala Thr Pro Ala Ala Pro
465                 470                 475                 480

Arg Pro Gly Phe Pro Ala Val Pro Arg Glu Lys Pro Lys Arg Arg Val
                485                 490                 495

Ser Asp Ser Phe Phe Arg Pro Ser Val Met Glu Pro Ile Leu Gly Arg
            500                 505                 510

Thr His Tyr Ser Gln Leu Arg Lys Lys Ser
            515                 520

<210> SEQ ID NO 4
<211> LENGTH: 517
```

<212> TYPE: PRT
<213> ORGANISM: Mus musculus

<400> SEQUENCE: 4

```
Met Ser Met Asn Lys Gly Pro Thr Leu Leu Asp Gly Asp Leu Pro Glu
1               5                   10                  15

Gln Glu Asn Val Leu Gln Arg Val Leu Gln Leu Pro Val Val Ser Gly
            20                  25                  30

Thr Cys Glu Cys Phe Gln Lys Thr Tyr Asn Ser Thr Lys Glu Ala His
        35                  40                  45

Pro Leu Val Ala Ser Val Cys Asn Ala Tyr Glu Lys Gly Val Gln Gly
    50                  55                  60

Ala Ser Asn Leu Ala Ala Trp Ser Met Glu Pro Val Val Arg Arg Leu
65                  70                  75                  80

Ser Thr Gln Phe Thr Ala Ala Asn Glu Leu Ala Cys Arg Gly Leu Asp
                85                  90                  95

His Leu Glu Glu Lys Ile Pro Ala Leu Gln Tyr Pro Pro Glu Lys Ile
            100                 105                 110

Ala Ser Glu Leu Lys Gly Thr Ile Ser Thr Arg Leu Arg Ser Ala Arg
        115                 120                 125

Asn Ser Ile Ser Val Pro Ile Ala Ser Thr Ser Asp Lys Val Leu Gly
    130                 135                 140

Ala Thr Leu Ala Gly Cys Glu Leu Ala Leu Gly Met Ala Lys Glu Thr
145                 150                 155                 160

Ala Glu Tyr Ala Ala Asn Thr Arg Val Gly Arg Leu Ala Ser Gly Gly
                165                 170                 175

Ala Asp Leu Ala Leu Gly Ser Ile Glu Lys Val Val Glu Phe Leu Leu
            180                 185                 190

Pro Pro Asp Lys Glu Ser Ala Pro Ser Ser Gly Arg Gln Arg Thr Gln
        195                 200                 205

Lys Ala Pro Lys Ala Lys Pro Ser Leu Val Arg Arg Val Ser Thr Leu
    210                 215                 220

Ala Asn Thr Leu Ser Arg His Thr Met Gln Thr Thr Ala Trp Ala Leu
225                 230                 235                 240

Lys Gln Gly His Ser Leu Ala Met Trp Ile Pro Gly Val Ala Pro Leu
                245                 250                 255

Ser Ser Leu Ala Gln Trp Gly Ala Ser Ala Met Gln Val Val Ser
            260                 265                 270

Arg Arg Gln Ser Glu Val Arg Val Pro Trp Leu His Asn Leu Ala Ala
        275                 280                 285

Ser Gln Asp Glu Ser His Asp Asp Gln Thr Asp Thr Glu Gly Glu Glu
    290                 295                 300

Thr Asp Asp Glu Glu Glu Glu Glu Ser Glu Ala Glu Glu Asn Val
305                 310                 315                 320

Leu Arg Glu Val Thr Ala Leu Pro Asn Pro Arg Gly Leu Leu Gly Gly
                325                 330                 335

Val Val His Thr Val Gln Asn Thr Leu Arg Asn Thr Ile Ser Ala Val
            340                 345                 350

Thr Trp Ala Pro Ala Ala Val Leu Gly Thr Val Gly Arg Ile Leu His
        355                 360                 365

Leu Thr Pro Ala Gln Ala Val Ser Ser Thr Lys Gly Arg Ala Met Ser
    370                 375                 380

Leu Ser Asp Ala Leu Lys Gly Val Thr Asp Asn Val Val Asp Thr Val
385                 390                 395                 400
```

```
Val His Tyr Val Pro Leu Pro Arg Leu Ser Leu Met Glu Pro Glu Ser
                405                 410                 415

Glu Phe Arg Asp Ile Asp Asn Pro Ser Ala Glu Ala Glu Arg Lys Gly
            420                 425                 430

Ser Gly Ala Arg Pro Ala Ser Pro Glu Ser Thr Pro Arg Pro Gly Gln
        435                 440                 445

Pro Arg Gly Ser Leu Arg Ser Val Arg Gly Leu Ser Ala Pro Ser Cys
    450                 455                 460

Pro Gly Leu Asp Asp Lys Thr Glu Ala Ser Ala Arg Pro Gly Phe Leu
465                 470                 475                 480

Ala Met Pro Arg Glu Lys Pro Ala Arg Arg Val Ser Asp Ser Phe Phe
                485                 490                 495

Arg Pro Ser Val Met Glu Pro Ile Leu Gly Arg Ala Gln Tyr Ser Gln
            500                 505                 510

Leu Arg Lys Lys Ser
        515

<210> SEQ ID NO 5
<211> LENGTH: 437
<212> TYPE: PRT
<213> ORGANISM: Homo sapiens

<400> SEQUENCE: 5

Met Ala Ser Val Ala Val Asp Pro Gln Pro Ser Val Val Thr Arg Val
1               5                   10                  15

Val Asn Leu Pro Leu Val Ser Ser Thr Tyr Asp Leu Met Ser Ser Ala
            20                  25                  30

Tyr Leu Ser Thr Lys Asp Gln Tyr Pro Tyr Leu Lys Ser Val Cys Glu
        35                  40                  45

Met Ala Glu Asn Gly Val Lys Thr Ile Thr Ser Val Ala Met Thr Ser
    50                  55                  60

Ala Leu Pro Ile Ile Gln Lys Leu Glu Pro Gln Ile Ala Val Ala Asn
65                  70                  75                  80

Thr Tyr Ala Cys Lys Gly Leu Asp Arg Ile Glu Glu Arg Leu Pro Ile
                85                  90                  95

Leu Asn Gln Pro Ser Thr Gln Ile Val Ala Asn Ala Lys Gly Ala Val
            100                 105                 110

Thr Gly Ala Lys Asp Ala Val Thr Thr Thr Val Thr Gly Ala Lys Asp
        115                 120                 125

Ser Val Ala Ser Thr Ile Thr Gly Val Met Asp Lys Thr Lys Gly Ala
    130                 135                 140

Val Thr Gly Ser Val Glu Lys Thr Lys Ser Val Val Ser Gly Ser Ile
145                 150                 155                 160

Asn Thr Val Leu Gly Ser Arg Met Met Gln Leu Val Ser Ser Gly Val
                165                 170                 175

Glu Asn Ala Leu Thr Lys Ser Glu Leu Leu Val Glu Gln Tyr Leu Pro
            180                 185                 190

Leu Thr Glu Glu Glu Leu Glu Lys Glu Ala Lys Lys Val Glu Gly Phe
        195                 200                 205

Asp Leu Val Gln Lys Pro Ser Tyr Tyr Val Arg Leu Gly Ser Leu Ser
    210                 215                 220

Thr Lys Leu His Ser Arg Ala Tyr Gln Gln Ala Leu Ser Arg Val Lys
225                 230                 235                 240

Glu Ala Lys Gln Lys Ser Gln Gln Thr Ile Ser Gln Leu His Ser Thr
```

```
                245                 250                 255
Val His Leu Ile Glu Phe Ala Arg Lys Asn Val Tyr Ser Ala Asn Gln
        260                 265                 270

Lys Ile Gln Asp Ala Gln Asp Lys Leu Tyr Leu Ser Trp Val Glu Trp
        275                 280                 285

Lys Arg Ser Ile Gly Tyr Asp Thr Asp Glu Ser His Cys Ala Glu
        290                 295                 300

His Ile Glu Ser Arg Thr Leu Ala Ile Ala Arg Asn Leu Thr Gln Gln
305                 310                 315                 320

Leu Gln Thr Thr Cys His Thr Leu Leu Ser Asn Ile Gln Gly Val Pro
            325                 330                 335

Gln Asn Ile Gln Asp Gln Ala Lys His Met Gly Val Met Ala Gly Asp
            340                 345                 350

Ile Tyr Ser Val Phe Arg Asn Ala Ala Ser Phe Lys Glu Val Ser Asp
            355                 360                 365

Ser Leu Leu Thr Ser Ser Lys Gly Gln Leu Gln Lys Met Lys Glu Ser
        370                 375                 380

Leu Asp Asp Val Met Asp Tyr Leu Val Asn Asn Thr Pro Leu Asn Trp
385                 390                 395                 400

Leu Val Gly Pro Phe Tyr Pro Gln Leu Thr Glu Ser Gln Asn Ala Gln
                405                 410                 415

Asp Gln Gly Ala Glu Met Asp Lys Ser Ser Gln Glu Thr Gln Arg Ser
            420                 425                 430

Glu His Lys Thr His
            435
```

<210> SEQ ID NO 6
<211> LENGTH: 425
<212> TYPE: PRT
<213> ORGANISM: Mus musculus

<400> SEQUENCE: 6

```
Met Ala Ala Ala Val Val Asp Pro Gln Gln Ser Val Val Met Arg Val
1               5                   10                  15

Ala Asn Leu Pro Leu Val Ser Ser Thr Tyr Asp Leu Val Ser Ser Ala
            20                  25                  30

Tyr Val Ser Thr Lys Asp Gln Tyr Pro Tyr Leu Arg Ser Val Cys Glu
        35                  40                  45

Met Ala Glu Lys Gly Val Lys Thr Val Thr Ser Ala Ala Met Thr Ser
    50                  55                  60

Ala Leu Pro Ile Ile Gln Lys Leu Glu Pro Gln Ile Ala Val Ala Asn
65                  70                  75                  80

Thr Tyr Ala Cys Lys Gly Leu Asp Arg Met Glu Glu Arg Leu Pro Ile
                85                  90                  95

Leu Asn Gln Pro Thr Ser Glu Ile Val Ala Ser Ala Arg Gly Ala Val
            100                 105                 110

Thr Gly Ala Lys Asp Val Val Thr Thr Met Ala Gly Ala Lys Asp
        115                 120                 125

Ser Val Ala Ser Thr Val Ser Gly Val Val Asp Lys Thr Lys Gly Ala
    130                 135                 140

Val Thr Gly Ser Val Glu Arg Thr Lys Ser Val Val Asn Gly Ser Ile
145                 150                 155                 160

Asn Thr Val Leu Gly Met Val Gln Phe Met Asn Ser Gly Val Asp Asn
                165                 170                 175
```

```
Ala Ile Thr Lys Ser Glu Leu Leu Val Asp Gln Tyr Phe Pro Leu Thr
            180                 185                 190

Gln Glu Glu Leu Glu Met Glu Ala Lys Lys Val Glu Gly Phe Asp Met
        195                 200                 205

Val Gln Lys Pro Ser Asn Tyr Glu Arg Leu Glu Ser Leu Ser Thr Lys
    210                 215                 220

Leu Cys Ser Arg Ala Tyr His Gln Ala Leu Ser Arg Val Lys Glu Ala
225                 230                 235                 240

Lys Gln Lys Ser Gln Glu Thr Ile Ser Gln Leu His Ser Thr Val His
                245                 250                 255

Leu Ile Glu Phe Ala Arg Lys Asn Met His Ser Ala Asn Gln Lys Ile
            260                 265                 270

Gln Gly Ala Gln Asp Lys Leu Tyr Val Ser Trp Val Glu Trp Lys Arg
        275                 280                 285

Ser Ile Gly Tyr Asp Asp Thr Asp Glu Ser His Cys Val Glu His Ile
    290                 295                 300

Glu Ser Arg Thr Leu Ala Ile Ala Arg Asn Leu Thr Gln Gln Leu Gln
305                 310                 315                 320

Thr Thr Cys Gln Thr Val Leu Val Asn Ala Gln Gly Leu Pro Gln Asn
                325                 330                 335

Ile Gln Asp Gln Ala Lys His Leu Gly Val Met Ala Gly Asp Ile Tyr
            340                 345                 350

Ser Val Phe Arg Asn Ala Ala Ser Phe Lys Glu Val Ser Asp Gly Val
        355                 360                 365

Leu Thr Ser Ser Lys Gly Gln Leu Gln Lys Met Lys Glu Ser Leu Asp
    370                 375                 380

Glu Val Met Asp Tyr Phe Val Asn Asn Thr Pro Leu Asn Trp Leu Val
385                 390                 395                 400

Gly Pro Phe Tyr Pro Gln Ser Thr Glu Val Asn Lys Ala Ser Leu Lys
                405                 410                 415

Val Gln Gln Ser Glu Val Lys Ala Gln
            420                 425

<210> SEQ ID NO 7
<211> LENGTH: 398
<212> TYPE: PRT
<213> ORGANISM: Homo sapiens

<400> SEQUENCE: 7

Met Val Asn Asp Pro Val Pro Ala Leu Leu Trp Ala Gln Glu Val
1               5                   10                  15

Gly Gln Val Leu Ala Gly Arg Ala Arg Arg Leu Leu Leu Gln Phe Gly
            20                  25                  30

Val Leu Phe Cys Thr Ile Leu Leu Leu Trp Val Ser Val Phe Leu
        35                  40                  45

Tyr Gly Ser Phe Tyr Ser Tyr Met Pro Thr Val Ser His Leu Ser
    50                  55                  60

Pro Val His Phe Tyr Tyr Arg Thr Asp Cys Asp Ser Ser Thr Thr Ser
65                  70                  75                  80

Leu Cys Ser Phe Pro Val Ala Asn Val Ser Leu Thr Lys Gly Gly Arg
                85                  90                  95

Asp Arg Val Leu Met Tyr Gly Gln Pro Tyr Arg Val Thr Leu Glu Leu
            100                 105                 110

Glu Leu Pro Glu Ser Pro Val Asn Gln Asp Leu Gly Met Phe Leu Val
        115                 120                 125
```

```
Thr Ile Ser Cys Tyr Thr Arg Gly Gly Arg Ile Ile Ser Thr Ser Ser
        130                 135                 140

Arg Ser Val Met Leu His Tyr Arg Ser Asp Leu Leu Gln Met Leu Asp
145                 150                 155                 160

Thr Leu Val Phe Ser Ser Leu Leu Phe Gly Phe Ala Glu Gln Lys
                165                 170                 175

Gln Leu Leu Glu Val Glu Leu Tyr Ala Asp Tyr Arg Glu Asn Ser Tyr
                180                 185                 190

Val Pro Thr Thr Gly Ala Ile Ile Glu Ile His Ser Lys Arg Ile Gln
                195                 200                 205

Leu Tyr Gly Ala Tyr Leu Arg Ile His Ala His Phe Thr Gly Leu Arg
        210                 215                 220

Tyr Leu Leu Tyr Asn Phe Pro Met Thr Cys Ala Phe Ile Gly Val Ala
225                 230                 235                 240

Ser Asn Phe Thr Phe Leu Ser Val Ile Val Leu Phe Ser Tyr Met Gln
                245                 250                 255

Trp Val Trp Gly Gly Ile Trp Pro Arg His Arg Phe Ser Leu Gln Val
                260                 265                 270

Asn Ile Arg Lys Arg Asp Asn Ser Arg Lys Glu Val Gln Arg Arg Ile
        275                 280                 285

Ser Ala His Gln Pro Gly Pro Glu Gly Gln Glu Glu Ser Thr Pro Gln
290                 295                 300

Ser Asp Val Thr Glu Asp Gly Glu Ser Pro Glu Asp Pro Ser Gly Thr
305                 310                 315                 320

Glu Gly Gln Leu Ser Glu Glu Lys Pro Asp Gln Gln Pro Leu Ser
                325                 330                 335

Gly Glu Glu Glu Leu Gly Pro Glu Ala Ser Asp Gly Ser Gly Ser Trp
                340                 345                 350

Glu Asp Ala Ala Leu Leu Thr Glu Ala Asn Leu Pro Ala Pro Ala Pro
            355                 360                 365

Ala Ser Ala Ser Ala Pro Val Leu Glu Thr Leu Gly Ser Ser Glu Pro
        370                 375                 380

Ala Gly Gly Ala Leu Arg Gln Arg Pro Thr Cys Ser Ser Ser
385                 390                 395

<210> SEQ ID NO 8
<211> LENGTH: 383
<212> TYPE: PRT
<213> ORGANISM: Mus musculus

<400> SEQUENCE: 8

Met Val Asn Asp Pro Pro Val Pro Ala Leu Leu Trp Ala Gln Glu Val
1               5                   10                  15

Gly His Val Leu Ala Gly Arg Ala Arg Arg Leu Met Leu Gln Phe Gly
                20                  25                  30

Val Leu Phe Cys Thr Ile Leu Leu Leu Trp Val Ser Val Phe Leu
            35                  40                  45

Tyr Gly Ser Phe Tyr Tyr Ser Tyr Met Pro Thr Val Ser His Leu Ser
    50                  55                  60

Pro Val His Phe His Tyr Arg Thr Asp Cys Asp Ser Ser Thr Ala Ser
65                  70                  75                  80

Leu Cys Ser Phe Pro Val Ala Asn Val Ser Leu Ala Lys Ser Gly Arg
                85                  90                  95

Asp Arg Val Leu Met Tyr Gly Gln Pro Tyr Arg Val Thr Leu Glu Leu
```

```
                 100                 105                 110
Glu Leu Pro Glu Ser Pro Val Asn Gln Asp Leu Gly Met Phe Leu Val
            115                 120                 125

Thr Val Ser Cys Tyr Thr Arg Gly Gly Arg Ile Ile Ser Thr Ser Ser
130                 135                 140

Arg Ser Val Met Leu His Tyr Arg Ser Gln Leu Leu Gln Val Leu Asp
145                 150                 155                 160

Thr Leu Leu Phe Ser Ser Leu Leu Leu Phe Gly Phe Ala Glu Gln Lys
                165                 170                 175

Gln Leu Leu Glu Val Glu Leu Tyr Ser Asp Tyr Arg Glu Asn Ser Tyr
            180                 185                 190

Val Pro Thr Thr Gly Ala Ile Ile Glu Ile His Ser Lys Arg Ile Gln
            195                 200                 205

Met Tyr Gly Ala Tyr Leu Arg Ile His Ala His Phe Thr Gly Leu Arg
        210                 215                 220

Tyr Leu Leu Tyr Asn Phe Pro Met Thr Cys Ala Phe Val Gly Val Ala
225                 230                 235                 240

Ser Asn Phe Thr Phe Leu Ser Val Ile Val Leu Phe Ser Tyr Met Gln
                245                 250                 255

Trp Val Trp Gly Ala Val Trp Pro Arg His Arg Phe Ser Leu Gln Val
            260                 265                 270

Asn Ile Arg Gln Arg Asp Asn Ser His His Gly Ala Pro Arg Arg Ile
        275                 280                 285

Ser Arg His Gln Pro Gly Gln Glu Ser Thr Gln Gln Ser Asp Val Thr
    290                 295                 300

Glu Asp Gly Glu Ser Pro Glu Asp Pro Ser Gly Thr Glu Gly Gln Leu
305                 310                 315                 320

Ser Glu Glu Glu Lys Pro Glu Lys Arg Pro Leu Asn Gly Glu Glu Glu
                325                 330                 335

Gln Glu Pro Glu Ala Ser Asp Gly Ser Trp Glu Asp Ala Ala Leu Leu
            340                 345                 350

Thr Glu Ala Asn Pro Pro Thr Ser Ala Ser Ala Ser Ala Leu Ala Pro
        355                 360                 365

Glu Thr Leu Gly Ser Leu Arg Gln Arg Pro Thr Cys Ser Ser Ser
    370                 375                 380

<210> SEQ ID NO 9
<211> LENGTH: 292
<212> TYPE: PRT
<213> ORGANISM: Homo sapiens

<400> SEQUENCE: 9

Met Glu Arg Gly Pro Val Val Gly Ala Gly Leu Gly Ala Gly Ala Arg
1               5                   10                  15

Ile Gln Ala Leu Leu Gly Cys Leu Leu Lys Val Leu Leu Trp Val Ala
            20                  25                  30

Ser Ala Leu Leu Tyr Phe Gly Ser Glu Gln Ala Ala Arg Leu Leu Gly
        35                  40                  45

Ser Pro Cys Leu Arg Arg Leu Tyr His Ala Trp Leu Ala Ala Val Val
    50                  55                  60

Ile Phe Gly Pro Leu Leu Gln Phe His Val Asn Pro Arg Thr Ile Phe
65                  70                  75                  80

Ala Ser His Gly Asn Phe Phe Asn Ile Lys Phe Val Asn Ser Ala Trp
                85                  90                  95
```

Gly Trp Thr Cys Thr Phe Leu Gly Gly Phe Val Leu Val Val Phe
            100                 105                 110

Leu Ala Thr Arg Arg Val Ala Val Thr Ala Arg His Leu Ser Arg Leu
            115                 120                 125

Val Val Gly Ala Ala Val Trp Arg Gly Ala Gly Arg Ala Phe Leu Leu
        130                 135                 140

Ile Glu Asp Leu Thr Gly Ser Cys Phe Glu Pro Leu Pro Gln Gly Leu
145                 150                 155                 160

Leu Leu His Glu Leu Pro Asp Arg Arg Ser Cys Leu Ala Ala Gly His
                165                 170                 175

Gln Trp Arg Gly Tyr Thr Val Ser Ser His Thr Phe Leu Leu Thr Phe
            180                 185                 190

Cys Cys Leu Leu Met Ala Glu Glu Ala Ala Val Phe Ala Lys Tyr Leu
        195                 200                 205

Ala His Gly Leu Pro Ala Gly Ala Pro Leu Arg Leu Val Phe Leu Leu
    210                 215                 220

Asn Val Leu Leu Leu Gly Leu Trp Asn Phe Leu Leu Leu Cys Thr Val
225                 230                 235                 240

Ile Tyr Phe His Gln Tyr Thr His Lys Val Val Gly Ala Ala Val Gly
                245                 250                 255

Thr Phe Ala Trp Tyr Leu Thr Tyr Gly Ser Trp Tyr His Gln Pro Trp
            260                 265                 270

Ser Pro Gly Ser Pro Gly His Gly Leu Phe Pro Arg Pro His Ser Ser
        275                 280                 285

Arg Lys His Asn
    290

<210> SEQ ID NO 10
<211> LENGTH: 292
<212> TYPE: PRT
<213> ORGANISM: Mus musculus

<400> SEQUENCE: 10

Met Glu Arg Gly Pro Thr Val Gly Ala Gly Leu Gly Ala Gly Thr Arg
1               5                   10                  15

Val Arg Ala Leu Leu Gly Cys Leu Val Lys Val Leu Leu Trp Val Ala
            20                  25                  30

Ser Ala Leu Leu Tyr Phe Gly Ser Glu Gln Ala Ala Arg Leu Leu Gly
        35                  40                  45

Ser Pro Cys Leu Arg Arg Leu Tyr His Ala Trp Leu Ala Ala Val Val
    50                  55                  60

Ile Phe Gly Pro Leu Leu Gln Phe His Val Asn Ser Arg Thr Ile Phe
65                  70                  75                  80

Ala Ser His Gly Asn Phe Phe Asn Ile Lys Phe Val Asn Ser Ala Trp
                85                  90                  95

Gly Trp Thr Cys Thr Phe Leu Gly Gly Phe Val Leu Val Val Phe
            100                 105                 110

Leu Ala Thr Arg Arg Val Ala Val Thr Ala Arg His Leu Ser Arg Leu
            115                 120                 125

Val Val Gly Ala Ala Val Trp Arg Gly Ala Gly Arg Ala Phe Leu Leu
        130                 135                 140

Ile Glu Asp Leu Thr Gly Ser Cys Phe Glu Pro Leu Pro Gln Gly Leu
145                 150                 155                 160

Leu Leu His Glu Leu Pro Asp Arg Lys Ser Cys Leu Ala Ala Gly His
                165                 170                 175

```
Gln Trp Arg Gly Tyr Thr Val Ser Ser His Thr Phe Leu Leu Thr Phe
                180                 185                 190

Cys Cys Leu Leu Met Ala Glu Glu Ala Ala Val Phe Ala Lys Tyr Leu
            195                 200                 205

Ala His Gly Leu Pro Ala Gly Ala Pro Leu Arg Leu Val Phe Leu Leu
        210                 215                 220

Asn Val Leu Leu Gly Leu Trp Asn Phe Leu Leu Cys Thr Val
225                 230                 235                 240

Ile Tyr Phe His Gln Tyr Thr His Lys Val Val Gly Ala Ala Val Gly
                245                 250                 255

Thr Phe Ala Trp Tyr Leu Thr Tyr Gly Ser Trp Tyr His Gln Pro Trp
            260                 265                 270

Ser Pro Gly Ile Pro Gly His Gly Leu Phe Pro Arg Ser Arg Ser Met
        275                 280                 285

Arg Lys His Asn
    290

<210> SEQ ID NO 11
<211> LENGTH: 262
<212> TYPE: PRT
<213> ORGANISM: Homo sapiens

<400> SEQUENCE: 11

Met Glu His Leu Glu Arg Cys Glu Trp Leu Leu Arg Gly Thr Leu Val
1               5                   10                  15

Arg Ala Ala Val Arg Arg Tyr Leu Pro Trp Ala Leu Val Ala Ser Met
            20                  25                  30

Leu Ala Gly Ser Leu Leu Lys Glu Leu Ser Pro Leu Pro Glu Ser Tyr
        35                  40                  45

Leu Ser Asn Lys Arg Asn Val Leu Asn Val Tyr Phe Val Lys Val Ala
    50                  55                  60

Trp Ala Trp Thr Phe Cys Leu Leu Pro Phe Ile Ala Leu Thr Asn
65                  70                  75                  80

Tyr His Leu Thr Gly Lys Ala Gly Leu Val Leu Arg Arg Leu Ser Thr
                85                  90                  95

Leu Leu Val Gly Thr Ala Ile Trp Tyr Ile Cys Thr Ser Ile Phe Ser
            100                 105                 110

Asn Ile Glu His Tyr Thr Gly Ser Cys Tyr Gln Ser Pro Ala Leu Glu
        115                 120                 125

Gly Val Arg Lys Glu His Gln Ser Lys Gln Cys His Gln Glu Gly
    130                 135                 140

Gly Phe Trp His Gly Phe Asp Ile Ser Gly His Ser Phe Leu Leu Thr
145                 150                 155                 160

Phe Cys Ala Leu Met Ile Val Glu Glu Met Ser Val Leu His Glu Val
                165                 170                 175

Lys Thr Asp Arg Ser His Cys Leu His Thr Ala Ile Thr Thr Leu Val
            180                 185                 190

Val Ala Leu Gly Ile Leu Thr Phe Ile Trp Val Leu Met Phe Leu Cys
        195                 200                 205

Thr Ala Val Tyr Phe His Asn Leu Ser Gln Lys Val Phe Gly Thr Leu
    210                 215                 220

Phe Gly Leu Leu Ser Trp Tyr Gly Thr Tyr Gly Phe Trp Tyr Pro Lys
225                 230                 235                 240

Ala Phe Ser Pro Gly Leu Pro Pro Gln Ser Cys Ser Leu Asn Leu Lys
```

Gln Asp Ser Tyr Lys Lys
            260

<210> SEQ ID NO 12
<211> LENGTH: 262
<212> TYPE: PRT
<213> ORGANISM: Mus musculus

<400> SEQUENCE: 12

Met Glu His Leu Glu Arg Cys Ala Trp Phe Leu Arg Gly Thr Leu Val
1               5                   10                  15

Arg Ala Thr Val Arg Arg His Leu Pro Trp Ala Leu Val Ala Ala Met
            20                  25                  30

Leu Ala Gly Ser Val Val Lys Glu Leu Ser Pro Leu Pro Glu Ser Tyr
        35                  40                  45

Leu Ser Asn Lys Arg Asn Val Leu Asn Val Tyr Phe Val Lys Leu Ala
    50                  55                  60

Trp Ala Trp Thr Val Cys Leu Leu Pro Phe Ile Ala Leu Thr Asn
65                  70                  75                  80

Tyr His Leu Thr Gly Lys Thr Ser Leu Val Leu Arg Arg Leu Ser Thr
                85                  90                  95

Leu Leu Val Gly Thr Ala Ile Trp Tyr Ile Cys Thr Ala Leu Phe Ser
            100                 105                 110

Asn Ile Glu His Tyr Thr Gly Ser Cys Tyr Gln Ser Pro Ala Leu Glu
        115                 120                 125

Gly Ile Arg Gln Glu His Arg Ser Lys Gln Gln Cys His Arg Glu Gly
    130                 135                 140

Gly Phe Trp His Gly Phe Asp Ile Ser Gly His Ser Phe Leu Leu Thr
145                 150                 155                 160

Phe Cys Ala Leu Met Ile Val Glu Glu Met Ala Val Leu His Glu Val
                165                 170                 175

Lys Thr Asp Arg Gly His His Leu His Ala Ala Ile Thr Thr Leu Val
            180                 185                 190

Val Ala Leu Gly Phe Leu Thr Phe Ile Trp Val Trp Met Phe Leu Cys
        195                 200                 205

Thr Ala Val Tyr Phe His Asp Leu Thr Gln Lys Val Phe Gly Thr Met
    210                 215                 220

Phe Gly Leu Leu Gly Trp Tyr Gly Thr Tyr Gly Tyr Trp Tyr Leu Lys
225                 230                 235                 240

Ser Phe Ser Pro Gly Leu Pro Pro Gln Ser Cys Ser Leu Thr Leu Lys
                245                 250                 255

Arg Asp Thr Tyr Lys Lys
            260

<210> SEQ ID NO 13
<211> LENGTH: 1702
<212> TYPE: DNA
<213> ORGANISM: Arabidopsis thaliana

<400> SEQUENCE: 13
agaaaattta gtagcaaact tctcgattcc ttgattcgtg ggaaaaagaa agtctagatt      60
tttgtggatt ttgatttgt gattccgtga ttgtatgaac ttgagccgtt ttgcttcgag     120
attaagaatg gcggaagaaa tctcaaagac gaaggtggga tcttcttcta ctgcttcggt     180
ggctgattca tctgctgctg cgtcggctgc aacgaatgcg gccaaatcaa gatggaaaat     240

```
tttgtggcct aattcgctcc ggtggattcc tacgtccacc gattacatca tcgccgccga    300
gaaacgtctt ctctccatcc tcaagacgcc ttatgtacaa gagcaagtca gtattggttc    360
aggaccacca ggttctaaaa tcaggtggtt taggtctacg agcaatgagt cacgttacat    420
caacactgtt acatttgatg ccaaggaggg agctcctaca ctcgtcatgg ttcatggtta    480
tggtgcttct caagggtttt tcttccgtaa ttttgatgct cttgccagtc gatttagagt    540
gatcgctatt gatcaacttg ggtggggtgg ttcaagtagg cctgatttta catgtagaag    600
cacagaagaa actgaggcat ggtttatcga ctcctttgag gaatggcgta aagcccagaa    660
tctcagtaac tttattctat taggacattc ttttggaggc tatgttgctg ctaaatacgc    720
gcttaagcat cctgaacatg ttcaacactt aattctggtg ggatctgctg ggttctcagc    780
agaagcagat gccaaatcag aatggctcac taaatttaga gcaacatgga aaggtgcagt    840
cctaaatcat ttatgggagt caaatttcac tcctcagaag ctggttagag gattaggtcc    900
ttggggtcca ggtcttgtaa atcggtatac aactgcaaga tttggtgcac attcggaggg    960
aactgggcta acagaagagg aagccaaatt gctaaccgat tatgtgtacc atactttggc   1020
tgcaaaggct agtggagagt tatgcttgaa atacatcttc tcatttggag catttgctag   1080
gaagcccctc ttacaaaggt atgtccacca aaaacattgc tgataaagtt tctgcatact   1140
cacactcgat gactcctctt ttgtgtgcag tgcatcagag tggaaagtgc aacaacgtt    1200 tatctatgga atgaatgatt ggatgaacta tcaaggtgcg gtggaagcga ggaaatccat   1260
gaaggtccct tgcgaaatca ttcgggttcc acagggtggt cattttgtgt tcatagacaa   1320
cccaattggt tttcattctg cagtgcttta tgcttgccgc aagtttatat ctcaagactc   1380
ctctcatgat caacaactcc tagatggtct acgattggtt tagtcatagt atcttgttcc   1440
ttttaccttc caaatttatt ctatatgtgt atacaagtat atatgaaaaa gaacataaaa   1500
aagaattact ttctttattt gaatattcgg ttgtgtattg gagtttcaag tcctctttcc   1560
atgtctaaaa gttctatttg taacgttctt gatttcactc taaaacctct taaagtgttt   1620
caaatgtgat ctcattatcg acatccaagt tgtaatcttt cacaatccac aataatcttt   1680
tatctcattt tttacatttt ac                                            1702
```

<210> SEQ ID NO 14
<211> LENGTH: 418
<212> TYPE: PRT
<213> ORGANISM: Arabidopsis thaliana

<400> SEQUENCE: 14

```
Met Asn Leu Ser Arg Phe Ala Ser Arg Leu Arg Met Ala Glu Glu Ile
1               5                   10                  15

Ser Lys Thr Lys Val Gly Ser Ser Ser Thr Ala Ser Val Ala Asp Ser
            20                  25                  30

Ser Ala Ala Ala Ser Ala Ala Thr Asn Ala Ala Lys Ser Arg Trp Lys
        35                  40                  45

Ile Leu Trp Pro Asn Ser Leu Arg Trp Ile Pro Thr Ser Thr Asp Tyr
    50                  55                  60

Ile Ile Ala Ala Glu Lys Arg Leu Leu Ser Ile Leu Lys Thr Pro Tyr
65                  70                  75                  80

Val Gln Glu Gln Val Ser Ile Gly Ser Gly Pro Pro Gly Ser Lys Ile
                85                  90                  95

Arg Trp Phe Arg Ser Thr Ser Asn Glu Ser Arg Tyr Ile Asn Thr Val
            100                 105                 110
```

Thr Phe Asp Ala Lys Glu Gly Ala Pro Thr Leu Val Met Val His Gly
            115                 120                 125

Tyr Gly Ala Ser Gln Gly Phe Phe Arg Asn Phe Asp Ala Leu Ala
        130                 135                 140

Ser Arg Phe Arg Val Ile Ala Ile Asp Gln Leu Gly Trp Gly Gly Ser
145                 150                 155                 160

Ser Arg Pro Asp Phe Thr Cys Arg Ser Thr Glu Glu Thr Glu Ala Trp
                165                 170                 175

Phe Ile Asp Ser Phe Glu Glu Trp Arg Lys Ala Gln Asn Leu Ser Asn
            180                 185                 190

Phe Ile Leu Leu Gly His Ser Phe Gly Gly Tyr Val Ala Ala Lys Tyr
            195                 200                 205

Ala Leu Lys His Pro Glu His Val Gln His Leu Ile Leu Val Gly Ser
        210                 215                 220

Ala Gly Phe Ser Ala Glu Ala Asp Ala Lys Ser Glu Trp Leu Thr Lys
225                 230                 235                 240

Phe Arg Ala Thr Trp Lys Gly Ala Val Leu Asn His Leu Trp Glu Ser
                245                 250                 255

Asn Phe Thr Pro Gln Lys Leu Val Arg Gly Leu Gly Pro Trp Gly Pro
            260                 265                 270

Gly Leu Val Asn Arg Tyr Thr Thr Ala Arg Phe Gly Ala His Ser Glu
        275                 280                 285

Gly Thr Gly Leu Thr Glu Glu Ala Lys Leu Leu Thr Asp Tyr Val
        290                 295                 300

Tyr His Thr Leu Ala Ala Lys Ala Ser Gly Glu Leu Cys Leu Lys Tyr
305                 310                 315                 320

Ile Phe Ser Phe Gly Ala Phe Ala Arg Lys Pro Leu Leu Gln Ser Ala
                325                 330                 335

Ser Glu Trp Lys Val Pro Thr Thr Phe Ile Tyr Gly Met Asn Asp Trp
            340                 345                 350

Met Asn Tyr Gln Gly Ala Val Glu Ala Arg Lys Ser Met Lys Val Pro
        355                 360                 365

Cys Glu Ile Ile Arg Val Pro Gln Gly Gly His Phe Val Phe Ile Asp
    370                 375                 380

Asn Pro Ile Gly Phe His Ser Ala Val Leu Tyr Ala Cys Arg Lys Phe
385                 390                 395                 400

Ile Ser Gln Asp Ser Ser His Asp Gln Gln Leu Leu Asp Gly Leu Arg
                405                 410                 415

Leu Val

<210> SEQ ID NO 15
<211> LENGTH: 521
<212> TYPE: PRT
<213> ORGANISM: Jatropha curcas

<400> SEQUENCE: 15

Met Thr Ile Leu Glu Thr Thr Thr Ser Gly Gly Asp Gly Val Ala Glu
1               5                   10                  15

Ser Ser Asp Leu Asn Val Ser Leu Arg Arg Arg Lys Gly Thr
            20                  25                  30

Ser Ser Asp Gly Ala Leu Pro Glu Leu Thr Ser Asn Ile Val Glu Leu
        35                  40                  45

Glu Ser Glu Ser Gly Gly Gln Val Met Met Asp Pro Gly Met Val Thr
50                  55                  60

Glu Pro Glu Thr Glu Lys Ile Asn Gly Lys Asp Cys Gly Gly Asp Lys
65                  70                  75                  80

Asp Lys Ile Asp Asn Arg Glu Asn Arg Gly Arg Ser Asp Ile Lys Phe
            85                  90                  95

Thr Tyr Arg Pro Ser Val Pro Ala His Arg Ala Leu Arg Glu Ser Pro
            100                 105                 110

Leu Ser Ser Asp Ala Ile Phe Lys Gln Ser His Ala Gly Leu Phe Asn
            115                 120                 125

Leu Cys Ile Val Val Leu Val Ala Val Asn Ser Arg Leu Ile Ile Glu
130                 135                 140

Asn Leu Met Lys Tyr Gly Trp Leu Ile Lys Thr Gly Phe Trp Phe Ser
145                 150                 155                 160

Ser Arg Ser Leu Arg Asp Trp Pro Leu Leu Met Cys Cys Leu Thr Leu
            165                 170                 175

Pro Ile Phe Ser Leu Ala Ala Tyr Leu Val Glu Lys Leu Ala Tyr Arg
            180                 185                 190

Lys Tyr Ile Ser Ala Pro Ile Val Phe Phe His Met Leu Ile Thr
            195                 200                 205

Thr Thr Ala Val Leu Tyr Pro Val Ser Val Ile Leu Ser Cys Gly Ser
210                 215                 220

Ala Val Leu Ser Gly Val Ala Leu Met Leu Phe Ala Cys Ile Val Trp
225                 230                 235                 240

Leu Lys Leu Val Ser Tyr Ala His Thr Asn Tyr Asp Met Arg Ala Ile
            245                 250                 255

Ala Asn Ser Ala Asp Lys Gly Asp Ala Leu Ser Asp Thr Ser Gly Ala
            260                 265                 270

Asp Ser Ser Arg Asp Val Ser Phe Lys Ser Leu Val Tyr Phe Met Val
            275                 280                 285

Ala Pro Thr Leu Cys Tyr Gln Pro Ser Tyr Pro Arg Thr Asp Ser Val
290                 295                 300

Arg Lys Gly Trp Val Val Arg Gln Phe Val Lys Leu Ile Ile Phe Thr
305                 310                 315                 320

Gly Phe Met Gly Phe Ile Ile Glu Gln Tyr Ile Asn Pro Ile Val Gln
            325                 330                 335

Asn Ser Gln His Pro Leu Lys Gly Asp Leu Leu Tyr Ala Ile Glu Arg
            340                 345                 350

Val Leu Lys Leu Ser Val Pro Asn Leu Tyr Val Trp Leu Cys Met Phe
            355                 360                 365

Tyr Cys Phe Phe His Leu Trp Leu Asn Ile Leu Ala Glu Leu Leu Arg
            370                 375                 380

Phe Gly Asp Arg Glu Phe Tyr Lys Asp Trp Trp Asn Ala Arg Thr Val
385                 390                 395                 400

Glu Glu Tyr Trp Arg Met Trp Asn Met Pro Val His Lys Trp Met Val
            405                 410                 415

Arg His Ile Tyr Phe Pro Cys Leu Arg His Lys Ile Pro Arg Gly Val
            420                 425                 430

Ala Leu Leu Ile Ala Phe Phe Val Ser Ala Val Phe His Glu Leu Cys
            435                 440                 445

Ile Ala Val Pro Cys His Met Phe Lys Leu Trp Ala Phe Ile Gly Ile
            450                 455                 460

Met Phe Gln Ile Pro Leu Val Gly Ile Thr Asn Tyr Leu Gln Asn Lys
465                 470                 475                 480

```
Phe Arg Ser Ser Met Val Gly Asn Met Ile Phe Trp Phe Ile Phe Cys
                485                 490                 495

Ile Leu Gly Gln Pro Met Cys Val Leu Leu Tyr Tyr His Asp Leu Met
            500                 505                 510

Asn Arg Lys Gly Asn Ala Glu Leu Arg
        515                 520

<210> SEQ ID NO 16
<211> LENGTH: 671
<212> TYPE: PRT
<213> ORGANISM: Arabidopsis thaliana

<400> SEQUENCE: 16

Met Pro Leu Ile His Arg Lys Lys Pro Thr Glu Lys Pro Ser Thr Pro
1               5                   10                  15

Pro Ser Glu Glu Val Val His Asp Glu Asp Ser Gln Lys Lys Pro His
            20                  25                  30

Glu Ser Ser Lys Ser His His Lys Lys Ser Asn Gly Gly Lys Trp
        35                  40                  45

Ser Cys Ile Asp Ser Cys Cys Trp Phe Ile Gly Cys Val Cys Val Thr
    50                  55                  60

Trp Trp Phe Leu Leu Phe Leu Tyr Asn Ala Met Pro Ala Ser Phe Pro
65                  70                  75                  80

Gln Tyr Val Thr Glu Arg Ile Thr Gly Pro Leu Pro Asp Pro Pro Gly
                85                  90                  95

Val Lys Leu Lys Lys Glu Gly Leu Lys Ala Lys His Pro Val Val Phe
            100                 105                 110

Ile Pro Gly Ile Val Thr Gly Gly Leu Glu Leu Trp Glu Gly Lys Gln
            115                 120                 125

Cys Ala Asp Gly Leu Phe Arg Lys Arg Leu Trp Gly Gly Thr Phe Gly
        130                 135                 140

Glu Val Tyr Lys Arg Pro Leu Cys Trp Val Glu His Met Ser Leu Asp
145                 150                 155                 160

Asn Glu Thr Gly Leu Asp Pro Ala Gly Ile Arg Val Arg Ala Val Ser
                165                 170                 175

Gly Leu Val Ala Ala Asp Tyr Phe Ala Pro Gly Tyr Phe Val Trp Ala
            180                 185                 190

Val Leu Ile Ala Asn Leu Ala His Ile Gly Tyr Glu Glu Lys Asn Met
            195                 200                 205

Tyr Met Ala Ala Tyr Asp Trp Arg Leu Ser Phe Gln Asn Thr Glu Val
        210                 215                 220

Arg Asp Gln Thr Leu Ser Arg Met Lys Ser Asn Ile Glu Leu Met Val
225                 230                 235                 240

Ser Thr Asn Gly Gly Lys Lys Ala Val Ile Val Pro His Ser Met Gly
                245                 250                 255

Val Leu Tyr Phe Leu His Phe Met Lys Trp Val Glu Ala Pro Ala Pro
            260                 265                 270

Leu Gly Gly Gly Gly Pro Asp Trp Cys Ala Lys Tyr Ile Lys Ala
        275                 280                 285

Val Met Asn Ile Gly Gly Pro Phe Leu Gly Val Pro Lys Ala Val Ala
        290                 295                 300

Gly Leu Phe Ser Ala Glu Ala Lys Asp Val Ala Val Ala Arg Ala Ile
305                 310                 315                 320

Ala Pro Gly Phe Leu Asp Thr Asp Ile Phe Arg Leu Gln Thr Leu Gln
                325                 330                 335
```

His Val Met Arg Met Thr Arg Thr Trp Asp Ser Thr Met Ser Met Leu
            340                 345                 350

Pro Lys Gly Gly Asp Thr Ile Trp Gly Gly Leu Asp Trp Ser Pro Glu
        355                 360                 365

Lys Gly His Thr Cys Cys Gly Lys Lys Gln Lys Asn Asn Glu Thr Cys
370                 375                 380

Gly Glu Ala Gly Glu Asn Gly Val Ser Lys Lys Ser Pro Val Asn Tyr
385                 390                 395                 400

Gly Arg Met Ile Ser Phe Gly Lys Glu Val Ala Glu Ala Ala Pro Ser
                405                 410                 415

Glu Ile Asn Asn Ile Asp Phe Arg Gly Ala Val Lys Gly Gln Ser Ile
            420                 425                 430

Pro Asn His Thr Cys Arg Asp Val Trp Thr Glu Tyr His Asp Met Gly
        435                 440                 445

Ile Ala Gly Ile Lys Ala Ile Ala Glu Tyr Lys Val Tyr Thr Ala Gly
    450                 455                 460

Glu Ala Ile Asp Leu Leu His Tyr Val Ala Pro Lys Met Met Ala Arg
465                 470                 475                 480

Gly Ala Ala His Phe Ser Tyr Gly Ile Ala Asp Asp Leu Asp Asp Thr
                485                 490                 495

Lys Tyr Gln Asp Pro Lys Tyr Trp Ser Asn Pro Leu Glu Thr Lys Leu
            500                 505                 510

Pro Asn Ala Pro Glu Met Glu Ile Tyr Ser Leu Tyr Gly Val Gly Ile
        515                 520                 525

Pro Thr Glu Arg Ala Tyr Val Tyr Lys Leu Asn Gln Ser Pro Asp Ser
    530                 535                 540

Cys Ile Pro Phe Gln Ile Phe Thr Ser Ala His Glu Glu Asp Glu Asp
545                 550                 555                 560

Ser Cys Leu Lys Ala Gly Val Tyr Asn Val Asp Gly Asp Glu Thr Val
                565                 570                 575

Pro Val Leu Ser Ala Gly Tyr Met Cys Ala Lys Ala Trp Arg Gly Lys
            580                 585                 590

Thr Arg Phe Asn Pro Ser Gly Ile Lys Thr Tyr Ile Arg Glu Tyr Asn
        595                 600                 605

His Ser Pro Pro Ala Asn Leu Leu Glu Gly Arg Gly Thr Gln Ser Gly
    610                 615                 620

Ala His Val Asp Ile Met Gly Asn Phe Ala Leu Ile Glu Asp Ile Met
625                 630                 635                 640

Arg Val Ala Ala Gly Gly Asn Gly Ser Asp Ile Gly His Asp Gln Val
                645                 650                 655

His Ser Gly Ile Phe Glu Trp Ser Glu Arg Ile Asp Leu Lys Leu
            660                 665                 670

<210> SEQ ID NO 17
<211> LENGTH: 546
<212> TYPE: PRT
<213> ORGANISM: Laccaria bicolor S238N-H82

<400> SEQUENCE: 17

Asp Gly Arg Glu Phe Gln Val Gly Glu Ala Met Lys Ala Arg Gly Leu
1               5                   10                  15

Thr Ala Gln His Pro Val Val Ile Ile Pro Gly Ile Val Ser Thr Gly
            20                  25                  30

Leu Glu Ser Trp Ser Thr Ser Pro Asp Tyr Arg Ala Phe Phe Arg Glu

```
            35                  40                  45
Lys Leu Trp Gly Ala Phe Asn Met Leu Ser Gln Val Thr Phe Asn Lys
 50                  55                  60

Glu Lys Trp Ile Ala Ala Met Met Leu Asp Pro Leu Thr Gly Leu Asp
 65                  70                  75                  80

Pro Pro Gly Ala Lys Val Arg Ala Ala Glu Gly Ile Asp Ala Ala Ser
                 85                  90                  95

Ser Phe Ile Gln Gly Phe Trp Ile Trp Ser Lys Val Val Glu Asn Leu
                100                 105                 110

Ala Val Val Asn Tyr Asp Thr Asn Asn Leu Tyr Leu Ala Pro Tyr Asp
                115                 120                 125

Trp Arg Leu Ser Tyr Tyr Asn Leu Glu Val Arg Asp Gly Tyr Phe Ser
                130                 135                 140

Arg Leu Lys Ser Thr Ile Glu Gly Leu Lys Lys Arg Gln Asn Lys Lys
145                 150                 155                 160

Val Val Ile Ala Ala His Ser Met Gly Ser Thr Val Arg His Arg His
                165                 170                 175

Leu Tyr Thr Tyr Glu Thr Phe Lys Trp Val Glu Ser Pro Leu His Gly
                180                 185                 190

Asn Gly Gly Ile Asp Trp Val Glu Asn His Ile Glu Ser Tyr Ile Ser
                195                 200                 205

Ile Ala Gly Thr His Leu Ala Lys Ala Met Ser Ala Phe Leu Ser Gly
                210                 215                 220

Glu Met Lys Asp Thr Val Gln Met Asn Pro Ala Gly Ala Tyr Val Leu
225                 230                 235                 240

Glu Arg Phe Phe Ser Arg Lys Glu Arg Gln Arg Leu Phe Arg Ser Trp
                245                 250                 255

Ala Gly Ser Ala Ser Met Trp Leu Lys Gly Gly Asn Ala Val Trp Gly
                260                 265                 270

Ser Ala Leu His Ala Pro Asp Asp Ala Cys Asn Asn Thr His Thr His
                275                 280                 285

Gly Glu Leu Ile Ala Phe Arg Ser Leu Ser Pro Gln Ser Asn Gly Asp
                290                 295                 300

Thr Thr Arg Asn Met Thr Ala Glu Glu Ala Gly Leu Trp Ile Leu Gln
305                 310                 315                 320

His Thr Pro Thr Ala Phe Gln Lys Met Leu Glu Thr Asn Tyr Ser Tyr
                325                 330                 335

Gly Ile Glu Arg Asp Glu Glu Gln Leu Ser Arg Asn Asp Leu Asp His
                340                 345                 350

Arg Lys Trp Thr Asn Pro Leu Glu Arg Phe Gln Leu Leu Pro Arg Ala
                355                 360                 365

Pro Ser Met Lys Ile Tyr Cys Val Tyr Gly His Gly Lys Glu Thr Glu
                370                 375                 380

Arg Ser Tyr Trp Tyr Val Gln Gly Lys Asp Ser Glu Ala Ala Asp Ala
385                 390                 395                 400

Val Asp Thr Glu Cys Thr Asp Pro His Ser Ser Glu Cys Gly Val Leu
                405                 410                 415

Ser Gln His Leu Gly Pro Pro Ser Leu Arg Glu Ser Trp Ile Asp Ser
                420                 425                 430

Asp Tyr Thr Asn Asn Ser Ala Phe Pro Lys Leu Leu Asn Gly Val Lys
                435                 440                 445

Met Gly Glu Gly Asp Gly Thr Val Ser Leu Val Ser Leu Gly Ala Met
450                 455                 460
```

```
Cys Val Glu Gly Trp Lys Arg Pro Arg Trp Asn Pro Ala Gly Ile Lys
465                 470                 475                 480

Ile Thr Thr Val Glu Leu Pro His Arg Pro Thr Val Thr Met Pro Arg
                485                 490                 495

Gly Gly Ala Asn Thr Ser Asp His Val Asp Ile Leu Gly Ser Thr Gly
            500                 505                 510

Leu Asn Glu Val Ile Leu Lys Val Ala Thr Gly Val Gly His Glu Val
            515                 520                 525

Thr Asp Asn Tyr Val Ser Asp Ile Gln Arg Tyr Ala Gln Arg Ile Gln
            530                 535                 540

Trp Asp
545

<210> SEQ ID NO 18
<211> LENGTH: 680
<212> TYPE: PRT
<213> ORGANISM: Scheffersomyces stipitis CBS 6054

<400> SEQUENCE: 18

Met Ser Asn Leu Ser Asn Arg Arg Ser Lys Ser Glu Asp Ser Leu
1               5                   10                  15

Asp Val Ser Glu Gly Ala Ala Lys Ala Ser Gly Val Ala Tyr Leu Gly
                20                  25                  30

Lys Val Phe Ser Ala His Thr Thr Gly Pro Asp Gly Gln Glu Gly His
                35                  40                  45

His Ile His Gln His Ile Gly Lys Pro Ser Ser Ile Glu Glu Lys Asp
            50                  55                  60

Thr Pro Arg Pro Pro Ile Ile Ser Thr Ser Ser Ser Ser Ser Thr Ser
65                  70                  75                  80

Ser Lys Ser Lys Arg Lys Phe His Glu Lys Arg Arg Val Val Phe Ile
                85                  90                  95

Phe Gly Ala Phe Leu Gly Leu Phe Leu Thr Ile Gly Tyr Ser Thr Tyr
                100                 105                 110

Tyr Asn Pro Ser Ile Lys Asn Glu Ile Asp Lys Ile Val Arg Ile Asp
                115                 120                 125

Arg Phe Asn Asp Phe Phe Glu Asp Trp Lys Asp Trp Lys Asp Ile Leu
            130                 135                 140

Pro Val Gly Leu Gln Ser Ile Leu Ser Glu Gln Leu Gly Gln Lys Asp
145                 150                 155                 160

Asp Ala Leu Gln Tyr Ser Pro Asp Ser Phe Ser Val Gly Arg Arg Leu
                165                 170                 175

Ala Ala Thr Met Asn Leu Thr Ser Glu Tyr Asn Val Leu Leu Val Pro
                180                 185                 190

Gly Val Ile Ser Thr Gly Ile Glu Ser Trp Gly Val Ser Thr Glu Gly
                195                 200                 205

Asp Cys Pro Ser Ile Ser His Phe Arg Lys Arg Leu Trp Gly Ser Phe
            210                 215                 220

Tyr Met Leu Arg Thr Met Val Leu Asp Lys Lys Cys Trp Leu Lys His
225                 230                 235                 240

Ile Met Leu Asp Pro Val Thr Gly Leu Asp Pro His Asn Ile Lys Met
                245                 250                 255

Arg Ala Ala Gln Gly Phe Glu Ala Ala Asp Tyr Phe Met Val Gly Tyr
                260                 265                 270

Trp Ile Trp Asn Lys Ile Leu Gln Asn Leu Ala Val Ile Gly Tyr Gly
```

```
            275                 280                 285
Pro Asn Thr Met Gln Val Ala Ser Tyr Asp Trp Arg Leu Ala Phe Leu
290                 295                 300

Asp Leu Glu Lys Arg Asp Gly Tyr Phe Ser Lys Ile Lys Ser Gln Ile
305                 310                 315                 320

Glu Val Thr Lys Asn Leu Asn Gly Lys Lys Ser Ile Ile Val Gly His
                325                 330                 335

Ser Met Gly Ala Gln Ile Ser Tyr Tyr Phe Leu Lys Trp Val Glu Ala
            340                 345                 350

Glu Asn Tyr Gly Gly Gly Pro Asn Trp Val Asn Asp His Ile Glu
        355                 360                 365

Ala Phe Val Asp Ile Ser Gly Ser Thr Leu Gly Thr Pro Lys Thr Ile
370                 375                 380

Pro Ala Leu Leu Ser Gly Glu Met Lys Asp Thr Val Gln Leu Asn Ala
385                 390                 395                 400

Leu Ala Val Tyr Gly Leu Glu Gln Phe Phe Ser Arg Lys Glu Arg Val
                405                 410                 415

Asp Leu Leu Arg Thr Phe Gly Gly Ile Ala Gly Met Leu Pro Lys Gly
            420                 425                 430

Gly Ser Thr Ile Trp Gly Asp Leu Glu Arg Ala Pro Asp Asp Ile
        435                 440                 445

Ser Asp Tyr Ser Glu Asp Val Glu Gly Ala Ile Lys Lys Asn Asn Asp
450                 455                 460

Ser Phe Gly Asn Phe Ile Arg His Lys Lys Asp Gly Thr Val Ser
465                 470                 475                 480

Asn Phe Thr Ile Glu Gln Ser Ile Asp Met Leu Leu Asp Glu Ser Pro
                485                 490                 495

Asn Trp Tyr Lys Glu Arg Val Glu His Gln Tyr Ser Tyr Gly Ile Ala
            500                 505                 510

Lys Thr Lys Glu Glu Leu Glu Arg Asn Asn Lys Asp His Ser Lys Phe
        515                 520                 525

Ser Asn Pro Leu Glu Ala Ala Leu Pro Asn Ala Pro Asp Met Lys Ile
530                 535                 540

Phe Cys Phe Tyr Gly Val Gly Lys Pro Thr Glu Arg Ala Tyr Asn Tyr
545                 550                 555                 560

Val Asp Ala Asp Ser Gln Thr Gly Leu His Lys Val Ile Asp Pro Asp
                565                 570                 575

Ala Glu Thr Pro Val Tyr Leu Gly Asp Gly Asp Gly Thr Val Ser Leu
            580                 585                 590

Leu Ala His Thr Met Cys His Glu Trp Lys Lys Gly Ser Glu Ser Arg
        595                 600                 605

Tyr Asn Pro Ser Gly Ile Pro Val Thr Ile Val Glu Ile Met Asn Glu
610                 615                 620

Pro Asp Arg Tyr Asp Ile Arg Gly Gly Ala Lys Thr Ala Asp His Val
625                 630                 635                 640

Asp Ile Leu Gly Ser Ala Glu Leu Asn Glu Leu Val Leu Arg Val Ala
                645                 650                 655

Ala Gly Val Gly Asp Gly Ile Glu Asp His Tyr Val Ser Asn Leu Arg
            660                 665                 670

Tyr Ile Ala Glu Lys Met Ala Ile
        675                 680

<210> SEQ ID NO 19
```

<211> LENGTH: 504
<212> TYPE: PRT
<213> ORGANISM: Homo sapiens

<400> SEQUENCE: 19

```
Met Phe Pro Arg Glu Lys Thr Trp Asn Ile Ser Phe Ala Gly Cys Gly
1               5                   10                  15

Phe Leu Gly Val Tyr Tyr Val Gly Val Ala Ser Cys Leu Arg Glu His
            20                  25                  30

Ala Pro Phe Leu Val Ala Asn Ala Thr His Ile Tyr Gly Ala Ser Ala
        35                  40                  45

Gly Ala Leu Thr Ala Thr Ala Leu Val Thr Gly Val Cys Leu Gly Glu
    50                  55                  60

Ala Gly Ala Lys Phe Ile Glu Val Ser Lys Glu Ala Arg Lys Arg Phe
65                  70                  75                  80

Leu Gly Pro Leu His Pro Ser Phe Asn Leu Val Lys Ile Ile Arg Ser
                85                  90                  95

Phe Leu Leu Lys Val Leu Pro Ala Asp Ser His Glu His Ala Ser Gly
            100                 105                 110

Arg Leu Gly Ile Ser Leu Thr Arg Val Ser Asp Gly Glu Asn Val Ile
        115                 120                 125

Ile Ser His Phe Asn Ser Lys Asp Glu Leu Ile Gln Ala Asn Val Cys
    130                 135                 140

Ser Gly Phe Ile Pro Val Tyr Cys Gly Leu Ile Pro Pro Ser Leu Gln
145                 150                 155                 160

Gly Val Arg Tyr Val Asp Gly Gly Ile Ser Asp Asn Leu Pro Leu Tyr
                165                 170                 175

Glu Leu Lys Asn Thr Ile Thr Val Ser Pro Phe Ser Gly Glu Ser Asp
            180                 185                 190

Ile Cys Pro Gln Asp Ser Ser Thr Asn Ile His Glu Leu Arg Val Thr
        195                 200                 205

Asn Thr Ser Ile Gln Phe Asn Leu Arg Asn Leu Tyr Arg Leu Ser Lys
    210                 215                 220

Ala Leu Phe Pro Pro Glu Pro Leu Val Leu Arg Glu Met Cys Lys Gln
225                 230                 235                 240

Gly Tyr Arg Asp Gly Leu Arg Phe Leu Gln Arg Asn Gly Leu Leu Asn
                245                 250                 255

Arg Pro Asn Pro Leu Leu Ala Leu Pro Pro Ala Arg Pro His Gly Pro
            260                 265                 270

Glu Asp Lys Asp Gln Ala Val Glu Ser Ala Gln Ala Glu Asp Tyr Ser
        275                 280                 285

Gln Leu Pro Gly Glu Asp His Val Leu Glu His Leu Pro Ala Arg Leu
    290                 295                 300

Asn Glu Ala Leu Leu Glu Ala Cys Val Glu Pro Thr Asp Leu Leu Thr
305                 310                 315                 320

Thr Leu Ser Asn Met Leu Pro Val Arg Leu Ala Thr Ala Met Met Val
                325                 330                 335

Pro Tyr Thr Leu Pro Leu Glu Ser Ala Leu Ser Phe Thr Ile Cys Leu
            340                 345                 350

Leu Glu Trp Leu Pro Asp Val Pro Glu Asp Ile Arg Trp Met Lys Glu
        355                 360                 365

Gln Thr Gly Ser Ile Cys Gln Tyr Leu Val Met Arg Ala Lys Arg Lys
    370                 375                 380

Leu Gly Arg His Leu Pro Ser Arg Leu Pro Glu Gln Val Glu Leu Arg
```

```
             385                 390                 395                 400
Arg Val Gln Ser Leu Pro Ser Val Pro Leu Ser Cys Ala Ala Tyr Arg
                405                 410                 415

Glu Ala Pro Pro Gly Trp Met Arg Asn Asn Leu Ser Leu Gly Asp Ala
                420                 425                 430

Leu Ala Lys Trp Glu Glu Cys Gln Arg Gln Leu Leu Leu Gly Leu Phe
                435                 440                 445

Cys Thr Asn Val Ala Phe Pro Pro Glu Ala Leu Arg Met Arg Ala Pro
                450                 455                 460

Ala Asp Pro Ala Pro Ala Pro Ala Asp Pro Ala Ser Pro Gln His Gln
465                 470                 475                 480

Leu Ala Gly Pro Ala Pro Leu Leu Ser Thr Pro Ala Pro Glu Ala Arg
                485                 490                 495

Pro Val Ile Gly Ala Leu Gly Leu
                500

<210> SEQ ID NO 20
<211> LENGTH: 486
<212> TYPE: PRT
<213> ORGANISM: Mus musculus

<400> SEQUENCE: 20

Met Phe Pro Arg Glu Thr Lys Trp Asn Ile Ser Phe Ala Gly Cys Gly
1               5                   10                  15

Phe Leu Gly Val Tyr His Ile Gly Val Ala Ser Cys Leu Arg Glu His
                20                  25                  30

Ala Pro Phe Leu Val Ala Asn Ala Thr His Ile Tyr Gly Ala Ser Ala
            35                  40                  45

Gly Ala Leu Thr Ala Thr Ala Leu Val Thr Gly Ala Cys Leu Gly Glu
        50                  55                  60

Ala Gly Ala Asn Ile Ile Glu Val Ser Lys Glu Ala Arg Lys Arg Phe
65                  70                  75                  80

Leu Gly Pro Leu His Pro Ser Phe Asn Leu Val Lys Thr Ile Arg Gly
                85                  90                  95

Cys Leu Leu Lys Thr Leu Pro Ala Asp Cys His Glu Arg Ala Asn Gly
                100                 105                 110

Arg Leu Gly Ile Ser Leu Thr Arg Val Ser Asp Gly Glu Asn Val Ile
            115                 120                 125

Ile Ser His Phe Ser Ser Lys Asp Glu Leu Ile Gln Ala Asn Val Cys
        130                 135                 140

Ser Thr Phe Ile Pro Val Tyr Cys Gly Leu Ile Pro Pro Thr Leu Gln
145                 150                 155                 160

Gly Val Arg Tyr Val Asp Gly Gly Ile Ser Asp Asn Leu Pro Leu Tyr
                165                 170                 175

Glu Leu Lys Asn Thr Ile Thr Val Ser Pro Phe Ser Gly Glu Ser Asp
                180                 185                 190

Ile Cys Pro Gln Asp Ser Ser Thr Asn Ile His Glu Leu Arg Val Thr
            195                 200                 205

Asn Thr Ser Ile Gln Phe Asn Leu Arg Asn Leu Tyr Arg Leu Ser Lys
        210                 215                 220

Ala Leu Phe Pro Pro Glu Pro Met Val Leu Arg Glu Met Cys Lys Gln
225                 230                 235                 240

Gly Tyr Arg Asp Gly Leu Arg Phe Leu Arg Arg Asn Gly Leu Leu Asn
                245                 250                 255
```

```
Gln Pro Asn Pro Leu Leu Ala Leu Pro Pro Val Pro Gln Glu Glu
                260                 265                 270

Asp Ala Glu Glu Ala Ala Val Val Glu Arg Ala Gly Glu Asp
            275                 280                 285

Gln Leu Gln Pro Tyr Arg Lys Asp Arg Ile Leu Glu His Leu Pro Ala
        290                 295                 300

Arg Leu Asn Glu Ala Leu Leu Glu Ala Cys Val Glu Pro Lys Asp Leu
305                 310                 315                 320

Met Thr Thr Leu Ser Asn Met Leu Pro Val Arg Leu Ala Thr Ala Met
                325                 330                 335

Met Val Pro Tyr Thr Leu Pro Leu Glu Ser Ala Val Ser Phe Thr Ile
            340                 345                 350

Arg Leu Leu Glu Trp Leu Pro Asp Val Pro Glu Asp Ile Arg Trp Met
        355                 360                 365

Lys Glu Gln Thr Gly Ser Ile Cys Gln Tyr Leu Val Met Arg Ala Lys
370                 375                 380

Arg Lys Leu Gly Asp His Leu Pro Ser Arg Leu Ser Glu Gln Val Glu
385                 390                 395                 400

Leu Arg Arg Ala Gln Ser Leu Pro Ser Val Pro Leu Ser Cys Ala Thr
                405                 410                 415

Tyr Ser Glu Ala Leu Pro Asn Trp Val Arg Asn Asn Leu Ser Leu Gly
            420                 425                 430

Asp Ala Leu Ala Lys Trp Glu Glu Cys Gln Arg Gln Leu Leu Leu Gly
        435                 440                 445

Leu Phe Cys Thr Asn Val Ala Phe Pro Pro Asp Ala Leu Arg Met Arg
450                 455                 460

Ala Pro Ala Ser Pro Thr Ala Ala Asp Pro Ala Thr Pro Gln Asp Pro
465                 470                 475                 480

Pro Gly Leu Pro Pro Cys
                485

<210> SEQ ID NO 21
<211> LENGTH: 219
<212> TYPE: PRT
<213> ORGANISM: Homo sapiens

<400> SEQUENCE: 21

Met Glu Ala Ala Arg Asp Tyr Ala Gly Ala Leu Ile Arg Pro Leu Thr
1               5                   10                  15

Phe Met Gly Ser Gln Thr Lys Arg Val Leu Phe Thr Pro Leu Met His
                20                  25                  30

Pro Ala Arg Pro Phe Arg Val Ser Asn His Asp Arg Ser Ser Arg Arg
            35                  40                  45

Gly Val Met Ala Ser Ser Leu Gln Glu Leu Ile Ser Lys Thr Leu Asp
        50                  55                  60

Ala Leu Val Ile Ala Thr Gly Leu Val Thr Leu Val Leu Glu Glu Asp
65                  70                  75                  80

Gly Thr Val Val Asp Thr Glu Glu Phe Phe Gln Thr Leu Gly Asp Asn
                85                  90                  95

Thr His Phe Met Ile Leu Glu Lys Gly Gln Lys Trp Met Pro Gly Ser
                100                 105                 110

Gln His Phe Pro Thr Cys Ser Pro Pro Lys Arg Ser Gly Ile Ala Arg
            115                 120                 125

Val Thr Phe Asp Leu Tyr Arg Leu Asn Pro Lys Asp Phe Ile Gly Cys
        130                 135                 140
```

Leu Asn Val Lys Ala Thr Met Tyr Glu Met Tyr Ser Val Ser Tyr Asp
145                 150                 155                 160

Ile Arg Cys Thr Gly Leu Lys Gly Leu Leu Arg Ser Leu Leu Arg Phe
                165                 170                 175

Leu Ser Tyr Ser Ala Gln Val Thr Gly Gln Phe Leu Ile Tyr Leu Gly
            180                 185                 190

Thr Tyr Met Leu Arg Val Leu Asp Asp Lys Glu Glu Arg Pro Ser Leu
        195                 200                 205

Arg Ser Gln Ala Lys Gly Arg Phe Thr Cys Gly
    210                 215

<210> SEQ ID NO 22
<211> LENGTH: 217
<212> TYPE: PRT
<213> ORGANISM: Mus musculus

<400> SEQUENCE: 22

Met Glu Thr Ala Arg Asp Tyr Ala Gly Ala Leu Ile Arg Pro Leu Thr
1               5                   10                  15

Phe Met Gly Leu Gln Thr Lys Lys Val Leu Leu Thr Pro Leu Ile His
                20                  25                  30

Pro Ala Arg Pro Phe Arg Val Ser Asn His Asp Arg Ser Ser Arg Arg
            35                  40                  45

Gly Val Met Ala Ser Ser Leu Gln Glu Leu Ile Ser Lys Thr Leu Asp
        50                  55                  60

Val Leu Val Ile Thr Thr Gly Leu Val Thr Leu Val Leu Glu Glu Asp
65                  70                  75                  80

Gly Thr Val Val Asp Thr Glu Glu Phe Phe Gln Thr Leu Arg Asp Asn
                85                  90                  95

Thr His Phe Met Ile Leu Glu Lys Gly Gln Lys Trp Thr Pro Gly Ser
                100                 105                 110

Lys Tyr Val Pro Val Cys Lys Gln Pro Lys Lys Ser Gly Ile Ala Arg
            115                 120                 125

Val Thr Phe Asp Leu Tyr Arg Leu Asn Pro Lys Asp Phe Leu Gly Cys
        130                 135                 140

Leu Asn Val Lys Ala Thr Met Tyr Glu Met Tyr Ser Val Ser Tyr Asp
145                 150                 155                 160

Ile Arg Cys Thr Ser Phe Lys Ala Val Leu Arg Asn Leu Leu Arg Phe
                165                 170                 175

Met Ser Tyr Ala Ala Gln Met Thr Gly Gln Phe Leu Val Tyr Ala Gly
            180                 185                 190

Thr Tyr Met Leu Arg Val Leu Gly Asp Thr Glu Glu Gln Pro Ser Pro
        195                 200                 205

Lys Pro Ser Thr Lys Gly Trp Phe Met
    210                 215

<210> SEQ ID NO 23
<211> LENGTH: 430
<212> TYPE: PRT
<213> ORGANISM: Arabidopsis thaliana

<400> SEQUENCE: 23

Met Lys Lys Arg Leu Thr Thr Ser Thr Cys Ser Ser Ser Pro Ser Ser
1               5                   10                  15

Ser Val Ser Ser Ser Thr Thr Thr Ser Ser Pro Ile Gln Ser Glu Ala
                20                  25                  30

Pro Arg Pro Lys Arg Ala Lys Arg Ala Lys Lys Ser Ser Pro Ser Gly
                35                  40                  45

Asp Lys Ser His Asn Pro Thr Ser Pro Ala Ser Thr Arg Arg Ser Ser
 50                  55                  60

Ile Tyr Arg Gly Val Thr Arg His Arg Trp Thr Gly Arg Phe Glu Ala
 65                  70                  75                  80

His Leu Trp Asp Lys Ser Ser Trp Asn Ser Ile Gln Asn Lys Lys Gly
                 85                  90                  95

Lys Gln Val Tyr Leu Gly Ala Tyr Asp Ser Glu Glu Ala Ala Ala His
                100                 105                 110

Thr Tyr Asp Leu Ala Ala Leu Lys Tyr Trp Gly Pro Asp Thr Ile Leu
                115                 120                 125

Asn Phe Pro Ala Glu Thr Tyr Thr Lys Glu Leu Glu Glu Met Gln Arg
                130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
                180                 185                 190

Leu Tyr Leu Gly Thr Tyr Asn Thr Gln Glu Glu Ala Ala Ala Ala Tyr
                195                 200                 205

Asp Met Ala Ala Ile Glu Tyr Arg Gly Ala Asn Ala Val Thr Asn Phe
                210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
                260                 265                 270

Val Lys Gln Gln Tyr Val Glu Glu Pro Pro Gln Glu Glu Glu Glu Lys
                275                 280                 285

Glu Glu Glu Lys Ala Glu Gln Gln Glu Ala Glu Ile Val Gly Tyr Ser
                290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
                340                 345                 350

Asn Glu Asn Pro Ile Glu Tyr Pro Glu Leu Phe Asn Glu Leu Ala Phe
                355                 360                 365

Glu Asp Asn Ile Asp Phe Met Phe Asp Asp Gly Lys His Glu Cys Leu
                370                 375                 380

Asn Leu Glu Asn Leu Asp Cys Cys Val Val Gly Arg Glu Ser Pro Pro
385                 390                 395                 400

Ser Ser Ser Ser Pro Leu Ser Cys Leu Ser Thr Asp Ser Ala Ser Ser
                405                 410                 415

Thr Thr Thr Thr Thr Thr Ser Val Ser Cys Asn Tyr Leu Val
                420                 425                 430

<210> SEQ ID NO 24
<211> LENGTH: 239

<212> TYPE: PRT
<213> ORGANISM: Danio rerio

<400> SEQUENCE: 24

Met Glu Asn Ala Lys Lys Ser Val Asp Val Leu Ser Thr Ser Leu Ser
1               5                   10                  15

Lys Cys Ile Ser Ala Cys Gly Ser Val Thr His Gln Ile Leu Pro Arg
            20                  25                  30

Trp Thr Gln His Ser Arg Pro Phe Arg Val Ile Asn Ser Asp Arg Ser
        35                  40                  45

Ile Lys Lys Gly Ile Met Ala Asp Asp Leu Glu Asp Leu His His Lys
    50                  55                  60

Val Met Asp Val Phe His Ile His Cys Ile Ser Ala Leu Val Leu Asp
65                  70                  75                  80

Glu Asp Gly Thr Gly Ile Asp Thr Gln Asp Phe Phe Gln Thr Leu Lys
                85                  90                  95

Asp Asn Thr Val Leu Met Val Leu Gly Lys Gly Gln Lys Trp Ala Pro
            100                 105                 110

Gln Thr Lys His Leu Pro Gly Gln Lys Lys Val Glu Arg Lys Arg Met
        115                 120                 125

Thr Lys Lys Asp Pro Asp Cys Asn Trp Thr Gln Pro Arg Lys Asp Val
    130                 135                 140

Ala Lys Leu Thr Phe Asp Leu Tyr Lys Lys His Pro Gln Asp Phe Ile
145                 150                 155                 160

Gly Cys Leu Asn Val Gln Ala Thr Leu Tyr Gly Met Tyr Ser Val Ser
                165                 170                 175

Tyr Val Leu His Cys Tyr Lys Ala Lys Arg Met Leu Arg Glu Ala Leu
            180                 185                 190

Arg Trp Thr Leu Phe Thr Met Gln Thr Thr Gly His Val Leu Val Gly
        195                 200                 205

Thr Ser Cys Tyr Ile Gln His Leu Ile Asp Glu Glu Lys Thr Glu
    210                 215                 220

Thr Glu Met Ile Thr Pro Ala Tyr Val Ile Lys Gln Leu Lys His
225                 230                 235

<210> SEQ ID NO 25
<211> LENGTH: 283
<212> TYPE: PRT
<213> ORGANISM: Homo sapiens

<400> SEQUENCE: 25

Met Asp Leu Trp Pro Gly Ala Trp Met Leu Leu Leu Leu Phe Leu
1               5                   10                  15

Leu Leu Leu Phe Leu Leu Pro Thr Leu Trp Phe Cys Ser Pro Ser Ala
            20                  25                  30

Lys Tyr Phe Phe Lys Met Ala Phe Tyr Asn Gly Trp Ile Leu Phe Leu
        35                  40                  45

Ala Val Leu Ala Ile Pro Val Cys Ala Val Arg Gly Arg Asn Val Glu
    50                  55                  60

Asn Met Lys Ile Leu Arg Leu Met Leu His Ile Lys Tyr Leu Tyr
65                  70                  75                  80

Gly Ile Arg Val Glu Val Arg Gly Ala His His Phe Pro Pro Ser Gln
                85                  90                  95

Pro Tyr Val Val Val Ser Asn His Gln Ser Ser Leu Asp Leu Leu Gly
            100                 105                 110

```
Met Met Glu Val Leu Pro Gly Arg Cys Val Pro Ile Ala Lys Arg Glu
            115                 120                 125

Leu Leu Trp Ala Gly Ser Ala Gly Leu Ala Cys Trp Leu Ala Gly Val
    130                 135                 140

Ile Phe Ile Asp Arg Lys Arg Thr Gly Asp Ala Ile Ser Val Met Ser
145                 150                 155                 160

Glu Val Ala Gln Thr Leu Leu Thr Gln Asp Val Arg Val Trp Val Phe
                165                 170                 175

Pro Glu Gly Thr Arg Asn His Asn Gly Ser Met Leu Pro Phe Lys Arg
                180                 185                 190

Gly Ala Phe His Leu Ala Val Gln Ala Gln Val Pro Ile Val Pro Ile
                195                 200                 205

Val Met Ser Ser Tyr Gln Asp Phe Tyr Cys Lys Lys Glu Arg Arg Phe
    210                 215                 220

Thr Ser Gly Gln Cys Gln Val Arg Val Leu Pro Pro Val Pro Thr Glu
225                 230                 235                 240

Gly Leu Thr Pro Asp Asp Val Pro Ala Leu Ala Asp Arg Val Arg His
                245                 250                 255

Ser Met Leu Thr Val Phe Arg Glu Ile Ser Thr Asp Gly Arg Gly Gly
                260                 265                 270

Gly Asp Tyr Leu Lys Lys Pro Gly Gly Gly Gly
        275                 280

<210> SEQ ID NO 26
<211> LENGTH: 285
<212> TYPE: PRT
<213> ORGANISM: Mus musculus

<400> SEQUENCE: 26

Met Glu Leu Trp Pro Gly Ala Trp Thr Ala Leu Leu Leu Leu Leu Leu
1               5                   10                  15

Leu Leu Leu Ser Thr Leu Trp Phe Cys Ser Ser Ser Ala Lys Tyr Phe
                20                  25                  30

Phe Lys Met Ala Phe Tyr Asn Gly Trp Ile Leu Phe Leu Ala Ile Leu
            35                  40                  45

Ala Ile Pro Val Cys Ala Val Arg Gly Arg Asn Val Glu Asn Met Lys
        50                  55                  60

Ile Leu Arg Leu Leu Leu His Val Lys Tyr Leu Tyr Gly Ile Arg
65                  70                  75                  80

Val Glu Val Arg Gly Ala His His Phe Pro Pro Thr Gln Pro Tyr Val
                85                  90                  95

Val Val Ser Asn His Gln Ser Ser Leu Asp Leu Leu Gly Met Met Glu
                100                 105                 110

Val Leu Pro Asp Arg Cys Val Pro Ile Ala Lys Arg Glu Leu Leu Trp
            115                 120                 125

Ala Gly Ser Ala Gly Leu Ala Cys Trp Leu Ala Gly Ile Ile Phe Ile
        130                 135                 140

Asp Arg Lys Arg Thr Gly Asp Ala Ile Ser Val Met Ser Glu Val Ala
145                 150                 155                 160

Gln Thr Leu Leu Thr Gln Asp Val Arg Val Trp Val Phe Pro Glu Gly
                165                 170                 175

Thr Arg Asn His Asn Gly Ser Met Leu Pro Phe Lys Arg Gly Ala Phe
                180                 185                 190

His Leu Ala Val Gln Ala Gln Val Pro Ile Ile Pro Ile Val Met Ser
            195                 200                 205
```

```
Ser Tyr Gln Asp Phe Tyr Ser Lys Lys Glu Arg Arg Phe Thr Ser Pro
        210                 215                 220
Gly Arg Cys Gln Val Arg Val Leu Pro Pro Val Ser Thr Glu Gly Leu
225                 230                 235                 240
Thr Pro Asp Asp Val Pro Ala Leu Ala Asp Ser Val Arg His Ser Met
                245                 250                 255
Leu Thr Ile Phe Arg Glu Ile Ser Thr Asp Gly Leu Gly Gly Gly Asp
            260                 265                 270
Cys Leu Lys Lys Pro Gly Gly Ala Gly Glu Ala Arg Leu
            275                 280                 285

<210> SEQ ID NO 27
<211> LENGTH: 827
<212> TYPE: PRT
<213> ORGANISM: Mus musculus

<400> SEQUENCE: 27

Met Glu Glu Ser Ser Val Thr Val Gly Thr Ile Asp Val Ser Tyr Leu
1               5                   10                  15
Pro Ser Ser Ser Glu Tyr Ser Leu Gly Arg Cys Lys His Thr Ser Glu
                20                  25                  30
Asp Trp Val Asp Cys Gly Phe Lys Pro Thr Phe Phe Arg Ser Ala Thr
            35                  40                  45
Leu Lys Trp Lys Glu Ser Leu Met Ser Arg Lys Arg Pro Phe Val Gly
        50                  55                  60
Arg Cys Cys Tyr Ser Cys Thr Pro Gln Ser Trp Glu Arg Phe Phe Asn
65                  70                  75                  80
Pro Ser Ile Pro Ser Leu Gly Leu Arg Asn Val Ile Tyr Ile Asn Glu
                85                  90                  95
Thr His Thr Arg His Arg Gly Trp Leu Ala Arg Arg Leu Ser Tyr Ile
                100                 105                 110
Leu Phe Val Gln Glu Arg Asp Val His Lys Gly Met Phe Ala Thr Ser
            115                 120                 125
Val Thr Glu Asn Val Leu Ser Ser Ser Arg Val Gln Glu Ala Ile Ala
        130                 135                 140
Glu Val Ala Ala Glu Leu Asn Pro Asp Gly Ser Ala Gln Gln Gln Ser
145                 150                 155                 160
Lys Ala Ile Gln Lys Val Lys Arg Lys Ala Arg Lys Ile Leu Gln Glu
                165                 170                 175
Met Val Ala Thr Val Ser Pro Gly Met Ile Arg Leu Thr Gly Trp Val
            180                 185                 190
Leu Leu Lys Leu Phe Asn Ser Phe Phe Trp Asn Ile Gln Ile His Lys
        195                 200                 205
Gly Gln Leu Glu Met Val Lys Ala Ala Thr Glu Thr Asn Leu Pro Leu
210                 215                 220
Leu Phe Leu Pro Val His Arg Ser His Ile Asp Tyr Leu Leu Leu Thr
225                 230                 235                 240
Phe Ile Leu Phe Cys His Asn Ile Lys Ala Pro Tyr Ile Ala Ser Gly
                245                 250                 255
Asn Asn Leu Asn Ile Pro Val Phe Ser Thr Leu Ile His Lys Leu Gly
            260                 265                 270
Gly Phe Phe Ile Arg Arg Arg Leu Asp Glu Thr Pro Asp Gly Arg Lys
        275                 280                 285
Asp Ile Leu Tyr Arg Ala Leu Leu His Gly His Val Val Glu Leu Leu
```

```
            290                 295                 300
Arg Gln Gln Gln Phe Leu Glu Ile Phe Leu Glu Gly Thr Arg Ser Arg
305                 310                 315                 320

Ser Gly Lys Thr Ser Cys Ala Arg Ala Gly Leu Leu Ser Val Val Val
                325                 330                 335

Asp Thr Leu Ser Ser Asn Thr Ile Pro Asp Ile Leu Val Ile Pro Val
                340                 345                 350

Gly Ile Ser Tyr Asp Arg Ile Ile Glu Gly His Tyr Asn Gly Glu Gln
            355                 360                 365

Leu Gly Lys Pro Lys Asn Glu Ser Leu Trp Ser Val Ala Arg Gly
    370                 375                 380

Val Ile Arg Met Leu Arg Lys Asn Tyr Gly Tyr Val Arg Val Asp Phe
385                 390                 395                 400

Ala Gln Pro Phe Ser Leu Lys Glu Tyr Leu Glu Gly Gln Ser Gln Lys
                405                 410                 415

Pro Val Ser Ala Pro Leu Ser Leu Glu Gln Ala Leu Leu Pro Ala Ile
                420                 425                 430

Leu Pro Ser Arg Pro Asn Asp Val Ala Asp Glu His Gln Asp Leu Ser
            435                 440                 445

Ser Asn Glu Ser Arg Asn Pro Ala Asp Glu Ala Phe Arg Arg Leu
    450                 455                 460

Ile Ala Asn Leu Ala Glu His Ile Leu Phe Thr Ala Ser Lys Ser Cys
465                 470                 475                 480

Ala Ile Met Ser Thr His Ile Val Ala Cys Leu Leu Leu Tyr Arg His
                485                 490                 495

Arg Gln Gly Ile His Leu Ser Thr Leu Val Glu Asp Phe Phe Val Met
            500                 505                 510

Lys Glu Glu Val Leu Ala Arg Asp Phe Asp Leu Gly Phe Ser Gly Asn
                515                 520                 525

Ser Glu Asp Val Val Met His Ala Ile Gln Leu Leu Gly Asn Cys Val
            530                 535                 540

Thr Ile Thr His Thr Ser Arg Lys Asp Glu Phe Phe Ile Thr Pro Ser
545                 550                 555                 560

Thr Thr Val Pro Ser Val Phe Glu Leu Asn Phe Tyr Ser Asn Gly Val
                565                 570                 575

Leu His Val Phe Ile Met Glu Ala Ile Ile Ala Cys Ser Ile Tyr Ala
            580                 585                 590

Val Leu Asn Lys Arg Cys Ser Gly Gly Ser Ala Gly Gly Leu Gly Asn
                595                 600                 605

Leu Ile Ser Gln Glu Gln Leu Val Arg Lys Ala Ala Ser Leu Cys Tyr
        610                 615                 620

Leu Leu Ser Asn Glu Gly Thr Ile Ser Leu Pro Cys Gln Thr Phe Tyr
625                 630                 635                 640

Gln Val Cys His Glu Thr Val Gly Lys Phe Ile Gln Tyr Gly Ile Leu
                645                 650                 655

Thr Val Ala Glu Gln Asp Asp Gln Glu Asp Val Ser Pro Gly Leu Ala
                660                 665                 670

Glu Gln Gln Trp Asp Lys Lys Leu Pro Glu Leu Asn Trp Arg Ser Asp
            675                 680                 685

Glu Glu Asp Glu Asp Ser Asp Phe Gly Glu Glu Gln Arg Asp Cys Tyr
        690                 695                 700

Leu Lys Val Ser Gln Ser Lys Glu His Gln Gln Phe Ile Thr Phe Leu
705                 710                 715                 720
```

```
Gln Arg Leu Leu Gly Pro Leu Leu Glu Ala Tyr Ser Ser Ala Ala Ile
            725                 730                 735

Phe Val His Asn Phe Ser Gly Pro Val Pro Glu Ser Glu Tyr Leu Gln
            740                 745                 750

Lys Leu His Arg Tyr Leu Ile Thr Arg Thr Glu Arg Asn Val Ala Val
            755                 760                 765

Tyr Ala Glu Ser Ala Thr Tyr Cys Leu Val Lys Asn Ala Val Lys Met
770                 775                 780

Phe Lys Asp Ile Gly Val Phe Lys Glu Thr Lys Gln Lys Arg Val Ser
785                 790                 795                 800

Val Leu Glu Leu Ser Ser Thr Phe Leu Pro Gln Cys Asn Arg Gln Lys
            805                 810                 815

Leu Leu Glu Tyr Ile Leu Ser Phe Val Val Leu
            820                 825

<210> SEQ ID NO 28
<211> LENGTH: 201
<212> TYPE: PRT
<213> ORGANISM: Sus scrofa

<400> SEQUENCE: 28

Asn Ser Glu Asp Val Met His Ala Ile Gln Leu Leu Gly Asn Cys
1               5                   10                  15

Ile Thr Ile Thr His Thr Ser Arg Asn Asp Glu Phe Phe Ile Thr Pro
            20                  25                  30

Ser Thr Thr Val Pro Ser Val Phe Glu Leu Asn Phe Tyr Ser Asn Gly
            35                  40                  45

Val Leu His Val Phe Ile Met Glu Ala Ile Ile Ala Cys Ser Leu Tyr
        50                  55                  60

Ala Val Leu Lys Lys Arg Gly Ser Gly Gly Pro Ala Ser Pro Ser Leu
65                  70                  75                  80

Ile Ser Gln Glu Gln Leu Val Arg Lys Ala Ala Ser Leu Cys Tyr Leu
                85                  90                  95

Leu Ser Asn Glu Gly Thr Ile Ser Leu Pro Cys Gln Thr Phe Tyr Gln
            100                 105                 110

Ile Cys His Glu Thr Val Gly Arg Phe Ile Gln Tyr Gly Ile Leu Thr
        115                 120                 125

Val Ala Glu Gln Asp Asp Gln Glu Asp Ile Ser Pro Ser Leu Ala Glu
    130                 135                 140

Gln His Trp Asp Lys Lys Leu Pro Glu Pro Leu Ser Trp Arg Ser Asp
145                 150                 155                 160

Glu Glu Asp Glu Asp Ser Asp Phe Gly Glu Glu Gln Arg Asp Cys Tyr
                165                 170                 175

Leu Lys Val Ser Gln Ser Lys Glu His Gln Gln Phe Ile Thr Phe Leu
            180                 185                 190

Gln Arg Leu Leu Gly Pro Leu Leu Glu
        195                 200

<210> SEQ ID NO 29
<211> LENGTH: 259
<212> TYPE: PRT
<213> ORGANISM: Mus musculus

<400> SEQUENCE: 29

Met His Ser Ser Val Tyr Phe Val Ala Leu Val Ile Leu Gly Ala Ala
1               5                   10                  15
```

Val Cys Ala Ala Gln Pro Arg Gly Arg Ile Leu Gly Gly Gln Glu Ala
            20                  25                  30

Ala Ala His Ala Arg Pro Tyr Met Ala Ser Val Gln Val Asn Gly Thr
        35                  40                  45

His Val Cys Gly Gly Thr Leu Leu Asp Glu Gln Trp Val Leu Ser Ala
 50                  55                  60

Ala His Cys Met Asp Gly Val Thr Asp Asp Ser Val Gln Val Leu
65                  70                  75                  80

Leu Gly Ala His Ser Leu Ser Ala Pro Glu Pro Tyr Lys Arg Trp Tyr
                85                  90                  95

Asp Val Gln Ser Val Val Pro His Pro Gly Ser Arg Pro Asp Ser Leu
            100                 105                 110

Glu Asp Asp Leu Ile Leu Phe Lys Leu Ser Gln Asn Ala Ser Leu Gly
            115                 120                 125

Pro His Val Arg Pro Leu Pro Leu Gln Tyr Glu Asp Lys Glu Val Glu
        130                 135                 140

Pro Gly Thr Leu Cys Asp Val Ala Gly Trp Gly Val Val Thr His Ala
145                 150                 155                 160

Gly Arg Arg Pro Asp Val Leu His Gln Leu Arg Val Ser Ile Met Asn
                165                 170                 175

Arg Thr Thr Cys Asn Leu Arg Thr Tyr His Asp Gly Val Val Thr Ile
            180                 185                 190

Asn Met Met Cys Ala Glu Ser Asn Arg Arg Asp Thr Cys Arg Gly Asp
        195                 200                 205

Ser Gly Ser Pro Leu Val Cys Gly Asp Ala Val Glu Gly Val Val Thr
210                 215                 220

Trp Gly Ser Arg Val Cys Gly Asn Gly Lys Lys Pro Gly Val Tyr Thr
225                 230                 235                 240

Arg Val Ser Ser Tyr Arg Met Trp Ile Glu Asn Ile Thr Asn Gly Asn
                245                 250                 255

Met Thr Ser

<210> SEQ ID NO 30
<211> LENGTH: 83
<212> TYPE: PRT
<213> ORGANISM: Sus scrofa

<400> SEQUENCE: 30

Trp Gln Arg Glu Asp His Glu Val Pro Ala Gly Thr Leu Cys Asp Val
1               5                   10                  15

Ala Gly Trp Gly Val Val Ser His Thr Gly Arg Arg Pro Asp Arg Leu
            20                  25                  30

Gln His Leu Leu Leu Pro Val Leu Asp Arg Thr Thr Cys Asn Leu Arg
        35                  40                  45

Thr Tyr His Asp Gly Thr Ile Thr Glu Arg Met Met Cys Ala Glu Ser
    50                  55                  60

Asn Arg Arg Asp Ser Cys Lys Gly Asp Ser Gly Gly Pro Leu Val Cys
65                  70                  75                  80

Gly Gly Val

<210> SEQ ID NO 31
<211> LENGTH: 891
<212> TYPE: PRT
<213> ORGANISM: Mus musculus

<400> SEQUENCE: 31

```
Met Asn Tyr Val Gly Gln Leu Ala Gly Gln Val Phe Val Thr Val Lys
1               5                   10                  15

Glu Leu Tyr Lys Gly Leu Asn Pro Ala Thr Leu Ser Gly Cys Ile Asp
            20                  25                  30

Ile Ile Val Ile Arg Gln Pro Asn Gly Ser Leu Gln Cys Ser Pro Phe
        35                  40                  45

His Val Arg Phe Gly Lys Met Gly Val Leu Arg Ser Arg Glu Lys Val
    50                  55                  60

Val Asp Ile Glu Ile Asn Gly Glu Ser Val Asp Leu His Met Lys Leu
65                  70                  75                  80

Gly Asp Asn Gly Glu Ala Phe Phe Val Gln Glu Thr Asp Asn Asp Gln
                85                  90                  95

Glu Ile Ile Pro Met Tyr Leu Ala Thr Ser Pro Ile Leu Ser Glu Gly
            100                 105                 110

Ala Ala Arg Met Glu Ser Gln Leu Lys Arg Asn Ser Val Asp Arg Ile
        115                 120                 125

Arg Cys Leu Asp Pro Thr Thr Ala Ala Gln Gly Leu Pro Pro Ser Asp
    130                 135                 140

Thr Pro Ser Thr Gly Ser Leu Gly Lys Lys Arg Arg Lys Arg Arg Arg
145                 150                 155                 160

Lys Ala Gln Leu Asp Asn Leu Lys Arg Asp Asp Asn Val Asn Thr Ser
                165                 170                 175

Glu Asp Glu Asp Met Phe Pro Ile Glu Met Ser Ser Asp Glu Asp Thr
            180                 185                 190

Ala Pro Met Asp Gly Ser Arg Thr Leu Pro Asn Asp Val Pro Pro Phe
        195                 200                 205

Gln Asp Asp Ile Pro Lys Glu Asn Phe Pro Ser Ile Ser Thr Tyr Pro
    210                 215                 220

Gln Ser Ala Ser Tyr Pro Ser Ser Asp Arg Glu Trp Ser Pro Ser Pro
225                 230                 235                 240

Ser Pro Ser Gly Ser Arg Pro Ser Thr Pro Lys Ser Asp Ser Glu Leu
                245                 250                 255

Val Ser Lys Ser Ala Asp Arg Leu Thr Pro Lys Asn Asn Leu Glu Met
            260                 265                 270

Leu Trp Leu Trp Gly Glu Leu Pro Gln Ala Ala Lys Ser Ser Ser Pro
        275                 280                 285

His Lys Met Lys Glu Ser Ser Pro Leu Gly Ser Arg Lys Thr Pro Asp
    290                 295                 300

Lys Met Asn Phe Gln Ala Ile His Ser Glu Ser Ser Asp Thr Phe Ser
305                 310                 315                 320

Asp Gln Ser Pro Thr Met Ala Arg Gly Leu Leu Ile His Gln Ser Lys
                325                 330                 335

Ala Gln Thr Glu Met Gln Phe Val Asn Glu Glu Asp Leu Glu Ser Leu
            340                 345                 350

Gly Ala Ala Ala Pro Pro Ser Pro Val Ala Glu Glu Leu Lys Ala Pro
        355                 360                 365

Tyr Pro Asn Thr Ala Gln Ser Ser Lys Thr Asp Ser Pro Ser Arg
    370                 375                 380

Lys Lys Asp Lys Arg Ser Arg His Leu Gly Ala Asp Gly Val Tyr Leu
385                 390                 395                 400

Asp Asp Leu Thr Asp Met Asp Pro Glu Val Ala Ala Leu Tyr Phe Pro
                405                 410                 415
```

```
Lys Asn Gly Asp Pro Gly Gly Leu Pro Lys Gln Ala Ser Asp Asn Gly
            420                 425                 430

Ala Arg Ser Ala Asn Gln Ser Pro Gln Ser Val Gly Ser Gly Ile
        435                 440                 445

Asp Ser Gly Val Glu Ser Thr Ser Asp Ser Leu Arg Asp Leu Pro Ser
    450                 455                 460

Ile Ala Ile Ser Leu Cys Gly Gly Leu Ser Asp His Arg Glu Ile Thr
465                 470                 475                 480

Lys Asp Ala Phe Leu Glu Gln Ala Val Ser Tyr Gln Gln Phe Ala Asp
            485                 490                 495

Asn Pro Ala Ile Ile Asp Asp Pro Asn Leu Val Val Lys Val Gly Asn
                500                 505                 510

Lys Tyr Tyr Asn Trp Thr Thr Ala Ala Pro Leu Leu Leu Ala Met Gln
            515                 520                 525

Ala Phe Gln Lys Pro Leu Pro Lys Ala Thr Val Glu Ser Ile Met Arg
    530                 535                 540

Asp Lys Met Pro Lys Lys Gly Gly Arg Trp Trp Phe Ser Trp Arg Gly
545                 550                 555                 560

Arg Asn Ala Thr Ile Lys Glu Glu Ser Lys Pro Glu Gln Cys Leu Thr
                565                 570                 575

Gly Lys Gly His Asn Thr Gly Glu Gln Pro Ala Gln Leu Gly Leu Ala
            580                 585                 590

Thr Arg Ile Lys His Glu Ser Ser Ser Asp Glu Glu His Ala Ala
        595                 600                 605

Ala Lys Pro Ser Gly Ser Ser His Leu Ser Leu Leu Ser Asn Val Ser
    610                 615                 620

Tyr Lys Lys Thr Leu Arg Leu Thr Ser Glu Gln Leu Lys Ser Leu Lys
625                 630                 635                 640

Leu Lys Asn Gly Pro Asn Asp Val Val Phe Ser Val Thr Thr Gln Tyr
            645                 650                 655

Gln Gly Thr Cys Arg Cys Glu Gly Thr Ile Tyr Leu Trp Asn Trp Asp
        660                 665                 670

Asp Lys Val Ile Ile Ser Asp Ile Asp Gly Thr Ile Thr Arg Ser Asp
    675                 680                 685

Thr Leu Gly His Ile Leu Pro Thr Leu Gly Lys Asp Trp Thr His Gln
    690                 695                 700

Gly Ile Ala Lys Leu Tyr His Lys Val Ser Gln Asn Gly Tyr Lys Phe
705                 710                 715                 720

Leu Tyr Cys Ser Ala Arg Ala Ile Gly Met Ala Asp Met Thr Arg Gly
            725                 730                 735

Tyr Leu His Trp Val Asn Glu Arg Gly Thr Val Leu Pro Gln Gly Pro
        740                 745                 750

Leu Leu Leu Ser Pro Ser Ser Leu Phe Ser Ala Leu His Arg Glu Val
            755                 760                 765

Ile Glu Lys Lys Pro Glu Lys Phe Lys Val Gln Cys Leu Thr Asp Ile
    770                 775                 780

Lys Asn Leu Phe Phe Pro Asn Thr Glu Pro Phe Tyr Ala Ala Phe Gly
785                 790                 795                 800

Asn Arg Pro Ala Asp Val Tyr Ser Tyr Lys Gln Val Gly Val Ser Leu
            805                 810                 815

Asn Arg Ile Phe Thr Val Asn Pro Lys Gly Glu Leu Val Gln Glu His
            820                 825                 830
```

```
Ala Lys Thr Asn Ile Ser Ser Tyr Val Arg Leu Cys Glu Val Val Asp
            835                 840                 845

His Val Phe Pro Leu Leu Lys Arg Ser His Ser Cys Asp Phe Pro Cys
        850                 855                 860

Ser Asp Thr Phe Ser Asn Phe Thr Phe Trp Arg Glu Pro Leu Pro Pro
865                 870                 875                 880

Phe Glu Asn Gln Asp Met His Ser Ala Ser Ala
                885                 890

<210> SEQ ID NO 32
<211> LENGTH: 931
<212> TYPE: PRT
<213> ORGANISM: Mus musculus

<400> SEQUENCE: 32

Met Leu Tyr Leu Glu Asp Asn Ser Glu Asp Lys Thr Val Gln Glu
1               5                   10                  15

Ser Ser Leu Ser Lys Pro Ala Ser Val Tyr His Gly Lys Ala Pro Pro
                20                  25                  30

Gly Ile Leu Ser Gln Thr Met Asn Tyr Val Gly Gln Leu Ala Gly Gln
            35                  40                  45

Val Leu Val Thr Val Lys Glu Leu Tyr Lys Gly Ile Asn Gln Ala Thr
    50                  55                  60

Leu Ser Gly Cys Ile Asp Val Val Val Arg Gln Gln Asp Gly Ser
65                  70                  75                  80

Tyr Gln Cys Ser Pro Phe His Val Arg Phe Gly Lys Leu Gly Val Leu
                85                  90                  95

Arg Ser Lys Glu Lys Val Ile Asp Ile Glu Ile Asn Gly Ser Ala Val
                100                 105                 110

Asp Leu His Met Lys Leu Gly Asp Asn Gly Glu Ala Phe Phe Val Glu
            115                 120                 125

Glu Thr Glu Glu Glu Tyr Glu Lys Leu Pro Ala Tyr Leu Ala Thr Ser
    130                 135                 140

Pro Ile Pro Thr Glu Asp Gln Phe Phe Lys His Ile Glu Thr Pro Leu
145                 150                 155                 160

Val Lys Ser Ser Gly Asn Glu Arg Pro Ala Gln Ser Ser Asp Val Ser
                165                 170                 175

His Thr Leu Glu Ser Glu Ala Val Phe Thr Gln Ser Ser Val Lys Lys
            180                 185                 190

Lys Lys Arg Arg Arg Lys Lys Cys Lys Gln Asp Asn Arg Lys Glu Glu
        195                 200                 205

Gln Ala Ala Ser Pro Val Ala Glu Asp Val Gly Asp Val Gly Val Ser
    210                 215                 220

Ser Asp Asp Glu Lys Arg Ala Gln Ala Ala Arg Gly Ser Ser Asn Ala
225                 230                 235                 240

Ser Leu Lys Glu Glu Asp Tyr Lys Glu Pro Ser Leu Phe His Ser Gly
                245                 250                 255

Asp Asn Tyr Pro Leu Ser Asp Gly Asp Trp Ser Pro Leu Glu Thr Thr
            260                 265                 270

Tyr Pro Gln Ala Val Cys Pro Lys Ser Asp Ser Glu Leu Glu Val Lys
        275                 280                 285

Pro Ser Glu Ser Leu Leu Arg Ser Glu Pro His Met Glu Trp Thr Trp
    290                 295                 300

Gly Gly Phe Pro Glu Ser Thr Lys Val Thr Lys Arg Glu Arg Tyr Asp
305                 310                 315                 320
```

```
Tyr His Pro Arg Thr Ala Thr Ile Thr Pro Ser Glu Asn Thr His Phe
            325                 330                 335

Arg Val Ile Pro Ser Glu Asp Ser Leu Ile Arg Glu Val Glu Lys Asp
            340                 345                 350

Ala Thr Val Glu Asp Thr Thr Cys Thr Ile Val Lys Pro Lys Pro Arg
            355                 360                 365

Ala Leu Cys Lys Gln Leu Ser Asp Ala Ala Ser Thr Glu Leu Pro Glu
            370                 375                 380

Ser Pro Leu Glu Ala Pro Gln Ile Ser Ser Leu Leu Asp Ala Asp Pro
385                 390                 395                 400

Val Pro Ser Pro Ser Ala Glu Ala Pro Ser Glu Pro Lys Pro Ala Ala
            405                 410                 415

Lys Asp Ser Pro Thr Lys Lys Gly Val His Lys Arg Ser Gln His
            420                 425                 430

Gln Gly Pro Asp Asp Ile Tyr Leu Asp Asp Leu Lys Ala Leu Glu Pro
            435                 440                 445

Glu Val Ala Ala Leu Tyr Phe Pro Lys Ser Asp Thr Asp Pro Gly Ser
            450                 455                 460

Arg Gln Trp Pro Glu Ser Asp Thr Phe Ser Gly Ser Gln Ser Pro Gln
465                 470                 475                 480

Ser Val Gly Ser Ala Ala Asp Ser Gly Thr Glu Cys Leu Ser Asp
            485                 490                 495

Ser Ala Met Asp Leu Pro Asp Val Thr Leu Ser Leu Cys Gly Gly Leu
            500                 505                 510

Ser Glu Asn Gly Glu Ile Ser Lys Glu Lys Phe Met Glu His Ile Ile
            515                 520                 525

Thr Tyr His Glu Phe Ala Glu Asn Pro Gly Leu Ile Asp Asn Pro Asn
            530                 535                 540

Leu Val Ile Arg Ile Tyr Asn Arg Tyr Asn Trp Ala Leu Ala Ala
545                 550                 555                 560

Pro Met Ile Leu Ser Leu Gln Val Phe Gln Lys Ser Leu Pro Lys Ala
            565                 570                 575

Thr Val Glu Ser Trp Val Lys Asp Lys Met Pro Lys Lys Ser Gly Arg
            580                 585                 590

Trp Trp Phe Trp Arg Lys Lys Glu Ser Met Ile Lys Gln Leu Pro Glu
            595                 600                 605

Thr Lys Glu Gly Lys Ser Glu Val Pro Pro Ala Asn Asp Leu Pro Ser
            610                 615                 620

Asn Ala Glu Glu Pro Thr Ser Ala Arg Pro Ala Glu Asn Asp Thr Ser
625                 630                 635                 640

Ser Asp Glu Gly Ser Gln Glu Leu Glu Glu Ser Ile Lys Val Asp Pro
            645                 650                 655

Ile Thr Val Glu Thr Leu Ser His Cys Gly Thr Ala Ser Tyr Lys Lys
            660                 665                 670

Ser Leu Arg Leu Ser Ser Asp Gln Ile Ala Lys Leu Lys Leu His Asp
            675                 680                 685

Gly Pro Asn Asp Val Val Phe Ser Ile Thr Thr Gln Tyr Gln Gly Thr
            690                 695                 700

Cys Arg Cys Ala Gly Thr Ile Tyr Leu Trp Asn Trp Asn Asp Lys Val
705                 710                 715                 720

Ile Ile Ser Asp Ile Asp Gly Thr Ile Thr Lys Ser Asp Ala Leu Gly
            725                 730                 735
```

```
                                    -continued

Gln Ile Leu Pro Gln Leu Gly Lys Asp Trp Thr His Gln Gly Ile Ala
            740                 745                 750

Arg Leu Tyr His Ser Ile Asn Glu Asn Gly Tyr Lys Phe Leu Tyr Cys
            755                 760                 765

Ser Ala Arg Ala Ile Gly Met Ala Asp Met Thr Arg Gly Tyr Leu His
            770                 775                 780

Trp Val Asn Asp Lys Gly Thr Ile Leu Pro Arg Gly Pro Leu Met Leu
785                 790                 795                 800

Ser Pro Ser Ser Leu Phe Ser Ala Phe His Arg Glu Val Ile Glu Lys
                805                 810                 815

Lys Pro Glu Lys Phe Lys Ile Glu Cys Leu Asn Asp Ile Lys Asn Leu
                820                 825                 830

Phe Ala Pro Ser Arg Gln Pro Phe Tyr Ala Ala Phe Gly Asn Arg Pro
                835                 840                 845

Asn Asp Val Tyr Ala Tyr Thr Gln Val Gly Val Pro Asp Cys Arg Ile
            850                 855                 860

Phe Thr Val Asn Pro Lys Gly Glu Leu Ile Gln Glu Arg Thr Lys Gly
865                 870                 875                 880

Asn Lys Ser Ser Tyr His Arg Leu Ser Glu Leu Val Glu His Val Phe
                885                 890                 895

Pro Leu Leu Ser Lys Glu Gln Asn Ser Ala Phe Pro Cys Pro Glu Phe
                900                 905                 910

Ser Ser Phe Cys Tyr Trp Arg Asp Pro Ile Pro Asp Leu Asp Leu Asp
            915                 920                 925

Asp Leu Ala
    930
```

METHODS FOR ELEVATING FAT/OIL CONTENT IN PLANTS

CROSS-REFERENCE TO RELATED APPLICATION

The present application claims the benefit of U.S. Provisional Application Ser. No. 61/739,499, filed Dec. 19, 2012, which is hereby incorporated by reference herein in its entirety, including any figures, tables, or drawings.

This invention was made with Government Support under Contract No. DE SC0000797 awarded by the Department of Energy. The Government has certain rights in the invention.

BACKGROUND OF THE INVENTION

Plants are a primary source of human and/or animal food, excellent feedstock for fuels, and useful for production of desirable chemicals. Plants synthesize and store lipids, primarily, in cytosolic lipid droplets. In plants, seeds are the primary site of oil synthesis and storage; vegetable oils (such as triacylglycerol) are used as a form of energy during seed germination. Vegetable oils can be synthesized in non-seed (such as leaf) tissues; however, their abundance is low and the stored lipids are presumed to be metabolized rapidly, perhaps for the recycling of fatty acids for energy or the synthesis of membrane lipids.

Plants that can accumulate oils in non-seed tissues are commercially attractive. The biomass of non-seed parts (such as leaves, stems) of plants is generally far greater than the amount accounted for by seeds. Thus, the transformation of non-seed tissues into oil-producing machinery can significantly increase the energy-production capacity. Currently, the regulation and transient accumulation of stored oils in non-seed tissues are not well understood, and the production of oils in non-seed plant tissues for industrial applications remains challenging. Cellular lipid droplets are dynamic organelles that regulate triglyceride storage in mammalian cells. Lipid droplets are composed of a core of neutral lipids surrounded by a phospholipid monolayer and associated proteins. Various lipid droplet-associated proteins, including fat specific protein 27 (FSP27), perilipins, seipin (Bernardinelli-Seip congenital lipodystrophy type 2 protein), FIT1 (fat storage-inducing transmembrane protein 1), and FIT2 (fat storage-inducing transmembrane protein 2) have been well characterized for their ability to regulate fat metabolism in mammalian species.

BRIEF SUMMARY OF THE INVENTION

In some embodiments, the present invention provides a method of elevating oil content in plants or plant parts by genetically modifying the plant to express a lipid droplet-associated protein or polypeptide (such as fat-specific protein 27) of animal origin in the plants or plant parts. In one specific embodiment, the present invention provides a method of elevating oil content in vegetative (non-seed) plant tissues.

In some embodiments, the present invention also provides genetically-modified plant cells, tissues, or whole plants with elevated cellular oil content, wherein the plant cell, tissue, or whole plant expresses a lipid droplet-associated protein or polypeptide (such as fat-specific protein 27) of animal origin. In certain embodiments, the ipid droplet-associated proteins or polypeptides useful according to the present invention are of mammalian origin. In some embodiments, the present invention provides a method for obtaining a plant cell with elevated lipid content, wherein the method comprises:

genetically modifying a plant cell to express an exogenous lipid droplet-associated protein or polypeptide, thereby obtaining a genetically-modified plant cell with elevated lipid content;

wherein the lipid droplet-associated protein induces adipogenesis, enhances the accumulation of cellular lipid droplets, and/or reduces lipase activity; and wherein the expression of the lipid droplet-associated protein or polypeptide increases lipid content of the genetically-modified plant cell as compared to a wild-type (native) plant cell of the same type.

In some embodiments, the present invention provides a method for obtaining a plant cell with elevated lipid content, wherein the method comprises:

transforming a plant cell with a vector comprising a nucleic acid sequence encoding an exogenous lipid droplet-associated protein or polypeptide, wherein the nucleic acid is operably linked to a promoter and/or a regulatory sequence;

wherein the lipid droplet-associated protein induces adipogenesis, enhances the accumulation of cellular lipid droplets, and/or reduces lipase activity;

wherein the transformed plant cell expresses the lipid droplet-associated protein or polypeptide; and wherein the expression of the lipid droplet-associated protein or polypeptide increases lipid content of the transformed plant cell as compared to a wild-type (native) plant cell of the same type.

In certain embodiments, the genetically-modified plant cell is contained in a plant tissue, plant part, or whole plant.

In some embodiments, the genetically-modified plant cell comprises, in its genome or in its plastome, a nucleic acid molecule encoding a lipid droplet-associated protein or polypeptide.

In some embodiments, the lipid droplet-associated protein or polypeptide is not of plant origin. In certain embodiments, the lipid droplet-associated protein or polypeptide is of animal origin, such as of insect, vertebrate, fish, bird, amphibian, or mammalian (e.g., mouse, human) origin.

In some embodiments, a T-DNA binary vector system is used for plant transformation. In one embodiment, plant transformation is performed using the floral dip method.

In certain embodiments, to elevate cellular lipid content and/or to induce lipid droplet production, the plant cell can be genetically engineered to expresses one or more lipid droplet-associated proteins or polypeptides including, but not limited to, fat specific protein 27 (FSP27); perilipins including PLIN1 (perilipin 1) and PLIN2 (also called autosomal dominant retinitis pigmentosa (ADRP)); seipin (Bernardinelli-Seip congenital lipodystrophy type 2 protein); FIT1 (fat storage-inducing transmembrane protein 1), and FIT2 (fat storage-inducing transmembrane protein 2); acyl-CoA:diacylglycerol acyltransferase 1 (DGAT-1) and phospholipid:diacylglycerol acyltransferase 1 (PDAT-1); cell death activator (Cidea); and WRINKLED1 (WRI1).

In certain embodiments, to elevate cellular lipid content and/or to induce lipid droplet production, the plant cell can be genetically engineered to expresses one or more lipid droplet-associated proteins or polypeptides including, but not limited to FSP27, PLIN1, PLIN2, Seipin, FIT1 and FIT2.

In certain specific embodiments, the transgenic plants express a combination of lipid droplet-associated proteins or peptides, wherein the lipid droplet-associated protein or peptide is selected from: DGAT-1 and FSP27; DGAT-1, cgi58 (mutation), and FSP27; DGAT-1, PDAT-1, and FSP27; DGAT-1, PDAT-1, cgi58 (mutation), FSP27; FSP27, PLIN2, and cgi58 (mutation); DGAT-1, FSP27, PLIN2, and cgi58 (mutation); and DGAT-1, PDAT-1, FSP27, PLIN2, and cgi58 (mutation).

In another embodiment, the present invention provides a method for obtaining an algae or bacterial cell with elevated lipid content, wherein the method comprises:

transforming an algae or bacterial cell with a vector comprising a nucleic acid sequence encoding an exogenous lipid droplet-associated protein or polypeptide, wherein the nucleic acid is operably linked to a promoter and/or a regulatory sequence;

wherein the lipid droplet-associated protein induces adipogenesis, enhances the accumulation of cellular lipid droplets, and/or reduces lipase activity;

wherein the transformed algae or bacterial cell expresses the lipid droplet-associated protein or polypeptide; and wherein the expression of the lipid droplet-associated protein or polypeptide increases lipid content of the transformed algae or bacterial cell as compared to a wild-type (native) algae or bacterial cell of the same type.

In certain embodiments, the algae cell can be genetically engineered to expresses any combinations of lipid droplet-associated proteins and peptides including, but not limited to, fat specific protein 27 (FSP27); perilipins including PLIN1 (perilipin 1) and PLIN2 (also called autosomal dominant retinitis pigmentosa (ADRP)); seipin (Bernardinelli-Seip congenital lipodystrophy type 2 protein); FIT1 (fat storage-inducing transmembrane protein 1), and FIT2 (fat storage-inducing transmembrane protein 2); acyl-CoA: diacylglycerol acyltransferase 1 (DGAT-1); phospholipid: diacylglycerol acyltransferase 1 (PDAT-1); cell death activator (Cidea); and WRINKLED1 (WRI1).

BRIEF DESCRIPTION OF THE SEQUENCES

Figure 1A:
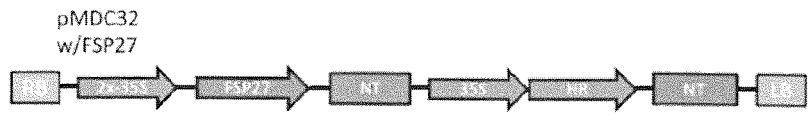
FIGS. 1A and 1B are diagrams that illustrate embodiments of the transfer DNA (T-DNA) region of the binary vector for transformation of *Arabidopsis thaliana* with the mouse fat specific protein 27 (FSP27) cDNA. The FSP27 open reading frame was inserted downstream from the 2X 35S promoter, either in-frame with green fluorescent protein (GFP) (pMDC43) or without (pMDC32). Binary vectors are known in the art, as described in Curtis and Grossniklaus (Plant Physiology, October 2003, Vol. 133, pp. 462-469), which is herein incorporated by reference in its entirety. Plasmid vectors were transformed into *Agrobacterium tumefaciens* LBA4404 and clones were selected and verified by PCR. *Arabidopsis* plants were transformed by the floral dip method of Bent and Clough (Plant J. 1998 December; 16(6):735-43.). Both wild-type plants (*Arabidopsis thaliana*, ecotype Columbia), and plants with a T-DNA insertional mutation in the At4g24160 locus were used for transformations. The T-DNA knockout is in an exon of the *Arabidopsis* homolog of the human CGI-58 gene, and in *Arabidopsis* plants with this mutation there is an increase in cytosolic lipid droplets in leaves (James et al., Proc Natl Acad Sci USA. 2010 Oct. 12; 107(41):17833-8).

SEQ ID NO:1 (GenBank Accession Q96AQ7) is the amino acid sequence of a human fat specific protein 27 (FSP27).

SEQ ID NO:2 (GenBank Accession NP_848460) is the amino acid sequence of a mouse fat specific protein 27 (FSP27).

SEQ ID NO:3 (GenBank Accession NP_002657) is the amino acid sequence of a human PLN1 (perilipin 1).

SEQ ID NO:4 (GenBank Accession Q96AQ7) is the amino acid sequence of a mouse PLN1 (perilipin 1).

SEQ ID NO:5 (GenBank Accession NP_001106942) is the amino acid sequence of a human PLIN2 (also called autosomal dominant retinitis pigmentosa (ADRP)).

SEQ ID NO:6 (GenBank Accession NP_031434) is the amino acid sequence of a mouse PLIN2 (also called autosomal dominant retinitis pigmentosa (ADRP)).

SEQ ID NO:7 (GenBank Accession Q96G97) is the amino acid sequence of a human seipin (Bernardinelli-Seip congenital lipodystrophy type 2 protein).

SEQ ID NO:8 (GenBank Accession AAH43023) is the amino acid sequence of a mouse seipin (Bernardinelli-Seip congenital lipodystrophy type 2 protein).

SEQ ID NO:9 (GenBank Accession A5D6W6) is the amino acid sequence of a human FIT1 (fat storage-inducing transmembrane protein 1).

SEQ ID NO:10 (GenBank Accession NP_081084) is the amino acid sequence of a mouse FIT1 (fat storage-inducing transmembrane protein 1).

SEQ ID NO:11 (GenBank Accession Q8N6M3) is the amino acid sequence of a human FIT2 (fat storage-inducing transmembrane protein 2).

SEQ ID NO:12 (GenBank Accession NP_775573) is the amino acid sequence of a mouse human FIT2 (fat storage-inducing transmembrane protein 2).

SEQ ID NO:13 (GenBank Accession BT029749) is the mRNA sequence of the At4g24160 gene.

SEQ ID NO:14 (GenBank Accession ABM06019) is the amino acid sequence of the full length polypeptide encoded at the At4g24160 locus.

SEQ ID NO:15 (GenBank Accession ACA49853) is the amino acid sequence of a diacylglycerol acyltransferase 1 [*Jatropha curcas*].

SEQ ID NO:16 (GenBank Accession AED91921) is the amino acid sequence of a phospholipid: diacylglycerol acyltransferase 1 [*Jatropha curcas*].

SEQ ID NO:17 (GenBank Accession EDR11533) is the amino acid sequence of a phospholipid:diacylglycerol acyltransferase 1 [*Laccaria bicolor*].

SEQ ID NO:18 (GenBank Accession ABN67418) is the amino acid sequence of a phospholipid:diacylglycerol acyltransferase 1 [*Scheffersomyces stipitis*].

SEQ ID NO:19 (GenBank Accession AAW81962) is the amino acid sequence of an adipose triglyceride lipase [*Homo sapiens*].

SEQ ID NO:20 (GenBank Accession AAW81963) is the amino acid sequence of an adipose triglyceride lipase [*Mus musculus*].

SEQ ID NO:21 (GenBank Accession AAQ65241) is the amino acid sequence of a cell death activator [*Homo sapiens*].

SEQ ID N0:22 (GenBank Accession NP_031728) is the amino acid sequence of a cell death activator [*Mus musculus*].

SEQ ID NO:23 (GenBank Accession AAP80382) is the amino acid sequence of a WRINKLED1 [*Arabidopsis thaliana*].

SEQ ID NO:24](GenBank Accession NP_001038512) is the amino acid sequence of a cell death activator CIDE-3 [*Danio rerio*].

DETAILED DISCLOSURE OF THE INVENTION

In some embodiments, the present invention relates the use of lipid droplet-associated proteins originated from animals to elevate the lipid content in vegetative tissues (such as leaves) of plants. In certain embodiments, the ipid droplet-associated proteins or polypeptides useful according to the present invention are of mammalian origin.

As lipid has more than twice the energy content of carbohydrate or protein, the present invention can be used to increase energy content in crop biomass, useful for production of biofuel, renewable chemical feedstocks, animal feed, and nutritional products. The term "lipid," as used throughout, encompasses oils (such as triglyceride), and in some embodiments "lipid" is oil.

In some embodiments, a lipid droplet-associated protein, designated as fat storage protein 27 (FSP27), is expressed in leaves of transgenic *Arabidoposis thaliana* plants. Neutral lipid-specific fluorescent staining of cystolic lipid droplets reveals a marked increase in the number and size of lipid droplets in the mesophyll cells of the levels of transgenic plants, when compared with non-transformed plants of the same type. The expression of a fluorescent-tagged mouse FSP27 protein in transgenic plants shows the FSP27 protein associated with the lipid droplets in plant cells, similar to that of mouse adipocytes. When the FSP27 protein is expressed in the *Arabidopsis* cgi58 mutant background, lipid droplet formation and lipid content in leaves are further augmented, when compared to transgenic *Arabidopsis* plants that only express FSP27 or *Arabidopsis* cgi58 mutant.

In some embodiments, the present invention provides a method of elevating lipid content in a plant or plant part by genetically modifying the plant to express a lipid droplet-associated protein or polypeptide (such as fat-specific protein 27) of animal origin in the plant or plant part. In one specific embodiment, the present invention provides a method of elevating lipid content in vegetative (non-seed) plant tissues.

In some embodiments, the present invention also provides genetically-modified plant cells, tissues, or whole plants with elevated cellular lipid content, wherein the plant cells, tissues or whole plants express a lipid droplet-associated protein or polypeptide (such as fat-specific protein 27) of animal origin.

Genetically-Modified Plants with Elevated Lipid Content and/or Lipid Droplet Production In some embodiments, the present invention provides a method for obtaining a plant cell with elevated lipid content, wherein the method comprises:

genetically modifying a plant cell to express an exogenous lipid droplet-associated protein or polypeptide, thereby obtaining a genetically-modified plant cell with elevated lipid content;

wherein the lipid droplet-associated protein or polypeptide induces adipogenesis, enhances the accumulation of cellular lipid droplets, and/or reduces lipase activity; and wherein the expression of the lipid droplet-associated protein or polypeptide increases lipid content of the genetically-modified plant cell, when compared to a wild-type (native) plant cell of the same type.

In some embodiments, the present invention provides a method for obtaining a plant cell with elevated lipid content, wherein the method comprises:

transforming a plant cell with a vector comprising a nucleic acid sequence encoding an exogenous lipid droplet-associated protein or polypeptide, yielding a transformed cell wherein the nucleic acid is operably linked to a promoter and/or a regulatory sequence;

wherein the lipid droplet-associated protein or polypeptide induces adipogenesis, enhances the accumulation of cellular lipid droplets, and/or reduces lipase activity;

wherein the transformed plant cell expresses the lipid droplet-associated protein or polypeptide; and wherein the expression of the lipid droplet-associated protein or polypeptide increases lipid content of the transformed plant cell as compared to a wild-type (native) plant cell of the same type.

In certain embodiments, the genetically-modified plant cell is contained in a plant tissue, plant part, or whole plant.

In some embodiments, the genetically-modified plant cell comprises, in its genome, a nucleic acid molecule encoding a lipid droplet-associated protein or polypeptide.

In some embodiments, the lipid droplet-associated protein or polypeptide is not of plant origin. In certain embodiments, the lipid droplet-associated protein or polypeptide is of animal origin, such as of insect, vertebrate, amphibian, or mammalian (e.g., mouse, human) origin. In another embodiment, the lipid droplet-associated protein or polypeptide is of plant origin.

In some embodiments, a T-DNA binary vector system is used for plant transformation. A T-DNA binary vector system is a pair of plasmids consisting of a binary plasmid and a helper plasmid. In one embodiment, the T-DNA region located on the binary vector comprises a vector nucleic acid sequence encoding an exogenous lipid droplet-associated protein or polypeptide.

T-DNA binary vector systems are routinely used in plant transformation. A variety of vectors and expression cassettes useful for performing plant transformation are described in Curtis and Grossniklaus (2003), which is herein incorporated by reference in its entirety. Non-limiting examples of vectors and expression cassettes useful in accordance with the present invention include pMDC32, pMDC7, pMDC30, pMDC45, pMDC44, pMDC43, pMDC83, pMDC84, pMDC85, pMDC139, pMDC140, pMDC141, pMDC107, pMDC111, pMDC110, pMDC162, pMDC163, pMDC164, pMDC99, pMDC100, and pMDC123.

In some embodiments, plant transformation is performed using the floral dip method, as describe in Bent and Clough (1998), which is herein incorporated by reference in its entirety.

In certain embodiments, to elevate cellular lipid content and/or to induce lipid droplet production, the plant cell can be genetically engineered to expresses one or more lipid droplet-associated proteins or polypeptides including, but not limited to, fat specific protein 27 (FSP27); perilipins including PLIN1 (perilipin 1) and PLIN2 (also called autosomal dominant retinitis pigmentosa (ADRP)); seipin (Bernardinelli-Seip congenital lipodystrophy type 2 protein); FIT1 (fat storage-inducing transmembrane protein 1), and FIT2 (fat storage-inducing transmembrane protein 2); acyl-CoA:diacylglycerol acyltransferase 1 (DGAT-1); phospholipid:diacylglycerol acyltransferase 1 (PDAT-1); cell death activator (Cidea); and WRINKLED1 (WRI1).

In certain specific embodiments, the plant cell can be genetically engineered to express one or more functional domains of the lipid droplet-associated proteins or polypeptides, wherein the functional domain is involved lipid metabolism, including, but not limited to, the synthesis, protection, accumulation, storage, or breakdown of lipids.

In another embodiment, to elevate cellular lipid content and/or to induce lipid droplet production, the plant cell can be genetically engineered to over-express one or more lipid droplet-associated proteins or polypeptides of plant origin.

A variety of LD-associated proteins are known in the art; amino acid sequences of LD-associated proteins, as well as cDNA sequences encoding LD-associated proteins, are publically available, such as via the GenBank database.

Fat Specific Protein 27 (FSP27), a lipid droplet (LD) associated protein in adipocytes, regulates triglyceride (TG) storage. FSP27 plays a key role in LD morphology to accumulate TGs. FSP27 facilitates LD clustering and promotes their fusion to form enlarged droplets, resulting in triglyceride accumulation. Functional domains of FSP27 responsible for LD formation have been characterized (see Jambunathan et al., 2011, which is hereby incorporated by reference in its entirety). Specifically, amino acids 173-220 of human FSP27 are necessary and sufficient for both the targeting of FSP27 to LDs and the initial clustering of the droplets. Amino acids 120-140 of human FSP27 are essential but not sufficient for LD enlargement, whereas amino acids 120-210 of human FSP27 are necessary and sufficient for both clustering and fusion of LDs to form enlarged droplets. In addition, FSP27-mediated enlargement of LDs, but not their clustering, is associated with triglyceride accumulation. CIDEC (human ortholog of FSP27) results in the accumulation of multiple, small LD's in white adipocytes in vivo.

In certain embodiments, the plant cell can be genetically engineered to express one or more functional domains of FSP27, including, but not limited to, amino acids 173-220 of human FSP27, amino acids 120-140 of human FSP27, amino acids 120-210 of human FSP27, or any fragment having no fewer than 10 consecutive amino acids (such as, more than 12, 13, 14, 15, 16, 17, 18, 19, 20, 21, 22, 23, 24, 25, 30, 35, 40, 45, 50, 55, 60, 65, 70, 75, 80, 85, 90, 95, 100 consecutive amino acids) of the aforementioned functional domains.

In certain embodiments, the plant cell can be genetically engineered to express a FSP protein or peptide that corresponds to amino acids 120-220 of mouse FSP27 of SEQ ID NO:2 (GenBank Accession No. NP 848460), or any fragment thereof having no fewer than 10 consecutive amino acids (such as, more than 12, 13, 14, 15, 16, 17, 18, 19, 20, 21, 22, 23, 24, 25, 30, 35, 40, 45, 50, 55, 60, 65, 70, 75, 80, 85, 90, 95, 100 consecutive amino acids).

Members of the PAT family (also called the perilipin (PLIN) family), which regulate lipolysis, are a family of LD-asssciated proteins that have been well characterized in the art. Perilipins function as a protective coating from the body's natural lipases, such as hormone-sensitive lipase, which break triglycerides into glycerol and free fatty acids for use in metabolism—a process called lipolysis.

Acyl-CoA:diacylglycerol acyltransferase 1 (DGAT-1) and phospholipid:diacylglycerol acyltransferase 1 (PDAT-1) proteins are essential for triacylglyceride (Oil) biosynthesis in plants and seeds. DGAT-1 is also responsible for triglyceride biosynthesis in mammals. See Zhang et al. (2009)

Plant Cell 21, 3885-901, PMID: 20040537, which is hereby incorporated as reference in its entirety.

Mutations in cgi58 (plant ortholog is also called cgi58) can be used to increase in plant oil contents. See James et al. (2010) PNAS 107, 17833-1838, PMID: 20876112, which is hereby incorporated as reference in its entirety.

Yeast gene seipin (human ortholog is also called seipin) can be used to increase the size of oil droplets in mammalian cells. See Szymanski et al. (2007) PNAS 104, 20890-5, PMID: 18093937, which is hereby incorporated as reference in its entirety.

FIT1 and FIT2 proteins, which belong to the FIT family (also have orthologues in yeast), play an important role in lipid droplet formation. Gross et al. (2011) PNAS 108, 19581-19586; PMID: 22106267, which is hereby incorporated as reference in its entirety.

Mammalian genes PLIN1 and PLIN2 play a role in protecting against breakdown of fat (called hydrolysis or lipolysis).

Cgi58activate lipases (e.g., adipose triglyceride lipase (ATGL)), which catalyze the breakdown of lipids.

Cell death activator (Cidea), a novel gene identified by the inventors, plays a role in triglyceride accumulation in humans.

In certain embodiments, the plant cell can be genetically engineered to expresses any combinations of lipid droplet-associated proteins and peptides including, but not limited to, fat specific protein 27 (FSP27); perilipins including PLIN1 (perilipin 1) and PLIN2 (also called autosomal dominant retinitis pigmentosa (ADRP)); seipin (Bernardinelli-Seip congenital lipodystrophy type 2 protein); FIT1 (fat storage-inducing transmembrane protein 1), and FIT2 (fat storage-inducing transmembrane protein 2); acyl-CoA: diacylglycerol acyltransferase 1 (DGAT-1); phospholipid: diacylglycerol acyltransferase 1 (PDAT-1); cell death activator (Cidea); and WRINKLED1 (WRI1).

In one embodiment, the plant cell can be genetically engineered to expresses one or more lipid droplet-associated proteins in a cgi58 (mutation) background, wherein the cgi58 (mutation) background results in enhanced lipid/oil content in plants.

In certain specific embodiments, the transgenic plants express a combination of nucleic acids expressing lipid droplet-associated proteins selected from: DGAT-1 and FSP27; DGAT-1, cgi58 (mutation), and FSP27; DGAT-1, PDAT-1, and FSP27; DGAT-1, PDAT-1, cgi58 (mutation), FSP27; FSP27, PLIN2, and cgi58 (mutation); DGAT-1, FSP27, PLIN2, and cgi58 (mutation); and DGAT-1, PDAT-1, FSP27, PLIN2, and cgi58 (mutation). In some embodiments, any lipid droplet-associated protein or polypeptide of animal origin can be used in accordance with the present invention. In certain embodiments, suitable lipid droplet-associated proteins or polypeptides can be originated from insects, fish, birds, vertebrates, amphibians, and mammalian species including, but not limited to apes, chimpanzees, orangutans, humans, monkeys, dogs, cats, horses, cattle, pigs, sheep, goats, chickens, mice, rats, guinea pigs, and hamsters.

In certain embodiments, the plant cell can be genetically engineered to expresses a lipid droplet-associated protein or polypeptide comprising any of SEQ ID NOs: 1-12 and 14-24, a homolog or variant thereof, or a functional fragment of a lipid droplet-associated protein or polypeptide comprising of SEQ ID NOs: 1-12 and 14-24, or a homolog or variant thereof, wherein the functional variant and the functional fragment induces adipogenesis, enhances the accumulation of cellular lipid droplets, and/or reduces lipase activity.

In certain embodiments, a variant of a lipid droplet-associated protein or polypeptide comprising a sequence of SEQ ID NOs:1-12 and 14-24 comprises an amino acid sequence that may share about at least 70%, 75%, 80%, 85%, 90%, 95%, 98%, 99%, or greater sequence similarity at the respective amino acid sequence of SEQ ID NOs:1-12 and 14-24.

The term "homolog," as used herein, refers to genes or proteins related to each other by descent from a common ancestral DNA (such as genes) or protein sequence. In certain embodiments, a homolog of a lipid droplet-associated protein or polypeptide comprising a sequence of SEQ ID NOs:1-12 and 14-24 comprises an amino acid sequence that may share about at least 70%, 75%, 80%, 85%, 90%, 95%, 98%, 99%, or greater sequence similarity at the respective amino acid sequence of SEQ ID NOs:1-12 and 14-24.

The sequence identity will typically be greater than 75%, preferably greater than 80%, more preferably greater than 90%, and can be greater than 95%. The identity and/or similarity of a sequence can be 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, word-length=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

Furthermore, as various lipid droplet-associated proteins have been well characterized in the art, a skilled artisan can readily make modifications to native or naturally-occurring sequences without substantially affecting their function of regulating lipid metabolism. In certain embodiments, the present invention relates to use of lipid droplet-associated proteins or polypeptides comprising no more than 150, 140, 130, 120, 110, 100, 90, 80, 70, 60, 50, 40, 30, 25, 20, 15, 10, 9, 8, 7, 6, 5, 4, 3, 2, or 1 conservative modification(s) (e.g., conservative substitutions, additions, deletions) to any of naturally-occurring sequences, such as SEQ ID NOs:1-12 and 14-24.

In addition, the present invention relates to the use of functional fragments of naturally-occurring lipid droplet-associated proteins or polypeptides. In certain embodiments, the functional fragments comprise at least 10, 15, 20, 25, 30, 35, 40, 45, 50, 55, 60, 75, 80, 85, 90, 95, 100, 110, 120, 130, 140, 150, 160, 170, 180, 190, 200, 210, 220, 230, 240, 250, 280, 300, 330, or 350 consecutive amino acids of any of SEQ ID NOs:1-12 and 14.

In certain embodiments, plant species that can be genetically-modified in accordance with the current invention include, but are not limited to, monocots, dicots, crop plants (i.e., any plant species grown for purposes of agriculture, food production for animals including humans), trees (i.e., fruit trees, trees grown for wood production, trees grown for decoration, etc.), flowers of any kind (i.e., plants grown for purposes of decoration, for example, following their harvest), and cacti. More specific examples of plants that can be genetically-modified to express one or more lipid droplet-associated proteins or polypeptides include, but are not limited to, Viridiplantae, Streptophyta, Embryophyta, Tracheophyta, Euphyllophytes, Spermatophyta, Magnoliophyta, Liliopsida, Commelinidae, Poales, Poaceae, *Oryza, Oryza sativa, Zea, Zea mays, Hordeum, Hordeum vulgare, Triticum, Triticum aestivum*, Eudicotyledons, Core eudicots, Asteridae, Euasterids, Rosidae, Eurosids II, Brassicales, Brassicaceae, *Arabidopsis*, Magnoliopsida, Solananae, Solanales, Solanaceae, *Solanum*, and *Nicotiana*. Thus, the embodiments of the invention have uses over a broad range of plants including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Panneserum, Persea, Phaseolus, Pistachia, Pisum, Pyrus, Prunus, Raphanus, Ricinus, Secale, Senecio, Sinapis, Solanum, Sorghum, Theobromus, Trigonella, Titicum, Vicia, Vitis, Vigna*, and *Zea*.

In certain embodiments, plant species that can be genetically-modified in accordance with the current invention include, but are not limited to, corn, sugarcane, sorghum, millet, rice, wheat, barley, soybean, olive, peanut, castor, oleaginous fruits such as palm and avocado, *Glycine* sp., grape, canola, *Arabidopsis, Brassica* sp., cotton, tobacco, bamboo, sugar beet, sunflower, willow, switchgrass (*Panicum virgatum*), giant reed (*Arundo donax*), reed canarygrass (*Phalaris arundinacea*), *Miscanthus*.times.*giganteus, Miscanthus* sp., *Sericea lespedeza* (*Lespedeza cuneata*), ryegrass (*Lolium multiflorum, lolium* sp.), timothy, kochia (*Kochia scoparia*), forage soybeans, alfalfa, clover, turf grass, sunn hemp, kenaf, bahiagrass, bermudagrass, dallisgrass, pangolagrass, big bluestem, indiangrass, fescue (*Festuca* sp.) including tall fescue, *Dactylis* sp., Brachypodium distachyon, smooth bromegrass, orchardgrass, kentucky bluegrass, yellow nutsedge, pine, poplar (*Populus* sp.), and eucalyptus, among others.

In certain specific embodiments, plant species that can be genetically-modified in accordance with the current invention include, but are not limited to, sorghum; switchgrass (*panicum*); wheat (*triticum*); sugarcane (for expression in leaves and stems); camelina, canola (for expression in oil seeds); soybean; safflower; and jatropha (e.g., for expression in seeds).

In certain embodiments, plant species that can be genetically-modified in accordance with the current invention include grasses such as the Poaceae (or Gramineae) family, the sedges (Cyperaceae), and the rushes (Juncaceae).

While *Arabidopsis thaliana* is used in the present invention as an example of plant species to demonstration that plants transformed with lipid droplet-associated proteins have elevated cellular lipid content and/or increased lipid droplet formation, those skilled in the art would readily obtain transgenic plants of other species with elevated cellular lipid content and/or increased lipid droplet formation, wherein transgenic plants express lipid droplet-associated proteins.

Triacylglycerols (TG) can be synthesized in non-seed tissues; however, their abundance is low and these storage lipids are presumed to be metabolized rapidly, perhaps for the recycling of fatty acids for energy or the synthesis of membrane lipids.

In certain embodiments, the present invention provides a method of elevating lipid content and/or inducing lipid droplet accumulation in vegetative plant (non-seed) tissues or plant parts including, but not limited to, leaves, roots, stems, shoots, buds, tubers, fruits, and flowers. In another embodiment, the present invention provides elevated lipid content and/or induces lipid droplet accumulation in seeds.

In some embodiments, the present invention can be used to increase total fatty acid content of the plant cell. In certain embodiments, the present invention can be used to increase the level of fatty acids including leaf-specific fatty acids, including but not limited to, triacylglycerol, hydroxyl, epoxy, cyclic, acetylenic, saturated, polyunsaturated (such as omega-3, omega-6 fatty acids), and short-chain or long-chain fatty acids, which can be incorporated into neutral lipids that can be compartmentalized in lipid droplets, including TAGs, wax-esters, and steryl-esters.

In some embodiments, the method for obtaining a plant cell with elevated lipid content further comprises: down-regulating, in the plant cell, the function of an At4924160 gene product.

Chanarin-Dorfman Syndrome is a neutral-lipid storage disorder (Lefevre et al., 2001; Bruno et al., 2008). CGI58, also known as ABHD5, associates with lipid droplets in human cells and participates in storage lipid hydrolysis. A mutation in this protein results in hyperaccumulation of lipid droplets in cells and the pathology associated with this syndrome. The CGI58 protein sequence includes a so-called "alpha/beta hydrolase fold" that is shared by members of the esterase/lipase/thioesterase family, suggesting that it might be a TAG lipase. Recent analyses of its functional properties have indicated that the mammalian polypeptide stimulates the activity of a lipase called ATGL (Adipose Triglyceride Lipase), which is the major lipase responsible for catalyzing the initial step of TAG breakdown in both adipose and non-lipid storing cell types (e.g. Lass et al., 2006; Yen & Farese, 2006; Schweiger et al., 2006; Yamaguchi et al., 2007). Interestingly, CGI58 also possesses lysophosphatidic acid acyltransferase (LPAAT) activity in vitro, suggesting that, in addition to its role in stimulating lipase activity, it may play a role in recycling of fatty acids into membrane phospholipids (Ghosh et al., 2008).

At4g24160 has been identified as a putative homolog of human CGI58, in *Arabidopsis thaliana*. The gene in *Arabidopsis* is apparently expressed as two alternative transcripts (two distinct cDNAs corresponding to the same gene have been identified) and the predicted protein products share domain architecture with other lipases/esterases and acyltransferases. *Arabidopsis* mutant lines lacking the function of the CGI58 homolog (i.e., At4g24160) contained vegetative (i.e. non-seed) tissues with metabolic machinery capable of synthesizing and storing oil as TAG, demonstrating that there are mechanisms in place to regulate this process in non-seed tissues.

The term "down-regulating," as used herein, refers to reducing the expression or function of a gene of interest. In certain embodiments, the reduction in expression or function of a gene of interest may be least a 25%, 30%, 40%, 50%, 60%, 70%, 80%, 90%, or 100%, when compared to wild-type. The down-regulation of function may also be measured by assaying the enzymatic activity of a polypeptide that is regulated by a polypeptide encoded by the gene of interest.

In certain embodiments of the invention, down-regulation of the activity of a polypeptide encoded by a gene may be accomplished using antisense-mediated-, or dsRNA-mediated-, or other forms of RNA-mediated-interference (RNAi), as is well known in the art. Methods for identification of candidate nucleotide sequences for RNA-mediated gene suppression, and design of oligonucleotides and constructs to achieve RNA-mediated gene suppression, are well known (e.g. Reynolds et al., 2004; Lu and Mathews, 2008).

In one embodiment, the plant cell can be genetically engineered to expresses one or more lipid droplet-associated proteins in a cgi58 (mutation) background, wherein the CGI58 (mutation) background results in enhanced lipid content in plants. In one embodiment, the plant cell of the present invention has a cgi58 (mutation) background described in US2010/0221400.

Methods for the genetic control of lipid accumulation in vegetative (non-seed) portions of plants by down-regulation of activity of At4g24160 or a homolog thereof are described in US2010/0221400, which is herein incorporated by reference in its entirety.

In certain embodiments, the present invention provides a transgenic plant cell with elevated lipid content, wherein the transgenic plant cell expresses an exogenous lipid droplet-associated protein or polypeptide, wherein the lipid droplet-associated protein induces adipogenesis, enhances the accumulation of cellular lipid droplets, and/or reduces lipase activity; and wherein the expression of the lipid droplet-associated protein or polypeptide increases lipid content of the genetically-modified plant cell, when compared to a wild-type plant cell. In certain embodiments, the genetically-modified plant cell is contained in a plant tissue, plant part, or whole plant. In one embodiment, the genetically-modified plant cell comprises, in its genome, a transgene encoding a lipid droplet-associated protein or polypeptide that induces adipogenesis, enhances the accumulation of cellular lipid droplets, and/or reduces lipase activity.

As used herein, the term "genetically modified plant or plant parts" refers to a plant or a plant part, whether it is attached or detached from the whole plant. It also includes progeny of the genetically modified plant or plant parts that are produced through sexual or asexual reproduction. Similarly, "transformed plant cell" refers to the initial transformant as well as progeny cells of the initial transformant in which the heterologous genetic sequence is found.

"Progeny" includes the immediate and all subsequent generations of offspring traceable to a parent.

In some embodiments, the present invention provides a method for obtaining an algae or bacterial cell with elevated lipid content, wherein the method comprises:

genetically modifying an algae or bacterial cell to express an exogenous lipid droplet-associated protein or polypeptide, thereby obtaining a genetically-modified algae or bacterial cell with elevated lipid content;

wherein the lipid droplet-associated protein induces adipogenesis, enhances the accumulation of cellular lipid droplets, and/or reduces lipase activity; and wherein the expression of the lipid droplet-associated protein or polypeptide increases lipid content of the genetically-modified algae or bacterial cell, when compared to a wild-type (native) algae or bacterial cell of the same type.

In another embodiment, the present invention provides a method for obtaining an algae or bacterial cell with elevated lipid content, wherein the method comprises:

transforming an algae or bacterial cell with a vector comprising a nucleic acid sequence encoding an exogenous lipid droplet-associated protein or polypeptide, wherein nucleic acid is operably linked to a promoter and/or a regulatory sequence;

wherein the lipid droplet-associated protein induces adipogenesis, enhances the accumulation of cellular lipid droplets, and/or reduces lipase activity;

wherein the transformed algae or bacterial cell expresses the lipid droplet-associated protein or polypeptide; and wherein the expression of the lipid droplet-associated protein or polypeptide increases lipid content of the transformed algae or bacterial cell as compared to a wild-type (native) algae or bacterial cell of the same type.

In certain embodiments, the algae cell can be genetically engineered to expresses any combinations of lipid droplet-associated proteins and peptides including, but not limited to, fat specific protein 27 (FSP27); perilipins including PLIN1 (perilipin 1) and PLIN2 (also called autosomal dominant retinitis pigmentosa (ADRP)); seipin (Bernardinelli-Seip congenital lipodystrophy type 2 protein); FIT1 (fat storage-inducing transmembrane protein 1), and FIT2 (fat storage-inducing transmembrane protein 2); acyl-CoA: diacylglycerol acyltransferase 1 (DGAT-1); phospholipid: diacylglycerol acyltransferase 1 (PDAT-1); cell death activator (Cidea); and WRINKLED1 (WRI1). In some embodiments, algae can be selected from the group consisting of Amphora, Anabaena, Anikstrodesmis, Botryococcus, Chaetoceros, Chlorella, Chlorococcum, Cyclotella, Cylindrotheca, Euglena, Hematococcus, Isochrysis, Monodus, Monoraphidium, Nannochloris, Nannochloropsis, Navicula, Nephrochloris, Nephroselmis, Nitzschia, Nodularia, Nostoc, Oochromonas, Oocystis, Oscillartoria, Parachlorella, Pavlova, Phaeodactylum, Pinguiococcus, Playtomonas, Pleurochrysis, Porphyra, Pseudoanabaena, Pyramimonas, Rhodomonas, Selenastrum, Scenedesmus, Sticococcus, Synechococcus, Tetraselmis, Thalassiosira, and Trichodesmium.

Nucleic Acid Constructs, Expression Cassettes, and Host Cells

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter).

As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" or "native" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring, and includes "wild-type" plants.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell); however, in the context of a heterologous nucleic acid, the same nucleotide sequence as found endogenously is produced in an unnatural (e.g., greater than expected or greater than naturally found) amount in the cell, or a nucleic acid comprising a nucleotide sequence that differs in sequence from the endogenous nucleotide sequence but encodes the same protein (having the same or substantially the same amino acid sequence) as found endogenously is produced in an unnatural (e.g., greater than expected or greater than naturally found) amount in the cell; (c) the nucleic acid comprises two or more nucleotide sequences that are not found in the same relationship to each other in nature, e.g., the nucleic acid is recombinant. An example of a heterologous nucleic acid is a nucleotide sequence encoding a lipid droplet-associated protein or polypeptide operably linked to a transcriptional control element (for example, a promoter) to which an endogenous (naturally-occurring) lipid droplet-associated coding sequence is not normally operably linked. Another example of a heterologous nucleic acid is a high copy number plasmid comprising a nucleotide sequence encoding a lipid droplet-associated protein or polypeptide. Another example of a heterologous nucleic acid is a nucleic acid encoding a lipid droplet-associated protein or polypeptide, where a host cell that does not normally produce a lipid droplet-associated protein or polypeptide is genetically modified with the nucleic acid encoding a lipid droplet-associated protein or polypeptide; because lipid droplet-associated protein-encoding nucleic acids are not naturally found in the host cell, the nucleic acid is heterologous to the genetically modified host cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, for example, the term "recombinant" polynucleotide or nucleic acid refers to one which is not naturally occurring, for example, is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The terms "transformation" or "transformed" are used interchangeably herein with "genetic modification" or "genetically modified" and refer to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell or into a plastome of the cell. In prokaryotic cells, permanent changes can be introduced into the chromosome or via extrachromosomal elements such as plasmids, plastids, and expression vectors, which may contain one or more selectable markers to aid in their maintenance in the recombinant host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (for example, a cell line) cultured as a unicellular entity, which eukaryotic or prokaryotic cells can be, or have been, used as recipients for a nucleic acid (for example, an expression vector that comprises a nucleotide sequence encoding one or more gene products such as lipid droplet-associated proteins or polypeptides), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (for example, a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, for example, an exogenous nucleic acid that is foreign to the eukaryotic host cell, or a recombinant nucleic acid that is not normally found in the eukaryotic host cell.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

Expression cassettes may be prepared comprising a transcription initiation or transcriptional control region(s) (for example, a promoter), the coding region for the protein of interest, and a transcriptional termination region. Transcriptional control regions include those that provide for overexpression of the protein of interest in the genetically modified host cell; those that provide for inducible expression, such that when an inducing agent is added to the culture medium, transcription of the coding region of the protein of interest is induced or increased to a higher level than prior to induction.

An expression cassette may contain at least one polynucleotide of interest to be cotransformed into the organism. Such an expression cassette is preferably provided with a plurality of restriction sites for insertion of the sequences of the invention to be under the transcriptional regulation of the regulatory regions. The expression cassette may additionally contain selectable marker genes.

The cassette may include 5' and 3' regulatory sequences operably linked to a polynucleotide of interest. By "operably linked" is intended, for example, a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. When a polynucleotide comprises a plurality of coding regions that are operably linked such that they are under the control of a single promoter, the polynucleotide may be referred to as an "operon".

The expression cassette will optionally include in the 5'-3' direction of transcription, a transcriptional and translational initiation region, a polynucleotide sequence of interest and a transcriptional and translational termination region functional in plants. The transcriptional initiation region, the promoter, is optional, but may be native or analogous, or foreign or heterologous, to the intended host. Additionally, the promoter may be the natural sequence or alternatively a synthetic sequence. By "foreign" is intended that the transcriptional initiation region is not found in the native organism into which the transcriptional initiation region is introduced. As used herein, a chimeric gene comprises a coding sequence operably linked to a transcriptional initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) Gene 91:151-158; Ballas et al. (1989) *Nucleic Acids Res.* 17:7891-7903; and Joshi et al. (1987) *Nucleic Acid Res.* 15:9627-9639.

Where appropriate, the polynucleotides of interest may be optimized for expression in the transformed organism. That is, the genes can be synthesized using plant or algae genomic preferred codons (for genomic transformation) or plastid-preferred codons corresponding to the plastids of the plant or algae of interest (for plastidic transformation). Methods are available in the art for synthesizing such codon optimized polynucleotides. See, for example, U.S. Pat. Nos. 5,380,831 and 5,436,391, and Murray et al. (1989) *Nucleic Acids Res.* 17:477-498, herein incorporated by reference. Of course, the skilled artisan will appreciate that for the transplastomic purposes described herein, sequence optimization should be conducted with plastid codon usage frequency in mind, rather than the plant or algae genome codon usage exemplified in these references.

It is now well known in the art that when synthesizing a polynucleotide of interest for improved expression in a host cell it is desirable to design the gene such that its frequency of codon usage approaches the frequency of codon usage of the host cell. It is also well known that plastome codon usage may vary from that of the host plant genome. For purposes of the subject invention, "frequency of preferred codon usage" is viewed in the context of whether the transformation is to be genomic or plastidic. For example, in the case of the latter, the phrase refers to the preference exhibited by a specific host cell plastid in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a plastid can be calculated by averaging frequency of preferred codon usage in a number of genes expressed by the plastid. It usually is preferable that this analysis be limited to genes that are among those more highly expressed by the plastid or in the host cell's genome, as appropriate. Alternatively, the polynucleotide of interest may be synthesized to have a greater number of the host plastid's most preferred codon for each amino acid, or to reduce the number of codons that are rarely used by the host.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region), Elroy-Stein et al. (1989) *PNAS USA*

86:6126-6130; potyvirus leaders, for example, TEV leader (Tobacco Etch Virus), Allison et al. (1986); MDMV Leader (Maize Dwarf Mosaic Virus) *Virology* 154:9-20; and human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625; tobacco mosaic virus leader (TMV), Gallie et al. (1989) in *Molecular Biology of RNA*, ed. Cech (Liss, New York), pp. 237-256; and maize chlorotic mottle virus leader (MCMV), Lommel et al. (1991) *Virology* 81:382-385. See also, Della-Cioppa et al. (1987) *Plant Physiol.* 84:965-968. Other methods known to enhance translation can also be utilized, for example, introns, and the like.

In preparing an expression cassette, the various polynucleotide fragments may be manipulated, so as to provide for the polynucleotide sequences in the proper orientation and, as appropriate, in the proper reading frame. Toward this end, adapters or linkers may be employed to join the polynucleotide fragments or other manipulations may be involved to provide for convenient restriction sites, removal of superfluous nucleotides, removal of restriction sites, or the like. For this purpose, in vitro mutagenesis, primer repair, restriction, annealing, resubstitutions, e.g., transitions and transversions, may be involved.

Tissue-specific promoters are well known in the art and can be used to localize expression of the heterologous coding sequence in desired plant parts.

In addition, expressed gene products may be localized to specific organelles in the target cell by ligating DNA or RNA coded for peptide leader sequences to the polynucleotide of interest. Such leader sequences can be obtained from several genes of either plant or other sources. These genes encode cytoplasmically-synthesized proteins directed to, for example, mitochondria (the F1-ATPase beta subunit from yeast or tobacco, cytochrome c1 from yeast), chloroplasts (cytochrome oxidase subunit Va from yeast, small subunit of rubisco from pea), endoplasmic reticulum lumen (protein disulfide isomerase), vacuole (carboxypeptidase Y and proteinase A from yeast, phytohemagglutinin from French bean), peroxisomes (D-aminoacid oxidase, uricase) and lysosomes (hydrolases).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength.

Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., *Molecular Cloning: A Laboratory Manual*, Third Edition, Cold Spring Harbor Laboratory Press, Cold Spring Harbor (2001).

As used herein, "stringent" conditions for hybridization refers to conditions wherein hybridization is carried out overnight at 20-25° C. below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

$Tm=81.5 C+16.6 Log [Na+]+0.41(\% G+C)-0.61(\% formamide)-600/length$ of duplex in base pairs.

Washes are typically carried out as follows:

(1) Twice at room temperature for 15 minutes in 1×SSPE, 0.1% SDS (low stringency wash).

(2) Once at Tm−20° C. for 15 minutes in 0.2×SSPE, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50 9.51). For hybridizations with shorter nucleic acids, i.e., oligonucleotides, the position of mismatches becomes more important, and the length of the oligonucleotide determines its specificity (see Sambrook et al., supra, 11.7 11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine. A lipid droplet-associated protein or polypeptide containing conserved amino acid substitutions as compared to a lipid droplet-associated protein or polypeptide exemplified herein would fall within the scope of "variants" of lipid droplet-associated proteins or polypeptides.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available. Fragments of full-length proteins can be produced by techniques well known in the art, such as by creating synthetic nucleic acids encoding the desired portions; or by use of Bal 31 exonuclease to generate fragments of a longer nucleic acid.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-410. Another alignment algorithm is FASTA, available in the Genetics Computing Group (GCG) package, from Madison, Wis., USA, a wholly owned subsidiary of Oxford Molecular Group, Inc. Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the term "variant" refers either to a naturally occurring genetic mutant of lipid droplet-associated protein or a recombinantly prepared variation of lipid droplet-associated protein, each of which contains one or more mutations in its DNA.

The term "variant" may also refer to either a naturally occurring variation of a given peptide or a recombinantly prepared variation of a given peptide or protein in which one or more amino acid residues have been modified by amino acid substitution, addition, or deletion. In certain embodiments, the variants include less than 75, less than 70, less than 60, less than 65, less than 60, less than 55, less than 50, less than 45, less than 40, less than 35, less than 30, less than 25, less than 20, less than 15, less than 10, less than 5, less than 4, less than 3, or less than 2 amino acid substitutions, rearrangements, insertions, and/or deletions relative to a naturally-occurring or native lipid droplet-associated protein or polypeptide.

In some embodiments, the transformation vector further comprises a nucleic acid that confers resistance to a selection agent selected from bar, pat, ALS, HPH, HYG, EPSP, and Hml.

Selectable marker genes include genes encoding antibiotic resistance, such as those encoding neomycin phosphotransferase II (NEO) and hygromycin phosphotransferase (HPT) as well as genes conferring resist insensitive to the herbicide or for an enzyme that degrades or detoxifies the herbicide in the plant before it can act. (See DeBlock et al. (1987) EMBO J, 6:2513-2518; DeBlock et al. (1989) Plant Physiol., 91:691-704; Fromm et al. (1990) 8:833-839. For example, resistance to glyphosate or sulfonylurea herbicides has been obtained by using genes coding for the mutant target enzymes, 5-enolpyruvylshikimate-3-phosphate synthase (EPSPS) and acetolactate synthase (ALS). Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to genes encoding: neomycin phosphotransferase II (Fraley et a. (1986) CRC Critical Reviews in Plant Science, 4:1-25); cyanamide hydratase (Maier-Greiner et al. (1991) Proc. Natl. Acad. Sci. USA, 88:4250-4264); aspartate kinase; dihydrodipicolinate synthase (Perl et al. (1993) Bio/Technology, 11:715-718); tryptophan decarboxylase (Goddijn et al. (1993) Plant Mol. Bio., 22:907-912); dihydrodipicolinate synthase and desensitized aspartade kinase (Perl et al. (1993) Bio/Technology, 11:715-718); bar gene (Toki et al. (1992) Plant Physiol., 100:1503-1507 and Meagher et al. (1996) and Crop Sci, 36:1367); tryptophane decarboxylase (Goddijn et al. (1993) Plant Mol. Biol., 22:907-912); neomycin phosphotransferase (NEO) (Southern et al. (1982) J. Mol. Appl. Gen., 1:327; hygromycin phosphotransferase (HPT or HYG) (Shimizu et al. (1986) Mol. Cell Biol., 6:1074); dihydrofolate reductase (DHFR) (Kwok et al. (1986) PNAS USA 4552); phosphinothricin acetyltransferase (DeBlock et al. (1987) EMBO J., 6:2513); 2,2-dichloropropionic acid dehalogenase (Buchanan-Wollatron et al. (1989) J. Cell. Biochem. 13D:330); acetohydroxyacid synthase (Anderson et al U.S. Pat. No. 4,761,373; Haughn et al. (1988) Mol. Gen. Genet. 221:266); 5-enolpyruvyl-shikimate-phosphate synthase (aroA) (Comai et al. (1985) Nature 317:741); haloarylnitrilase (Stalker et al., published PCT applon WO87/04181); acetyl-coenzyme A carboxylase (Parker et al. (1990) Plant Physiol. 92:1220); dihydropteroate synthase (sul I) (Guerineau et al. (1990) Plant Mol. Biol. 15:127); 32 kD photosystem II polypeptide (psbA) (Hirschberg et al. (1983) Science, 222:1346); etc.

Also included are genes encoding resistance to: chloramphenicol (Herrera-Estrella et al. (1983) EMBO J., 2:987-992); methotrexate (Herrera-Estrella et al. (1983) Nature, 303:209-213; Meijer et al. (1991) Plant Mol Bio., 16:807-820 (1991); hygromycin (Waldron et al. (1985) Plant Mol. Biol., 5:103-108; Zhijian et al. (1995) Plant Science, 108: 219-227 and Meijer et al. (1991) Plant Mol. Bio. 16:807-820); streptomycin (Jones et al. (1987) Mol. Gen. Genet., 210:86-91); spectinomycin (Bretagne-Sagnard et al. (1996) Transgenic Res., 5:131-137); bleomycin (Hille et al. (1986) Plant Mol. Biol., 7:171-176); sulfonamide (Guerineau et al. (1990) Plant Mol. Biol., 15:127-136); bromoxynil (Stalker et al. (1988) Science, 242:419-423); 2,4-D (Streber et al. (1989) Bio/Technology, 7:811-816); glyphosate (Shaw et al. (1986) Science, 233:478-481); phosphinothricin (DeBlock et al. (1987) EMBO J., 6:2513-2518); spectinomycin (Bretagne-Sagnard and Chupeau (1996) Transgenic Research 5:131-137).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hml gene for resistance to the Hc-toxin, and other selective agents used routinely and known to one of ordinary skill in the art.

Screening Methods for Obtaining Plants with Elevated Lipid Content

In some embodiments, the invention provides methods for screening for a functional lipid droplet-associated protein or polypeptide for elevating lipid content and/or inducing lipid droplet accumulation in a plant, bacterial, or algae cell, wherein the method comprises:

obtaining a test plant, bacterial, or algae cell genetically-modified to express a candidate exogenous lipid droplet-associated protein or polypeptide; and growing the genetically-modified test cell and selecting the genetically-modified test cell having elevated lipid content and/or increased lipid droplet level when compared to a native (wild-type) cell of the same type.

Embodiments of this invention also pertain to methods for screening for a functional lipid droplet-associated protein or polypeptide for elevating lipid content and/or inducing lipid droplet accumulation in a plant, bacterial, or algae cell, wherein the method comprises:

transforming a test plant, bacterial, or algae cell with a vector nucleic acid sequence encoding a candidate exogenous lipid droplet-associated protein or polypeptide, wherein the nucleic acid is operably linked to a promoter and/or a regulatory sequence; and growing the genetically-modified test cell and selecting the genetically-modified test cell having elevated lipid content and/or increased lipid droplet level when compared to a native (wild-type) cell of the same type.

In certain embodiments of the screening method, the transformed or genetically-modified test cell is a plant cell. In certain embodiments, the plant test cell is in a plant tissue, plant part, or whole plant.

In certain embodiments of the screening method, vegetative plant (non-seed) cells, tissues or plant parts including, but not limited to, leaves, roots, stems, shoots, buds, tubers, fruits, and flowers, are genetically-modified or transformed. In another embodiment of the screening method, a plant seed cell or tissue is genetically-modified or transformed.

In some embodiments, a method may employ marker-assisted breeding to identify plants, including cultivars or breeding lines, displaying a trait of interest, such as elevated levels of neutral lipids in vegetative portions of plant biomass.

When an exogenous nucleic acid comprising a nucleotide sequence that encodes a lipid droplet-associated protein or polypeptide is introduced into the host cell, lipid content of the test cell is elevated. In certain embodiments, a candidate lipid droplet-associated protein or polypeptide is selected if there is an elevation of the lipid content of the cell of at least about 10%, at least about 20%, at least about 30%, at least about 40%, at least about 50%, at least about 60%, at least about 70%, at least about 80%, or at least about 90%, or more, as compared to a non-genetically-modified host.

In some embodiments, for example, where the exogenous nucleic acid is a plurality of exogenous nucleic acids (such as, for example, a cDNA library, a genomic library, or a population of nucleic acids, each encoding a lipid droplet-associated protein or polypeptide with a different amino acid sequence, etc.), the exogenous nucleic acids are introduced into a plurality of host cells, forming a plurality of test cells. In certain embodiments, the test cells are in some embodiments grown in normal culture conditions.

Methods of isolating the exogenous nucleic acid from a test cell are well known in the art. Suitable methods include, but are not limited to, any of a number of alkaline lysis methods that are standard in the art.

In some embodiments, a subject screening method will further comprise further characterizing a candidate gene product. In these embodiments, the exogenous nucleic acid comprising nucleotide sequence(s) encoding lipid droplet-associated protein or polypeptide are isolated from a test cell; the gene product(s) are expressed in a cell and/or in an in vitro cell-free transcription/translation system. In some embodiments, the exogenous nucleic acid is subjected to nucleotide sequence analysis, and the amino acid sequence of the gene product deduced from the nucleotide sequence. In some embodiments, the amino acid sequence of the gene product is compared with other amino acid sequences in a public database of amino acid sequences, to determine whether any significant amino acid sequence identity to an amino acid sequence of a known protein exists. In addition, the gene product(s) are expressed in a cell and/or in an in vitro cell-free transcription/translation system; and the effect of the gene product(s) on a metabolic pathway intermediate or other metabolite is analyzed.

Exogenous nucleic acids that are suitable for introducing into a host cell, to produce a test cell, include, but are not limited to, naturally-occurring nucleic acids isolated from a cell; naturally-occurring nucleic acids that have been modified (for example, by mutation) before or subsequent to isolation from a cell; synthetic nucleic acids, e.g., nucleic acids synthesized in a laboratory using standard methods of chemical synthesis of nucleic acids, or generated by recombinant methods; synthetic or naturally-occurring nucleic acids that have been amplified in vitro, either within a cell or in a cell-free system; and the like.

Exogenous nucleic acids that are suitable for introducing into a host cell include, but are not limited to, genomic DNA; RNA; a complementary DNA (cDNA) copy of mRNA isolated from a cell; recombinant DNA; and DNA synthesized in vitro, e.g., using standard cell-free in vitro methods for DNA synthesis. In some embodiments, exogenous nucleic acids are a cDNA library made from cells, either prokaryotic cells or eukaryotic cells. In some embodiments, exogenous nucleic acids are a genomic DNA library made from cells, either prokaryotic cells or eukaryotic cells.

Nucleic acids will in some embodiments be mutated before being introduced into a host cell. Methods of mutating a nucleic acid are well known in the art and include well-established chemical mutation methods, radiation-induced mutagenesis, and methods of mutating a nucleic acid during synthesis. Chemical methods of mutating DNA include exposure of DNA to a chemical mutagen, e.g., ethyl methanesulfonate (EMS), methyl methanesulfonate (MMS), N-nitrosourea (ENU), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, .gamma.-irradiation, X-rays, and fast neutron bombardment. Mutations can also be introduced into a nucleic acid using, e.g., trimethylpsoralen with ultraviolet light. Random or targeted insertion of a mobile DNA element, e.g., a transposable element, is another suitable method for generating mutations. Mutations can be introduced into a nucleic acid during amplification in a cell-free in vitro system, e.g., using a polymerase chain reaction (PCR) technique such as error-prone PCR. Mutations can be introduced into a nucleic acid in vitro using DNA shuffling techniques (e.g., exon shuffling, domain swapping, and the like). Mutations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Methods of mutating nucleic acids are well known in the art, and any known method is suitable for use. See, e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

Isolation of Homologs

Isolation of additional homologs from other plant species may be accomplished by laboratory procedures well known and commonly used in the art. Standard techniques are used for identification, cloning, isolation, amplification, and purification of nucleic acid sequences and polypeptides. These techniques and various others are generally performed as described for instance in Sambrook et al., 1989. Genome walking techniques may be performed according to manufacturer's specifications (CLONTECH Laboratories, Inc., Palo Alto, Calif.).

One such technique for isolation of homologs is the use of oligonucleotide probes based on sequences disclosed in this specification to identify the desired gene in a cDNA or genomic DNA library. To construct genomic libraries, large segments of genomic DNA are generated by digestion with restriction endonucleases and then ligating the resultant segments with vector DNA to form concatemers that can be packaged into an appropriate vector. To prepare a cDNA library, mRNA is isolated from the desired organ, such as seed tissue, and a cDNA library is prepared from the mRNA.

A cDNA or genomic DNA library can be screened using a probe based upon the sequence of a cloned naturally-occurring protein or polypeptide sequence. Probes may be used to hybridize with genomic DNA or cDNA sequences to isolate homologous genes in the same or different plant species. Usefully employed such probes include, without limitation, 5' UTRs which, may function as promoters. Alternatively, antibodies raised against a polypeptide, or homolog thereof, can be used to screen an mRNA expression library to isolate sequences of interest. Homologs may also be identified in silico, for instance by similarity-based database searches as described below.

Nucleic acid sequences can be screened for the presence of a protein encoding sequence that is homologous to genes of other organisms with known protein encoding sequence using any of a variety of search algorithms. Such search algorithms can be homology-based or predictive-based. Similarity-based searches (e.g., GAP2, BLASTX supplemented by NAP and TBLASTX) can detect conserved sequences during comparison of DNA sequences or hypothetically translated protein sequences to public and/or proprietary DNA and protein databases.

Existence of a gene is inferred if significant sequence similarity extends over the majority of the target gene. Since such methods may overlook genes unique to the source organism, for which homologous nucleic acid molecules have not yet been identified in databases, gene prediction programs may also be used. Gene prediction programs generally use "signals" in the sequences, such as splice sites or "content" statistics, such as codon bias, to predict gene structures (Stormo, 2000).

Alternatively, the nucleic acids of interest can be amplified from nucleic acid samples using amplification techniques. For example, polymerase chain reaction technology can be used to amplify the sequences of a gene of interest or the homolog gene directly from genomic DNA, from cDNA, from genomic libraries, and cDNA libraries. PCR and other in vitro amplification methods may also be useful, for example, in cloning nucleic acids sequences that code for proteins to be expressed, to make nucleic acids to use as probes for detecting the presence of desired mRNA in samples, for nucleic acid sequencing, or for other purposes.

Appropriate primers and probes for identifying homolog sequences from plant tissues are generated from comparisons of the sequences provided herein. For a general overview of PCR, see, Innis, et al., eds., 1990.

PCR or other primers may be used under standard PCR conditions, preferably using nucleic acid sequences as identified in EST libraries or other GenBank accessions as a template. The PCR products generated by any of the reactions can then be used to identify nucleic acids useful in the context of the present invention by their ability to hybridize to known homolog genes found in GenBank and other databases.

Plant Transformation

To use isolated sequences in the above techniques, recombinant DNA vectors suitable for transformation of plant cells are prepared. Techniques for transforming a wide variety of higher plant species are well known and described in the technical and scientific literature. See, for example, Weising et al., 1988; and Sambrook et al., 1989. Methods of plant cell culture are well known in the art. A DNA sequence coding for the desired polypeptide, for example a cDNA sequence encoding a full length protein, will preferably be combined with transcriptional and translational initiation regulatory sequences that will direct the transcription of the sequence from the gene in the intended tissues of the transformed plant.

Vectors used for plant transformation may include, for example, plasmids, cosmids, yeast artificial chromosomes (YACs), bacterial artificial chromosomes (BACs), plant artificial chromosomes (PACs), or any suitable cloning system. It is contemplated the utilization of cloning systems with large insert capacities will allow introduction of large DNA sequences comprising more than one selected gene. Introduction of such sequences may be facilitated by use of BACs or YACs, or even PACs. For example the use of BACs for Agrobacterium-mediated transformation was disclosed by Hamilton et al., 1999.

Particularly useful for transformation are expression cassettes that have been isolated from such vectors. DNA segments used for transforming plant cells will, of course, generally comprise the cDNA, gene or genes that one desires to introduce into and have expressed in the host cells. These DNA segments can further include structures such as promoter, enhancers, 3' untranslated regions (such as polyadenylation sites), polylinkers, or even regulatory genes as desired. The DNA segment or gene chosen for cellular introduction may encode a protein that will be expressed in the resultant recombinant cells resulting in a screenable or selectable trait and/or will impart an improved phenotype to the resulting transgenic plant. However, this may not always be the case, and the present invention also encompasses transgenic plants incorporating non-expressed transgenes.

A number of promoters that are active in plant cells have been described in the literature, and are preferred elements included in the context of the present invention. Such promoters would include but are not limited to those isolated from the following genes: nopaline synthase (NOS; Ebert et al., 1987) and octopine synthase (OCS): cauliflower mosaic virus (CaMV) 19S (Lawton et al. 1987) and 35S (Odell et al., 1985), as well as the enhanced CaMV 35S promoter (e35S; described by Kay et al., 1987); figwort mosaic virus (FMV) 35S; the small subunit of ribulose bisphosphate carboxylase (ssRUBISCO, a very abundant plant polypeptide); napin (Kridl et al., 1991); Adh (Walker et al., 1987); sucrose synthase (Yang et al., 1990); tubulin; actin (Wang et al., 1992); cab (Sullivan et al., 1989); PEPCase (Hudspeth et al., 1989); 7S-alpha'-conglycinin (Beachy et al., 1985); R gene complex promoters (Chandler et al. 1989); tomato E8; patatin; ubiquitin; mannopine synthase (mas); soybean seed protein glycinin (Gly); soybean vegetative storage protein (vsp); waxy; Brittle; Shrunken 2; Branching enzymes I and II; starch synthases; debranching enzymes; oleosins; glutelins; globulin 1; BETL1; and *Arabidopsis* banyuls promoter. The rice actin 1 promoter, the AGL 11 promoter, the BETL 1 promoter, and the e35S promoter may find use in the practice of the present invention. All of these promoters have been used to create various types of DNA constructs that have been expressed in plants (see, for example, Rogers et al., WO 84/02913).

Promoter hybrids can also be constructed to enhance transcriptional activity (Hoffman, U.S. Pat. No. 5,106,739, herein incorporated by reference), or to combine desired transcriptional activity, inducibility, and tissue or developmental specificity. Promoters that function in plants include but are not limited to promoters that are classified as, among others, inducible, viral, synthetic, constitutive, tissue-specific, developmentally-regulated, chemically or environmentally inducible, or senescence-related, for instance as described (Odell et al., 1985). Promoters that are tissue specific, tissue-enhanced, or developmentally regulated are also known in the art and envisioned to have utility in the practice of this present invention. For instance, a tissue specific promoter, such as the ST-LS1 promoter (e.g. Stockhaus et al., 1989), that is functional in plant vegetative tissues such as leaves, stems, and/or roots, may be of use. Such a promoter may also be expressed to at least some degree in seed or embryo tissues. In certain embodiments, the promoter to be utilized may be expressed preferentially in green parts of a plant such as leaves or stems. A senescence-related promoter (e.g. from SAG12) may also be utilized.

The promoters used in the present invention may be modified to affect their control characteristic. Promoters can be derived by means of ligation with operator regions, random or controlled mutagenesis, or other means well known in the art. Furthermore the promoter regions can be altered to contain multiple enhancer sequences to assist in elevating gene expression. Examples of such enhancer sequences have been reported (Kay et al., 1987).

Where an enhancer is used in conjunction with a promoter for the expression of a selected protein, it is believed that it will be preferred to place the enhancer between the promoter and the start codon of the selected coding region. However, one could also use a different arrangement of the enhancer relative to other sequences and still realize the beneficial properties conferred by the enhancer. For example, the enhancer could be placed 5' of the promoter region, within the promoter region, within the coding sequence, or 3' of the coding region. The placement and choice of sequences used as enhancers is known to those of skill in the art in light of the present disclosure. Transformation constructs prepared in accordance with the current invention will typically include a 3' untranslated region (3' UTR), and typically contains a polyadenylation sequence. One type of 3' UTR that may be used is a 3' UTR from the nopaline synthase gene of *Agrobacterium tumefaciens* (NOS 3'-end; Bevan et al., 1983). Other 3' UTR sequences can be used and are commonly known to those of skill in the art.

A number of selectable marker genes are known in the art and can be used in the present invention (Wilmink and Dons, 1993). By employing a selectable or screenable marker gene in addition to the gene of interest, one can provide or enhance the ability to identify transformants. Useful selectable marker genes for use in the present invention would include genes that confer resistance to compounds such as antibiotics like kanamycin and herbicides like glyphosate or dicamba. Other selectable markers known in the art may also be used and would fall within the scope of the present invention.

DNA constructs of the present invention may be introduced into the genome of the desired plant host by a variety of techniques that are well known in the art. For example, the DNA construct may be introduced directly into the genomic DNA of the plant cell using techniques such as electroporation and microinjection of plant cell protoplasts, or the DNA constructs can be introduced directly to plant tissue using DNA particle bombardment.

Microinjection techniques are known in the art and well described in the scientific and patent literature. The introduction of DNA constructs using polyethylene glycol precipitation is described in Paszkowski et al., 1984. Electroporation techniques are described in Fromm et al., 1985. Ballistic transformation techniques are described in Klein et al., 1987.

Alternatively, the DNA constructs may be combined with suitable T-DNA flanking regions and introduced into a conventional *Agrobacterium tumefaciens* host vector. The virulence functions of the *Agrobacterium tumefaciens* host direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example, Horsch, 1984; and Fraley, 1983.

After transformation by any of the above transformation techniques, the transformed plant cells or tissues may be grown in an appropriate medium to promote cell proliferation and regeneration. Plant regeneration from cultured protoplasts is described in Evans et al., 1983; and Binding, Regeneration of Plants, Plant Protoplasts, pp. 21 73, CRC Press, Boca Raton, 1985. For gene gun transformation of wheat and maize, see, U.S. Pat. Nos. 6,153,812 and 6,160,208. See also, Christou, 1996. See, also, U.S. Pat. Nos. 5,416,011; 5,463,174; and 5,959,179 for *Agrobacterium*-mediated transformation of soy; U.S. Pat. Nos. 5,591,616 and 5,731,179 for *Agrobacterium*-mediated transformation of monocots such as maize; and U.S. Pat. No. 6,037,527 for *Agrobacterium*-mediated transformation of cotton. Other Rhizobiaceae may be used for plant cell transformation as well (e.g. Broothaerts et al., 2007).

To generate a subject genetically modified host cell according to the subject invention, one or more nucleic acids comprising nucleotide sequences encoding one or more lipid droplet-associated proteins or polypeptides can be introduced stably or transiently into a parent host cell, using established techniques, including, but not limited to, electroporation, calcium phosphate precipitation, DEAE-dextran mediated transfection, liposome-mediated transfection, particle bombardment, *Agrobacterium*-mediated transformation, and the like. For stable transformation, a nucleic acid will generally further include a selectable marker, for example, any of several well-known selectable markers such as neomycin resistance, ampicillin resistance, tetracycline resistance, chloramphenicol resistance, kanamycin resistance, and the like.

Where a parent host cell has been genetically modified to produce two or more lipid droplet-associated proteins or polypeptides, nucleotide sequences encoding the two or more lipid droplet-associated proteins or polypeptides will in some embodiments each be contained on separate expression vectors. Where the host cell is genetically modified to express one or more lipid droplet-associated proteins or polypeptides, nucleotide sequences encoding the one or more lipid droplet-associated proteins or polypeptides will in some embodiments be contained in a single expression vector. Where nucleotide sequences encoding the one or more lipid droplet-associated proteins or polypeptides are contained in a single expression vector, in some embodiments, the nucleotide sequences will be operably linked to a common control element (for example, a promoter), such that the common control element controls expression of all of the nucleotide sequences on the single expression vector.

Where nucleotide sequences encoding lipid droplet-associated proteins or polypeptides are contained in a single expression vector, in some embodiments, the nucleotide sequences will be operably linked to different control elements (for example, a promoter), such that, the different control elements control expression of each of the nucleotide sequences separately on a single expression vector.

In many embodiments, the exogenous nucleic acid is inserted into an expression vector. Expression vectors that are suitable for use in prokaryotic and eukaryotic host cells are known in the art, and any suitable expression vector can be used. Suitable expression vectors are as described above.

As noted above, an exogenous nucleic acid will in some embodiments be isolated from a cell or an organism in its natural environment. In some embodiments, the nucleic acid of the cell or organism will be mutated before nucleic acid is isolated from the cell or organism. In other embodiments, the exogenous nucleic acid is synthesized in a cell-free system in vitro.

In some embodiments, the exogenous nucleic acid is a synthetic nucleic acid. In some embodiments, a synthetic nucleic acid comprises a nucleotide sequence encoding a variant lipid droplet-associated protein or polypeptide, for example, a variant lipid droplet-associated protein or polypeptide that differs in amino acid sequence by one or more amino acids from a naturally-occurring lipid droplet-associated protein or polypeptide. In some embodiments, a variant lipid droplet-associated protein or polypeptide differs in amino acid sequence by from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 50 amino acids, or from about 50 amino acids to about 60 amino acids, compared to the amino acid sequence of a naturally-occurring parent lipid droplet-associated protein or polypeptide.

In some embodiments, a nucleic acid comprising a nucleotide sequence encoding a naturally-occurring lipid droplet-associated protein or polypeptide is mutated, using any of a variety of well-established methods, giving rise to a nucleic acid comprising a nucleotide sequence encoding a variant lipid droplet-associated protein or polypeptide.

Suitable mutagenesis methods include, but are not limited to, chemical mutation methods, radiation-induced mutagenesis, and methods of mutating a nucleic acid during synthesis, as described above. Thus, for example, a nucleic acid comprising a nucleotide sequence encoding a naturally-occurring lipid droplet-associated protein or polypeptide is exposed to a chemical mutagen, as described above, or subjected to radiation mutation, or subjected to an error-prone PCR, and the mutagenized nucleic acid introduced into a genetically modified host cell(s) as described above. Methods for random mutagenesis using a "mutator" strain of bacteria are also well known in the art and can be used to generate a variant. See, e.g., Greener et al., "An Efficient Random Mutagenesis Technique Using an *E. coli* Mutator Strain", *Methods in Molecular Biology,* 57:375-385 (1995). Saturation mutagenesis techniques employing a polymerase chain reaction (PCR) are also well known and can be used. See, e.g., U.S. Pat. No. 6,171,820.

An embodiment of the invention provides a host cell comprising a vector according to the invention. Other embodiments include plant plastid transformation vectors or nuclear transformation vectors containing nucleotide sequences encoding lipid droplet-associated proteins or polypeptides, such as containing the full-length lipid droplet-associated protein or polypeptide, or variants or fragments thereof, for the expression of the lipid droplet-associated protein or polypeptide with elevated lipid content in the plant cell. These plant vectors may contain other sequences for the generation of chimeric lipid droplet-associated proteins or polypeptides which may contain mutations, deletions, or insertions of nucleic acid sequences.

According to embodiments of the present invention, a wide variety of plants and plant cell systems can be engineered for the desired physiological and agronomic characteristics described herein using the nucleic acid constructs of the present invention by various transformation methods known in the art, including *Agrobacterium*-mediated transformation (Horsch et al., *Science* 227: 1227-1231, 1985) or plastid transformation (Staub and Maliga, *Plant J.* 6: 547-553, 1994; Hahn and Kuehnle, 2003, cited herein above).

In preferred embodiments, target plants and plant cells for engineering include, but are not limited to, those monocotyledonous and dicotyledonous plants, such as crops, including grain crops (for example, wheat, maize, rice, millet, barley), tobacco, fruit crops (for example, tomato, strawberry, orange, grapefruit, banana), forage crops (for example, alfalfa), root vegetable crops (for example, carrot, potato, sugar beets, yam), leafy vegetable crops (for example, lettuce, spinach); flowering plants (for example, petunia, rose, chrysanthemum), conifers and pine trees (for example, pine, fir, spruce); oil crops (for example, sunflower, rape seed); and plants used for experimental purposes (for example, *Arabidopsis*).

According to other embodiments of the present invention, desired plants may be obtained by engineering one or more of the vectors expressing lipid droplet-associated proteins or polypeptides as described herein into a variety of plant cell types, including but not limited to, protoplasts, tissue culture cells, tissue and organ explants, pollens, embryos, as well as whole plants. In an embodiment of the present invention, the engineered plant material is selected or screened for transformants (those that have incorporated or integrated the introduced gene construct(s)) following the approaches and methods described below. An isolated transformant may then be regenerated into a plant and progeny thereof (including the immediate and subsequent generations) via sexual or asexual reproduction or growth. Alternatively, the engineered plant material may be regenerated into a plant before subjecting the derived plant to selection or screening for the marker gene traits. Procedures for regenerating plants from plant cells, tissues or organs, either before or after selecting or screening for marker gene(s), are well known to those skilled in the art.

According to another embodiment of the present invention, tissue-specific promoters may be used to target the expression of lipid droplet-associated proteins or polypeptides in fruits, roots or leaves so that an edible plant part is provided low-temperature tolerance. Examples of tissue-specific promoters include those encoding rbsC (Coruzzi et al., *EMBO J.* 3:1671-1697, 1984) for leaf-specific expression and SAHH or SHMT (Sivanandan et al., *Biochimica et Biophysica Acta* 1731:202-208, 2005) for root-specific expression. Another exemplary root-specific promoter is taught by Ekramoddoullah et al., U.S. Pat. No. 7,285,656 B2. Also, the Cauliflower Mosaic Virus (CaMV) 35S promoter has been reported to have root-specific and leaf-specific modules in its promoter region (Benfey et al., *EMBO J.* 8:2195-2202, 1989). Other tissue-specific promoters are well known and widely available to those of ordinary skill in the art. Further, a wide variety of constitutive or inducible promoters are also well known and widely available to those of ordinary skill in the art.

Proplastid and chloroplast genetic engineering have been shown to varying degrees of homoplasmy for several major agronomic crops including potato, rice, maize, soybean, grape, sweet potato, and tobacco including starting from non-green tissues. Non-lethal selection on antibiotics is used to proliferate cells containing plastids with antibiotic resistance genes. Plastid transformation methods use two plastid-DNA flanking sequences that recombine with plastid sequences to insert chimeric DNA into the spacer regions between functional genes of the plastome, as is established in the field (see Bock and Hagemann, Prog. Bot. 61:76-90, 2000, and Guda et al., Plant Cell Reports 19:257-262, 2000, and references therein).

Antibiotics such as spectinomycin, streptomycin, and kanamycin can shut down gene expression in chloroplasts by ribosome inactivation. These antibiotics bleach leaves and form white callus when tissue is put onto regeneration medium in their presence. The bacterial genes aadA and neo encode the enzymes aminoglycoside-3N-adenyltransferase and neomycin phosphotransferase, which inactivate these antibiotics, and can be used for positive selection of plastids engineered to express these genes. Polynucleotides of interest can be linked to the selectable genes and thus can be enriched by selection during the sorting out of engineered and non-engineered plastids. Consequently, cells with plastids engineered to contain genes for these enzymes (and linkages thereto) can overcome the effects of inhibitors in the plant cell culture medium and can proliferate, while cells lacking engineered plastids cannot proliferate. Similarly, plastids engineered with polynucleotides encoding enzymes from the mevalonate pathway to produce IPP from acetyl CoA in the presence of inhibitors of the non-mevalonate pathway can overcome otherwise inhibitory culture conditions. By utilizing the polynucleotides disclosed herein in accord with this invention, an inhibitor targeting the non-mevalonate pathway and its components can be used for selection purposes of transplastomic plants produced through currently available methods, or any future methods which become known for production of transplastomic plants, to contain and express said polynucleotides and any linked coding sequences of interest.

This selection process of the subject invention is unique in that it is the first selectable trait that acts by pathway complementation to overcome inhibitors. This is distinguished from the state of the art of selection by other antibiotics to which resistance is conferred by inactivation of the antibiotic itself, e.g. compound inactivation as for the aminoglyoside 3'-adenyltransferase gene or neo gene. This method avoids the occurrence of resistant escapes due to random insertion of the resistance gene into the nuclear genome or by spontaneous mutation of the ribosomal target of the antibiotic, as is known to occur in the state of the art. Moreover, this method requires the presence of an entire functioning mevalonate pathway in plastids. For example, if one of the enzyme activities of the mevalonate pathway is not present in the plastid, resistance will not be conferred.

A transformed plant cell, callus, tissue, or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the vector of the present invention. Such selection and screening methodologies are well known to those skilled in the art. Alternatively or in addition, screening may be for improved low-temperature tolerance as taught herein, for example, by observing a reduction in growth-inhibition.

Physical and biochemical methods may also be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme activity, where such gene products are encoded by the gene construct; 4) protein gel electrophoresis (PAGE), Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art. In a specific embodiment, the selectable marker gene nptII, which specifies kanamycin-resistance, is used in nuclear transformation.

Following transformation, a plant may be regenerated, e.g., from single cells, callus tissue, or leaf discs, as is standard in the art. Almost any plant can be entirely regenerated from cells, tissues, and organs of the plant. Available techniques are reviewed in Vasil et al. (1984) in *Cell Culture and Somatic Cell Genetics of Plants, Vols. I, II, and III, Laboratory Procedures and Their Applications* (Academic press); and Weissbach et al. (1989) *Methods for Plant Mol. Biol.*

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved.

The particular choice of a transformation technology will be determined by its efficiency to transform certain target species, as well as the experience and preference of the person practicing the invention with a particular methodology of choice. It will be apparent to the skilled person that the particular choice of a transformation system to introduce nucleic acid into plant plastids is not essential to or a limitation of the invention, nor is the choice of technique for plant regeneration.

Applications

In certain embodiments, the present invention can be used to:

a) provide higher efficiency and cost effective energy production;
b) increase production of lipids which are beneficial for human health, e.g., omega-unsaturated fat in olives, canola, corns, peanuts, sunflower seeds, etc;
c) generate plants for protein therapy. Some proteins play a positive regulatory role in improving the metabolic health in humans suffering from insulin resistance, type 2 diabetes, cardiovascular diseases etc.;
d) produce genetically-modified plants with elevated lipid content for feeding animals including livestock such as cows to produce milk with high level of lipid droplets;
e) produce genetically-modified algae cells with elevated lipid content for production of biofuels, and feed; and
f) produce genetically-modified bacterial cells expressing lipid droplet-associated proteins for cleaning oil spillage.

Increase the production of oils which are beneficial for human health. Our biochemical analysis shows that FSP27 expression in plants increase omega-6 and omega-3 unsaturated fatty acids.

Expressing fish homologs of FSP27 in combination with other nucleic acid molecules encoding proteins involved in the synthesis of long-chain polyunsaturated fatty acids in plants can be used to increase oil contents in plants, thereby producing plants with high omega-unsaturated fatty acid contents. In one embodiment, the transgenic plants of the present invention can serve as an inexpensive and safe source of dietary fatty acids.

Transgenic plants with high fat contents can be used to feed milk-producing cows, thereby increasing fat contents in dairy products.

The present invention can be used to increase oil contents in oil-producing plants including, but not limited to, olive, canola, sunflower, soybean, castor, and oleaginous fruits such as palm and avocado. The present invention can also be used to increase unsaturated oil contents in plants, to improve the quality and quantity of oil in plants, and to increase oil content in seeds.

The seeds of the transgenic plants with high lipid contents can be used to produce biodegradable plastic (also called as "bioplastic").

The lipid droplet-associated proteins (such as FSP27) can be expressed in algae to increase biofuel production.

Common uses for oils comprising neutral lipids include the preparation of food for human consumption, feed for non-human animal consumption and industrial uses such as for preparation of biofuels.

As used herein, "industrial use" or "industrial usage" refers to non-food and non-feed uses for products prepared from plant parts prepared according to the present invention. As used herein, "biofuel" refers to a fuel combusted to provide power, heat, or energy, e.g. for an internal combustion engine, comprising at least 1%, 5%, 10%, 20% or more, by weight, of an oil, or product thereof, produced from a plant of the present invention, or by a method of the present invention.

Also included in this invention are plants, plant cell cultures, and plant parts thereof, oil obtained from the vegetative tissues of such plants and cells and progeny thereof, animal feed derived from the processing of such tissues, the use of the foregoing oil in food, animal feed, biofuels, cooking oil or industrial applications, and products made from the hydrogenation, fractionation, interesterification or hydrolysis of such oil.

EXAMPLES

Following are examples that illustrate procedures for practicing the invention. The examples should not be construed as limiting.

Example 1—Increase of Lipid Content and Induction of Lipid Droplet Formation in Plants Using Mammalian Lipid Droplet-Associated Proteins Plant transformation vectors are constructed and are propagated in *Eschericia coli* Top 10 cells. The vectors are sequenced for verification. Plasmid vectors are transformed into *Agrobacterium*, tunefaciens LBA4404, and the clones are selected and verified by PCR. *Arabidopsis* plants are transformed by the floral dip method as described in Bent and Clough, Plant J. 1998 December; 16(6):735-43, which is herein incorporated by reference in its entirety.

Both wild-type plants (*Arabidopsis thaliana*, ecotype Columbia), and plants with a transfer DNA (T-DNA) insertion mutation in the At4g24160 locus are used for transformations. The T-DNA knockout is in an exon of the *Arabidopsis* homolog of the human CGI-58 gene. For *Arabidopsis* plants with CGI-58 mutation, there is an increase in cystosolic lipid droplets in leaves when compared to wild-type plants (James et al., Proc Natl Acad Sci USA. 2010 Oct. 12; 107(41):17833-8).

Figure 1B:

FIG. 1 is a diagram that illustrates the elements in the T-DNA regions of plant binary transformation vectors. Plants are allowed to set seed and the seed are screened on hygromycin medium for identification of transgenic plants.

Figure 2:
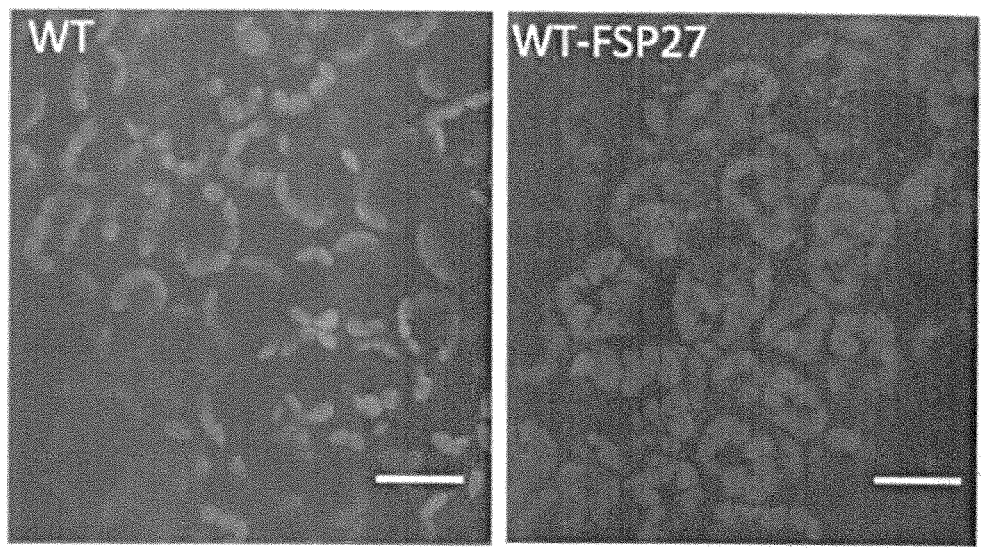
FIG. 2 shows representative Confocal Laser Scanning Microscopy images of leaves of approximately 30-day-old *Arabidopsis thaliana* seedlings stained with Nile blue—a neutral lipid-specific stain. Red autofluorescence emitted from chlorophylls shows the location of chloroplasts distributed around the perimeter of leaf mesophyll cells. Lipid droplets (blue) are distributed throughout the cytosol of the cells and are more abundant in transgenic seedlings expressing mouse FSP27 than in non-transformed cells (WT). Bar is 20 microns.
Figure 3:
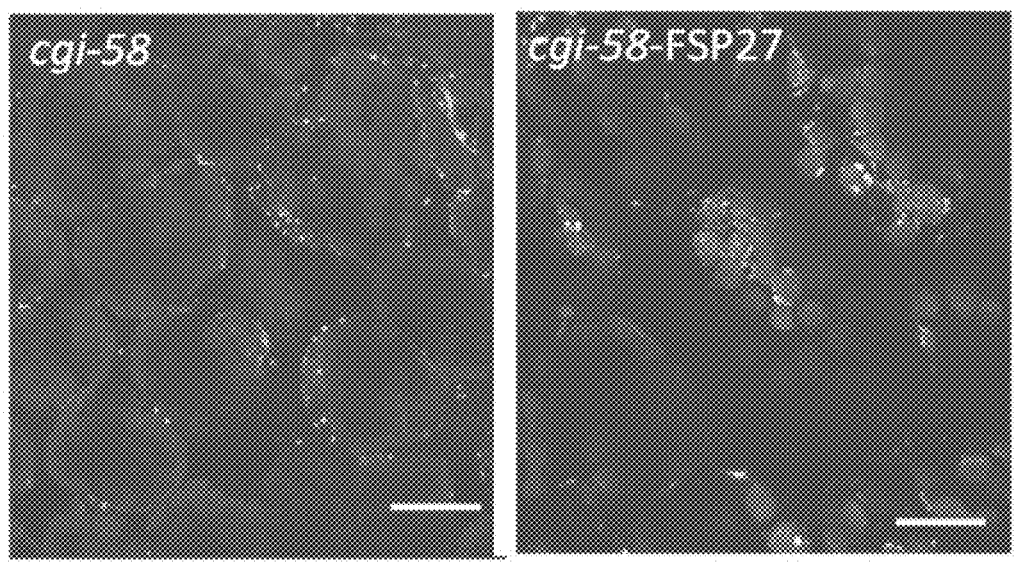
FIG. 3 shows representative Confocal Laser Scanning Microscopy images of leaves of approximately 30-day-old *Arabidopsis thaliana* seedlings stained with BODIPY 493/503—a neutral lipid-specific stain. Red autofluorescence emitted from chlorophylls shows the location of chloroplasts distributed around the perimeter of leaf mesophyll cells. Lipid droplets (yellow-green with BODIPY staining) are distributed throughout the cytosol of the cells and are more abundant in transgenic seedlings expressing mouse FSP27 than in non-transformed cells (cgi58). Bar is 20 microns.
Figure 4:
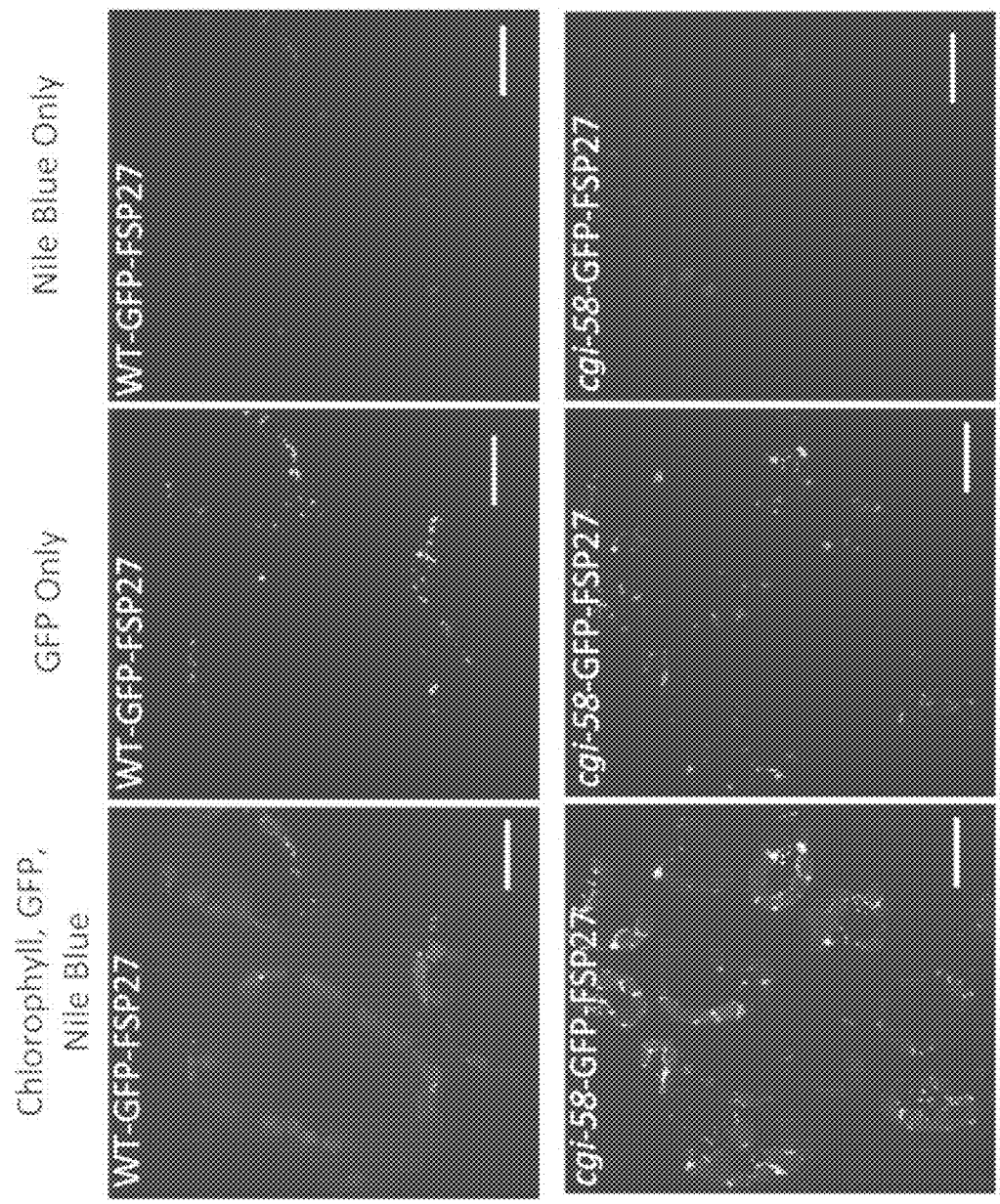
FIG. 4 shows representative Confocal Laser Scanning Microscopy images of leaves of approximately 30-day-old *Arabidopsis thaliana* seedlings stained with Nile blue—a neutral lipid-specific stain. Red autofluorescence emitted from chlorophylls shows the location of chloroplasts distributed around the perimeter of leaf mesophyll cells. GFP fluorescence (green) marks the location of the mouse FSP27-GFP fusion protein. Lipid droplets (blue) are distributed throughout the cytosol of the cells and are more abundant in the cgi58 mutant background than in the wild-type background. More lipid droplets are formed in leaves of transformed plants than in untransformed leaves (see also FIG. 2). Scale bars represent 20 microns.

Cystolic lipid droplets are normally low in abundance in leaves of wildtype plants and they can be visualized by neutral-lipid-specific fluorescent stains like Nile blue (FIG. 2) or Bodipy493/503 (FIG. 3). The loss of function mutant, cgi-58, results in more lipid droplets than in wildtype plants (James et al., Proc Natl Acad Sci USA. 2010 Oct. 12; 107(41):17833-17838; see also FIG. 3. vs. FIG. 2). Expression of mouse FSP27 in either the wild-type or the cgi-58 background accentuates lipid droplet accumulation (FIGS. 2-4).

Total fatty acid content is measured in seedlings as a crude estimate of changes in lipid content. Fatty acid methyl esters are quantified by gas chromatography-flame ionization detection (GC-FID) using heptadecanoic acid as an internal standard. Transgenic T1 seedlings are grown on hygromycin medium, and plants with five rosette leaves are combined for extraction. Total lipids are extracted and fatty acid methyl esters are prepared according to Chapman and Moore (Arch Biochcem Biophys. 1993 Feb. 15; 301(1):21-33), which is herein incorporated by reference in its entirety.

Figure 5:
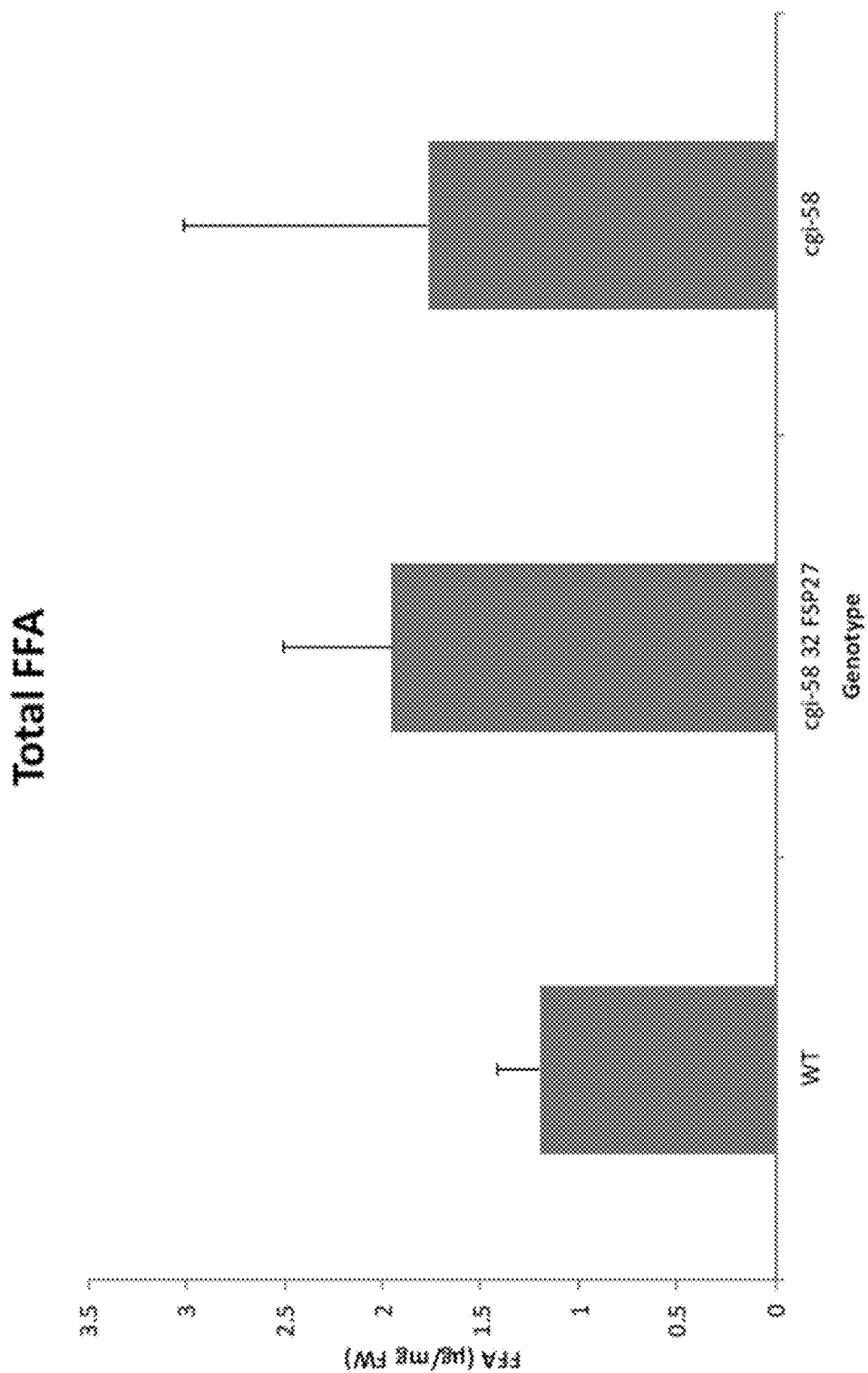
FIG. 5 shows the content of total fatty acids extracted from 15-day-old *Arabidopsis thaliana* seedlings sown on solidified nutrient medium. The total fatty acid content is shown on a fresh weight basis. Transgenic plants (mouse FSP27-GFP in the cgi58 mutant background) in the T1 generation are selected using hygromycin medium. Despite the inclusion of heterozygotes in the analysis, the FSP27-transformed plants exhibit a measureable increase in total lipid content. Also, it is postulated that the transfer of FSP27 stabilizes the variable cgi58 phenotype (reduced standard deviation in the FSP27 expressing plants). Values are the means and standard deviation of three replicates.
Figure 6:
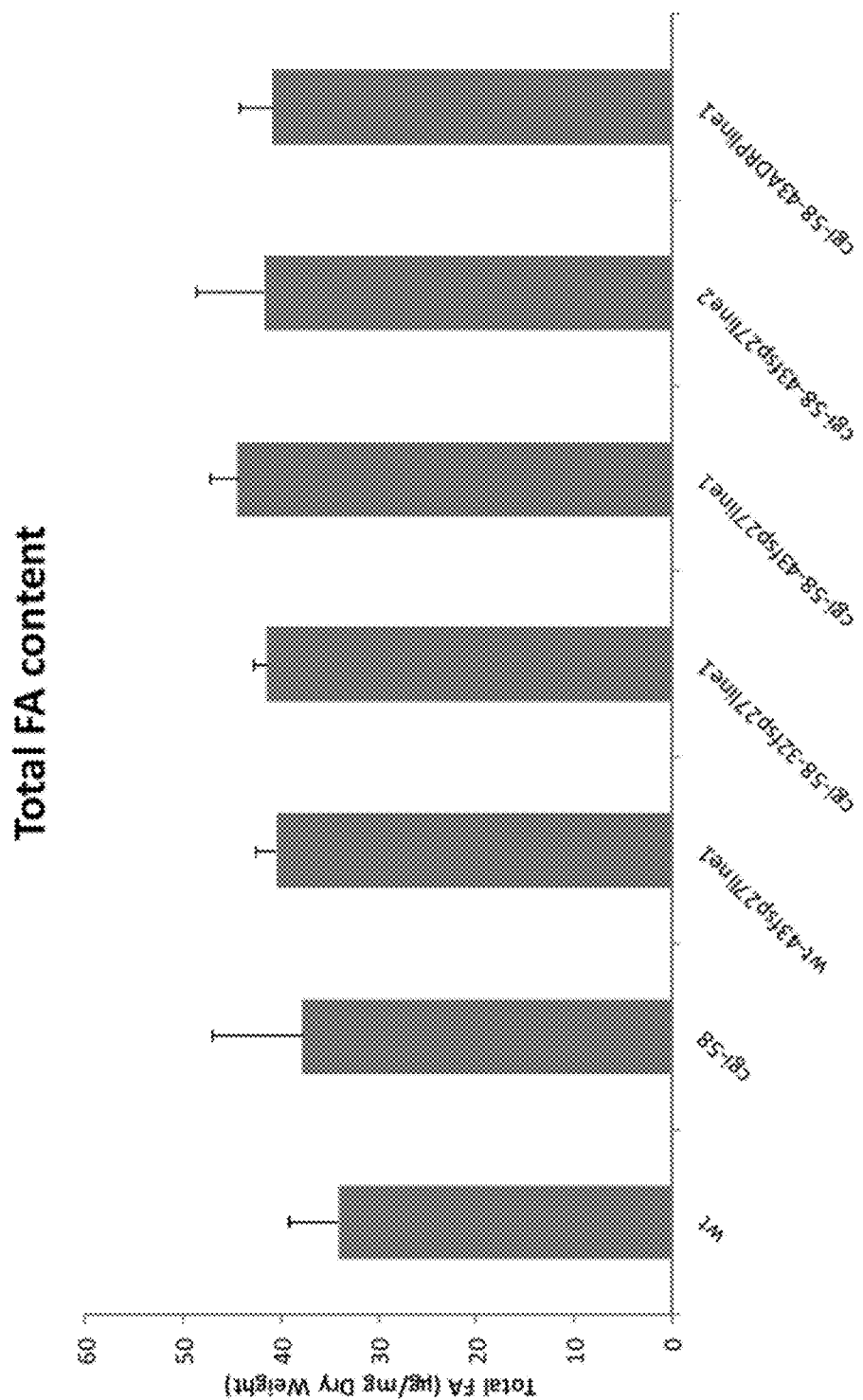
FIG. 6 shows the content of total fatty acids extracted from 15-day-old *Arabidopsis thaliana* seedlings sown on solidified nutrient medium. The total fatty acid content is shown on a dry weight basis. Transgenic plants (expressing mouse FSP27-GFP or mouse autosomal dominant retinitis pigmentosa (ADRP)) in the T1 generation are selected on hygromycin medium. All FSP27-GFP or ADSP transgenic plants have a higher average lipid content in the T1 generation than that of the non-transformed plants, and one line (cgi58-43fsp27line1) has a statistically higher lipid content (P<0.05) than that of non-transformed plants. Values are the means and standard deviations of five replicates.

The results show that transformed lines expressing FSP27 in the T1 generation have higher total fatty acid content than that of corresponding non-transformed plants on a fresh weight (FIG. 5) and a dry weight (FIG. 6) basis. Transformed lines being homozygous for FSP27 will exhibit greater increase in total fat content. Also, there will be a greater increase in total fat content when neutral lipids are separated from polar membrane lipids, since changes in fat content will be in triacylglycerol levels only, but not to bulk changes in membrane lipids.

Figure 7A:
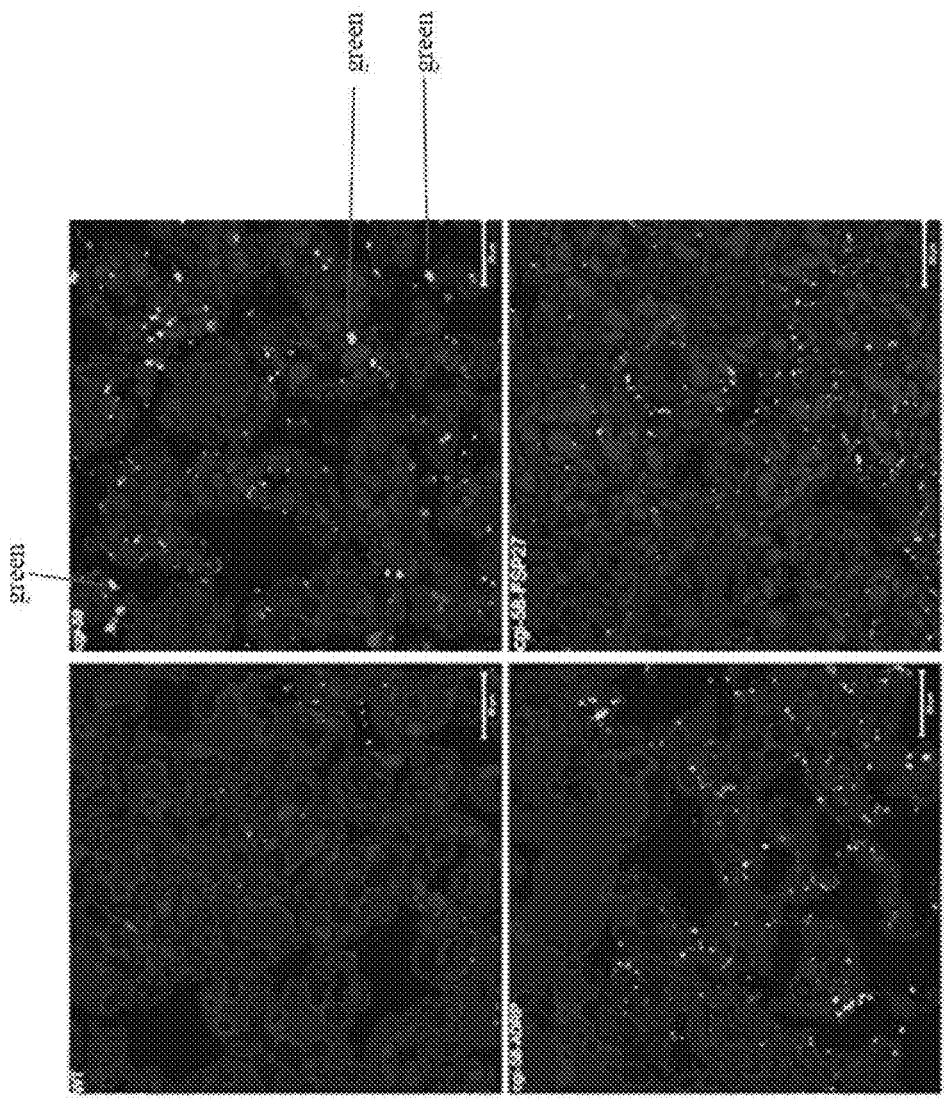
FIG. 7A-C show confocal fluorescence micrographs of leaves in *Arabidopsis* plants expressing ADRP (lower left; A-C) or FSP27 (lower right; A-C) in the cgi58 knockout background. Red autofluorescence is marking chloroplasts; green fluorescence is from the neutral-lipid-specific stain—BODIPY 493/503, showing the accumulation of lipid droplets in leaves. The upper left is wild-type; upper left is the cgi58 knockout background alone.
Figure 7B:
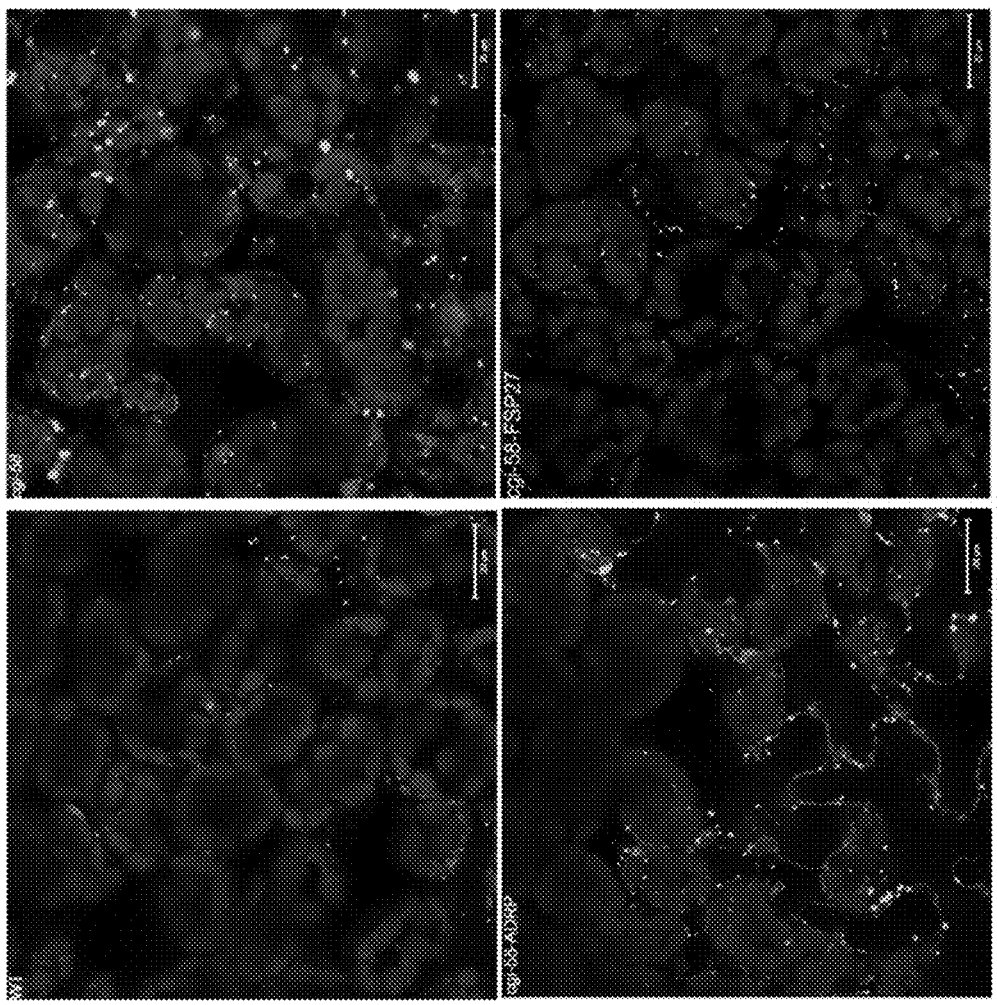
Figure 7C:
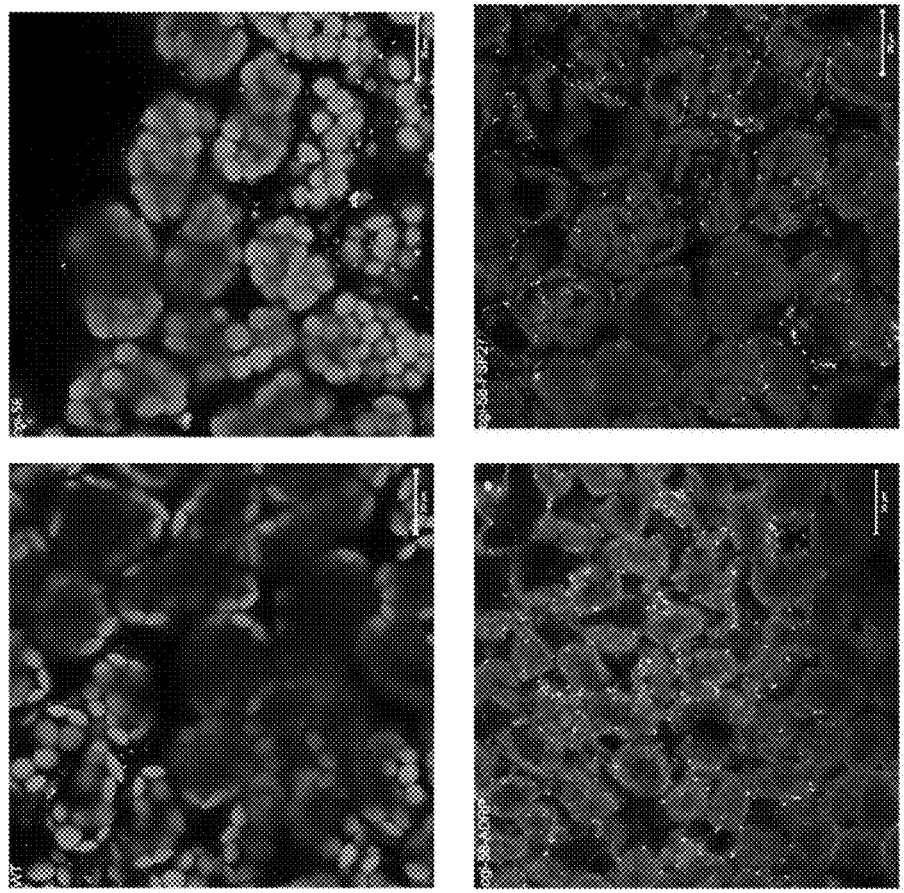

Example 2—Generation of FSP27 and PLIN2 Expressing Homozygous Transgenic Plants with High Lipid Content Seven homozygous lines of FSP27-expressing plants in the cgi58 mutant background, as well as one homozygous line expressing PLIN2 (ADRP) are raised. The new plants are completely viable and healthy with higher lipid accumulation as shown by microscopic data (FIG. 7).

Seedlings are grown on solidified nutrient medium under selection. Seven *Arabidopsis* homozygous lines in T2 generation over-expressing the FSP27 in the cgi58knockout background are identified. Also, one *Arabidopsis* homozygous line in T2 generation overexpressing the ADRP in the cgi58 knockout background is identified. Lines that are no longer segregating (homozygous) are selected for harvest and extraction. FIG. 7 shows representative confocal images of leaves having preponderance of lipid droplets in both lines as well as the cgi-58 knockout background.

Example 3—Identification of Triglyceride-Accumulatory Domain of FSP27

Figures 8, 9:
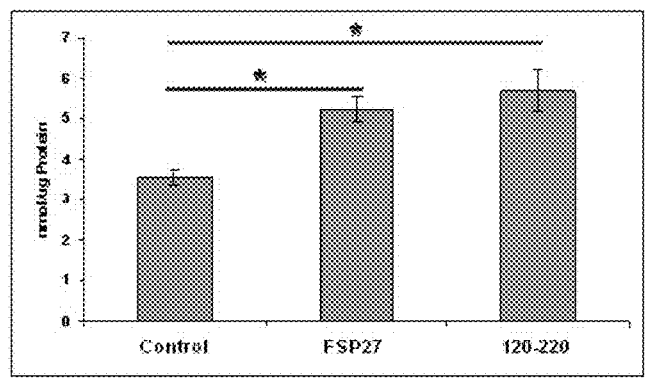
FIG. 8 shows that amino acids 120-220 of FSP27 are associated with lipid accumulation. Amino acids 120-220 of FSP27 and the full length FSP27 are expressed in human adipocytes using lentivirus. X-axis shows total triglycerides in adipocytes. Note that the human adipocytes already have huge amount of triglycerides, and the expression of FSP27 (full length) and FSP27 (120-220) significant increase triglyceride contents in adipocytes by almost 40%. *, p<0.05, t-test.
FIG. 9 shows sequence similarity between mouse and zebra fish FSP27 protein. NP_848460.1: CIDE-3 *Mus musculus* (mouse); NP_001038512.1: CIDE-3 *Danio rerio* (zebra fish).

Using deletion-mutagenesis, the domain of amino acids 120-220 of the mouse FSP27 protein (SEQ ID NO:2), which is associated with lipid accumulation in adipocytes, is dissected. The domain 120-220 of mouse FSP27 is a core-portion of FSP27 protein. As shown in FIG. 8, adipocytes expressing amino acids 120-220 of the mouse FSP27 protein accumulate lipids faster than adipocytes expressing the full length mouse FSP27 protein.

The present invention also provides genetically engineered plants expressing only the triglyceride-accumulating domain of FSP27 (such as amino acids 120-220 of mouse FSP27), in order to accumulate lipids/oils at a faster rate than the full length protein. For the plants that need to be harvested from time to time for biofuel production, expressing the triglyceride-accumulating domain can be useful for improving lipid/or production.

Example 4—Expression of Mammalian and Fish Analogs of FSP27/Cidec/cide-3 in Plants to Increase Lipid Contents Homologs of mammalian lipid droplet-associated proteins can be used to increase lipid/oil contents in transgenic plants. FSP27 plays a key role in triglyceride accumulation in mammals such as mouse and humans. As shown in FIG. 9, mammalian FSP27 and the zebra fish homolog of FSP27 protein share higher than 85% sequence similarity. In one embodiment, mammalian FSP27 and/or fish homologs of FSP27 can be used for expression in plants to generate transgenic plants with high oil and/or lipid contents.

Example 5—Increase of Lipid Content in Plants by Expressing a Combination of Lipid Droplet-Associated Proteins In certain embodiments, to increase and maximize the efficiency of oil production in plants, transgenic plants are genetically modified to express a combination of lipid droplet-associated proteins and peptides. Lipid droplet-associate proteins and peptides useful for improving plant lipid/oil content include, but are not limited to, proteins and peptides involved in lipid (such as triglyceride) metabolism, such as, for example, proteins involved in the synthesis, protection, accumulation, storage, and breakdown of lipid (such as triglyceride).

For instance, FSP27 expression in plants increase plant lipid/oil content, and FSP27 expressed in CGI58-mutants results in even greater increase in lipid/oil content.

In certain embodiments, the present invention provides transgenic plants expressing a combination of lipid droplet-associated proteins including, but not limited to, DGAT-1, PDAT-1, cgi58 mutation, seipin, FIT1, FIT2, PLIN1, PLIN2, FSP27/Cidec/cide-3, and Cidea.

In certain embodiments, the transgenic plants express a combination of nucleic acids expressing lipid droplet-associated proteins selected from: DGAT-1 and FSP27; DGAT-1, cgi58 (mutation), and FSP27; DGAT-1, PDAT-1, and FSP27; DGAT-1, PDAT-1, cgi58 (mutation), FSP27; FSP27, PLIN2, and cgi58 (mutation); DGAT-1, FSP27, PLIN2, and cgi58 (mutation); and DGAT-1, PDAT-1, FSP27, PLIN2, and cgi58 (mutation).

In one embodiment, a combination of "triglyceride accumulation" proteins is expressed in leaves of plants with globally up-regulated fatty acid biosynthesis. Plants with globally up-regulated fatty acid biosynthesis include, but are not limited to, plants with the WRINKLED1 transcription factor mis-expressed in leaves. The WRINKLED1 transcription is involved in the regulation of fatty acid biosynthesis. See Sanjaya et al., 2011, Plant Biotechnology Journal (2011) 9, pp. 874-883), which is hereby incorporated as reference in its entirety.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described

REFERENCES

Curtis and Grossniklaus, A gateway cloning vector set for high-throughput functinal analysis of genes in planta, Plant Physiology, Vol. 133, p 462-469 (2003).

Gross et al. (2011) PNAS 108, 19581-19586; PMID: 22106267.

Jambunathan et al., FSP27 promotes lipid droplet clustering and then fusion to regulate triglyceride accumulation (2011).

James et al. (2010) PNAS 107, 17833-1838, PMID: 20876112

Sanjaya et al., 2011, Plant Biotechnology Journal (2011) 9, pp. 874-883.

Szymanski et al. (2007) PNAS 104, 20890-5, PMID: 18093937.

Zhang et al. (2009) Plant Cell 21, 3885-901, PMID: 20040537.

U.S. Application Publication No. 2010/0221400

We claim:

1. A method for obtaining a plant or algae cell with elevated lipid content, wherein the method comprises:
   genetically modifying a plant or algae cell to express an exogenous polynucleotide encoding an exogenous protein or polypeptide selected from the group consisting of
   i) fat specific protein 27 (FSP27) having the sequence of SEQ ID NO: 1 or a sequence having at least 95% sequence identity to SEQ ID NO: 1;
   ii) SEIPIN having the sequence of SEQ ID NO: 7 or a sequence having at least 90% sequence identity to SEQ ID NO: 7;
   iii) fat storage-inducing transmembrane protein 2 (FIT2) having the sequence of SEQ ID NO: 11 or a sequence having at least 90% sequence identity to SEQ ID NO: 11; and
   iv) any combination of i) to iii),
   thereby obtaining a genetically-modified plant or algae cell with elevated lipid content;
   wherein, each of FSP27, SEIPIN and FIT2 is of an animal origin; and
   wherein the expression of the exogenous polynucleotide encoding the protein or polypeptide increases lipid content of the genetically-modified plant or algae cell as compared to a wild-type plant or algae cell of the same type.

2. The method according to claim 1, wherein the exogenous protein or polypeptide is FSP27 having the sequence of SEQ ID NO: 1 or a sequence having at least 95% sequence identity to SEQ ID NO: 1.

3. The method according to claim 1, wherein the plant cell is in a plant part.

4. The method according to claim 3, wherein the plant part is in a plant.

5. The method according to claim 1, wherein the plant cell is a non-seed cell.

6. The method according to claim 5, wherein the non-seed cell is in a leaf, root, stem, shoot, bud, tuber, fruit, or flower of the plant.

7. The method according to claim 1, wherein the cell is in a seed of the plant.

8. The method according to claim 1, wherein the genetic modification of the plant or algae cell comprises transforming the plant or algae cell with a vector comprising the exogenous polynucleotide encoding the exogenous protein or polypeptide, wherein the exogenous polynucleotide is operably linked to a promoter and/or a regulatory sequence.

9. The method according to claim 8, wherein the vector is a T-DNA binary vector.

10. A transgenic plant or algae cell with elevated lipid content when compared to a wild-type plant or algae cell of the same type, wherein the transgenic plant or algae cell expresses an exogenous polynucleotide encoding an exogenous protein or polypeptide selected from the group consisting of:
   i) FSP27 having the sequence of SEQ ID NO: 1 or a sequence having at least-90% 95% sequence identity to SEQ ID NO: 1;
   ii) SEIPIN having the sequence of SEQ ID NO: 7 or a sequence having at least 90% sequence identity to SEQ ID NO: 7;

iii) FIT2 having the sequence of SEQ ID NO: 11 or a sequence having at least 90% sequence identity to SEQ ID NO: 11; and iv) any combination of i) to iii);

wherein the protein or polypeptide enhances the accumulation of cellular lipid droplets and/or reduces lipase activity, and wherein each of FSP27, SEIPIN and FIT2 is of an animal origin.

11. The transgenic plant or algae cell according to claim 10, wherein the exogenous protein is FSP27 having the sequence of SEQ ID NO: 1 or a sequence having at least 95% sequence identity to SEQ ID NO: 1.

12. The transgenic plant cell according to claim 10, which is a non-seed cell.

13. The method according to claim 1, wherein the exogenous protein or polypeptide is SEIPIN having the sequence of SEQ ID NO: 7 or a sequence having at least 90% sequence identity to SEQ ID NO: 7.

14. The method according to claim 1, wherein the exogenous protein or polypeptide is FIT2 having the sequence of SEQ ID NO: 11 or a sequence having at least 90% sequence identity to SEQ ID NO: 11.

15. The method of claim 1, wherein: the exogenous protein or polypeptide is selected from the group consisting of:

i) FSP27 having the sequence of SEQ ID NO: 1 or a sequence having at least 95% sequence identity to SEQ ID NO: 1;

ii) SEIPIN having the sequence of SEQ ID NO: 7 or a sequence having at least 95% sequence identity to SEQ ID NO: 7;

iii) FIT2 having the sequence of SEQ ID NO: 11 or a sequence having at least 95% sequence identity to SEQ ID NO: 11; and iv) any combination of i) to iii).

16. The transgenic plant or algae cell of claim 10, wherein: the exogenous protein or polypeptide is selected from the group consisting of:

i) FSP27 having the sequence of SEQ ID NO: 1 or a sequence having at least 95% sequence identity to SEQ ID NO: 1;

ii) SEIPIN having the sequence of SEQ ID NO: 7 or a sequence having at least 95% sequence identity to SEQ ID NO: 7;

iii) FIT2 having the sequence of SEQ ID NO: 11 or a sequence having at least 95% sequence identity to SEQ ID NO: 11; and iv) any combination of i) to iii).

17. The transgenic plant or algae cell of claim 10, wherein the plant cell is in a plant part.

18. The transgenic plant or algae cell of claim 17, wherein the plant part is in a plant.

19. The transgenic plant or algae cell of claim 10, wherein the plant cell is in a seed of a plant.

20. The transgenic plant or algae cell of claim 12, wherein the non-seed cell is in a leaf, root, stem, shoot, bud, tuber, fruit, or flower of the plant.

* * * * *

UNITED STATES PATENT AND TRADEMARK OFFICE
CERTIFICATE OF CORRECTION

PATENT NO. : 10,253,325 B2
APPLICATION NO. : 13/830012
DATED : April 9, 2019
INVENTOR(S) : Vishwajeet Puri, Kent Chapman and Christopher James Page 1 of 1

It is certified that error appears in the above-identified patent and that said Letters Patent is hereby corrected as shown below:

On the Title Page

Item (73) "Assignee: Boston Medical Center Corporation" should read
--Assignee: Boston Medical Center Corporation; University of North Texas--.

Signed and Sealed this
Thirty-first Day of December, 2019

Andrei Iancu
*Director of the United States Patent and Trademark Office*